(12) United States Patent
Chaux et al.

(10) Patent No.: US 11,524,069 B2
(45) Date of Patent: *Dec. 13, 2022

(54) HUMAN CYTOMEGALOVIRUS IMMUNOGENIC COMPOSITION

(71) Applicant: Sanofi Pasteur, Lyons (FR)

(72) Inventors: Pascal Chaux, Bully (FR); Rafaela Dumas, Porquerolles (FR); Jean Haensler, Grezieu la Varenne (FR); Sylvie Pichon, Brindas (FR); Fabienne Piras-Douce, Fleurieux sur l'Arbresle (FR)

(73) Assignee: Sanofi Pasteur, Lyons (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/646,894

(22) PCT Filed: Sep. 11, 2018

(86) PCT No.: PCT/EP2018/074369
§ 371 (c)(1),
(2) Date: Mar. 12, 2020

(87) PCT Pub. No.: WO2019/052975
PCT Pub. Date: Mar. 21, 2019

(65) Prior Publication Data
US 2020/0276301 A1 Sep. 3, 2020

(30) Foreign Application Priority Data

Sep. 13, 2017 (EP) .................... 17306179

(51) Int. Cl.
| | | |
|---|---|---|
| *A61K 39/245* | (2006.01) | |
| *A61P 31/22* | (2006.01) | |
| *A61K 39/39* | (2006.01) | |
| *C12N 7/00* | (2006.01) | |
| *A61K 9/107* | (2006.01) | |
| *A61K 39/00* | (2006.01) | |

(52) U.S. Cl.
CPC ............ *A61K 39/245* (2013.01); *A61K 39/39* (2013.01); *A61P 31/22* (2018.01); *C12N 7/00* (2013.01); *A61K 9/107* (2013.01); *A61K 2039/55516* (2013.01); *A61K 2039/55566* (2013.01)

(58) Field of Classification Search
CPC ...... A61K 39/245; A61K 39/39; A61K 9/107; A61K 2039/55516; A61K 2039/55566; A61K 2039/55555; A61K 2039/55572; A61K 2039/525; A61P 31/22; C12N 7/00; C12N 2710/16111; C12N 2710/16122; C12N 2710/16134; C07K 16/088

See application file for complete search history.

(56) References Cited

U.S. PATENT DOCUMENTS

| | | | |
|---|---|---|---|
| 4,912,094 A | 3/1990 | Myers et al. | |
| 5,057,540 A | 10/1991 | Kensil et al. | |
| 5,547,834 A | 8/1996 | Spaete et al. | |
| 6,100,064 A | 8/2000 | Burke et al. | |
| 6,113,918 A | 9/2000 | Johnson et al. | |
| 9,480,740 B2 | 11/2016 | Reed et al. | |
| 2002/0102562 A1 | 8/2002 | Spaete et al. | |
| 2003/0153532 A1 | 8/2003 | Hawkins et al. | |
| 2005/0164988 A1 | 7/2005 | Hawkins et al. | |
| 2008/0187545 A1* | 8/2008 | Shenk | C12N 7/00 435/7.1 |
| 2009/0104227 A1* | 4/2009 | Pass | A61K 39/12 424/204.1 |
| 2015/0216965 A1* | 8/2015 | Diamond | A61K 39/12 424/230.1 |
| 2015/0335733 A1* | 11/2015 | Dubensky, Jr | A61K 39/001109 424/186.1 |
| 2015/0359879 A1* | 12/2015 | Wellnitz | C07K 14/005 424/230.1 |
| 2017/0360923 A1* | 12/2017 | Rigaut | A61K 47/26 |
| 2019/0321464 A1* | 10/2019 | Ciaramella | A61K 31/7105 |
| 2020/0157191 A1* | 5/2020 | Diamond | A61K 39/12 |

FOREIGN PATENT DOCUMENTS

| | | |
|---|---|---|
| EP | 0671948 | 9/1995 |
| EP | 1318835 | 6/2003 |
| EP | 2437753 | 4/2012 |
| EP | 2627352 | 8/2013 |
| GB | 2211502 | 7/1989 |
| WO | WO 88/09336 | 12/1988 |
| WO | WO 96/04382 | 2/1996 |
| WO | WO 98/50399 | 11/1998 |
| WO | WO 2001/034617 | 5/2001 |
| WO | WO 02/024225 | 3/2002 |
| WO | WO 2004/060396 | 7/2004 |
| WO | WO 2007/080308 | 7/2007 |
| WO | WO 2009/109550 | 9/2009 |
| WO | WO 2010/141861 | 12/2010 |
| WO | WO 2012/049317 | 4/2012 |
| WO | WO 2012/051211 | 4/2012 |
| WO | WO 2014/005959 | 1/2014 |
| WO | WO 2016/092460 | 6/2016 |

OTHER PUBLICATIONS

Bernstein DI, Munoz FM, Callahan ST, Rupp R, Wootton SH, Edwards KM, Turley CB, Stanberry LR, Patel SM, Mcneal MM, et al. Safety and efficacy of a cytomegalovirus glycoprotein B (gB) vaccine in adolescent girls: A randomized clinical trial. Vaccine. Jan. 12, 2016;34(3):313-9. Epub Dec. 2, 2015. (Year: 2016).*

(Continued)

*Primary Examiner* — Rachel B Gill
(74) *Attorney, Agent, or Firm* — Fish & Richardson P.C.

(57) ABSTRACT

The invention relates to an immunogenic composition comprising an HCMV gB antigen, an HCMV gH/gL/UL128/UL130/UL131 pentameric complex antigen and a Th1-inducing adjuvant. If further relates to the immunogenic composition for use as an HCMV vaccine.

20 Claims, 9 Drawing Sheets

Figure 1:
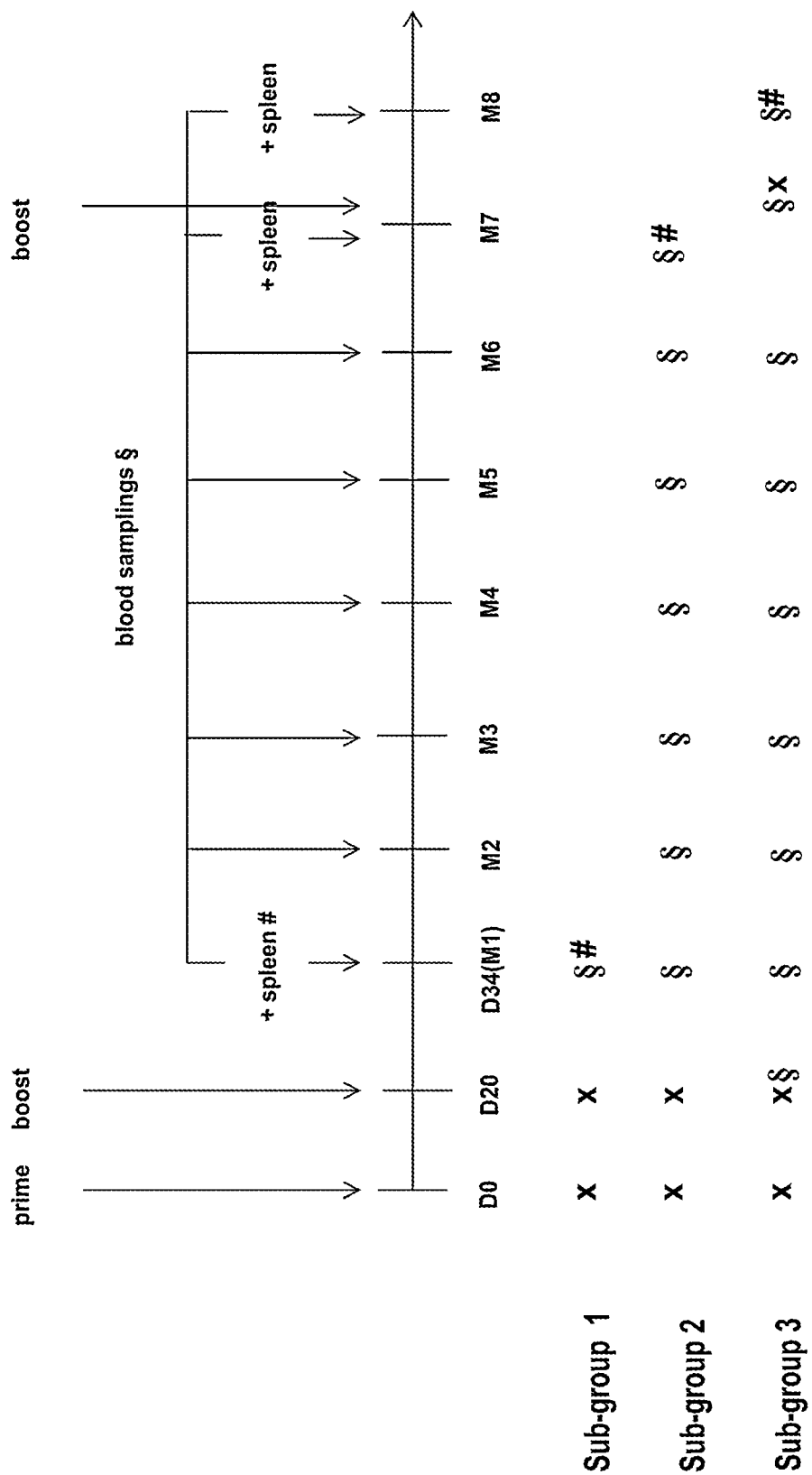

Specification includes a Sequence Listing.

(56) References Cited

OTHER PUBLICATIONS

Haensler J, Probeck P, Su J, Piras F, Dalençon F, Cotte JF, Chambon V, et al. Design and preclinical characterization of a novel vaccine adjuvant formulation consisting of a synthetic TLR4 agonist in a thermoreversible squalene emulsion. Int J Pharm. 2015;486(1-2):99-111. Epub Mar. 17, 2015. (Year: 2015).*
Barry PA. Exploiting viral natural history for vaccine development. Med Microbiol Immunol. Jun. 2015;204(3):255-62. Epub Mar. 21, 2015. (Year: 2015).*
McVoy MA. Cytomegalovirus vaccines. Clin Infect Dis. Dec. 2013;57 Suppl 4(Suppl 4):S196-9. doi: 10.1093/cid/cit587. PMID: 24257427; PMCID: PMC3836572. (Year: 2013).*
Charlton Hume HK, Lua LHL. Platform technologies for modern vaccine manufacturing. Vaccine. Aug. 16, 2017;35(35 Pt A):4480-4485. Epub Mar. 25, 2017. (Year: 2017).*
Reichmuth AM, Oberli MA, Jaklenec A, Langer R, Blankschtein D. mRNA vaccine delivery using lipid nanoparticles. Ther Deliv. 2016;7(5):319-34. Erratum in: Ther Deliv. Jun. 2016;7(6):411. (Year: 2016).*
Kardani K, Bolhassani A, Shahbazi S. Prime-boost vaccine strategy against viral infections: Mechanisms and benefits. Vaccine. Jan. 20, 2016;34(4):413-423. Epub Dec. 13, 2015. (Year: 2015).*
Noad R, Roy P. Virus-like particles as immunogens. Trends Microbiol. Sep. 2003;11(9):438-44. (Year: 2003).*
Wussow F, Chiuppesi F, Martinez J, Campo J, Johnson E, Flechsig C, Newell M, Tran E, Ortiz J, La Rosa C, Herrmann A, Longmate J, Chakraborty R, Barry PA, Diamond DJ. Human cytomegalovirus vaccine based on the envelope gH/gL pentamer complex. PLoS Pathog. Nov. 20, 2014;10(11):e1004524. (Year: 2014).*
Jackson SE, Sedikides GX, Mason GM, Okecha G, Wills MR. Human Cytomegalovirus (HCMV)-Specific CD4+ T Cells Are Polyfunctional and Can Respond to HCMV-Infected Dendritic Cells In Vitro. J Virol. Feb. 28, 2017;91(6):e02128-16. (Year: 2017).*
Anderholm et al., "Cytomegalovirus vaccines: Current status and future prospects," Drugs 76(17):1625-1645, Nov. 1, 2016.
Ciferri et al., "Structural and biochemical studies of HCMV gH/gL/gO and pentamer reveal mutually exclusive cell entry complexes," Proceedings of the National Academy of Sciences 112(6):1767-1772, Jan. 26, 2015.
Freed et al., "Pentameric complex of viral glycoprotein H is the primary target for potent neutralization by a human cytomegalovirus vaccine," Proceedings of the National Academy of Sciences 110(51):E4997-E5005, Dec. 2, 2013.
Griffiths et al., "Cytomegalovirus glycoprotein-B vaccine with MF59 adjuvant in transplant recipients: a phase 2 randomised placebo-controlled trial," Lancet 377(9773):1256-63, 2011.
International Preliminary Report and Written Opinion in Application No. PCT/EP2018/074369, dated Mar. 17, 2020, 10 pages.
International Search Report and Written Opinion in Application No. PCT/EP2018/074369, dated Oct. 5, 2018, 15 pages.
Loughney et al., "Soluble human cytomegalovirus gH/gL/pUL128-131 pentameric complex, but not gH/gL, inhibits viral entry to epithelial cells and presents dominant native neutralizing epitopes," 290(26):15985-15995, May 6, 2015.
Macagno et al., "Isolation of human monoclonal antibodies that potently neutralize human cytomegalovirus infection by targeting different epitopes on gH/gL/UL128-131A complex," 84(2):1005-1013, Jan. 15, 2010.
Pass et al., "Vaccine prevention of maternal cytomegalovirus infection," The New England Journal of Medicine 360:1191-9, 2009.
Patrone et al., "Human Cytomegalovirus UL130 protein promotes endothelial cell infection through a producer cell modification of the virion," Journal of Virology 79:8361-73, 2005.
Ryckman et al., "Characterization of the human cytomegalovims gH/gL/UL128-131 complex that mediates entry into epithelial and endothelial cells," Journal of Virology 82(1):60-70, Jan. 2008.

Wen et al., "Human cytomegalovirus gH/gL/UL128/UL130/UL131A complex elicits potently neutralizing antibodies in mice," Vaccine 32(30):3796-3804, Jun. 1, 2014.
Axelsson et al., "Humoral immunity targeting site I of antigenic domain 2 of glycoprotein B upon immunization with different cytomegalovirus candidate vaccines," Vaccine, 2007, 26(1):41-46, Dec. 2007.
Backovic et al., "Structure of a trimeric variant of the Epstein-Barr virus glycoprotein," PNAS 106(8):2880-2885, Feb. 2009.
Burke et al., "Crystal structure of the human cytomegalovirus glycoprotein B," PLoS pathogens 11(10):e1005227, Oct. 2015.
Carter et al., "A structure-function approach to optimizing TLR4 ligands for human vaccines," Clinical Translational Immunology 5(11):e108, Nov. 2016.
Dar et al., "Administration of poly[di(sodium carboxylatoethylphenoxy)]phosphazene (PCEP) as adjuvant activated mixed Th1/Th2 immune responses in pigs," Veterinary Immunology Immunopathology, 146(3-4):289-295, May 2012.
Garcon et al., "GlaxoSmithKline Adjuvant Systems in vaccines: concepts, achievements and perspectives," Expert Review of Vaccines 6(5):723-739, Oct. 2007.
Heldwein et al., "Crystal structure of glycoprotein B from herpes simplex virus 1", Science 313(5784):217-220, Jul. 2006.
Henikoff and Henikoff et al., "Amino acid substitution matrices from protein blocks," PNAS 89:10915-19, Nov. 1992.
Lien et al., "A novel synthetic acyclic lipid a-like agonist activates cells via the lipopolysaccharide/toll-like receptor 4 signaling pathway," Journal of Biological Chemistry 276(3):1873-80, Jan. 2001.
Lu et al., "VTX-2337 is a novel TLR8 agonist that activates NK cells and augments ADCC," Clinical Cancer Research 18(2):499-509, Nov. 2011.
Needleman et al., "A general method applicable to the search for similarities in the amino acid sequence of two proteins," Journal of Molecular Biology 48(3):443-53, Mar. 1970.
Plotkin et al., Vaccines, 6th edition, Ed. Elsevier, 2013, Schleiss et al., "Cytomegalovirus vaccines," pp. 1032-1041.
Schoppel et al., "Antibodies specific for the antigenic domain 1 of glycoprotein B (gpUL55) of human cytomegalovirus bind to different substructures," Virology 216(1):133-145, Feb. 1996.
Stratton et al., Editors committee to study priorities for Vaccine Development Division of Health Promotion and Disease Prevention Institute of Medicine. "Vaccines for the 21st century: A tool for decision making," Washington D.C.: National Academy Press; 2000.
Vollmer et al., "Progress in dmg development of immunostimulatory CpG oligodeoxynucleotide ligands for TLR9," Expert Opinion on Biological Therapy 5(5):673-682, May 2005.
Wang et al., "Human cytomegalovirus UL131 open reading frame is required for epithelial cell tropism," Journal of Virology 79(16):10330-10338, Aug. 2005.
Yan et al., "Effects of ultrasound on molecular properties, structure, chain conformation and degradation kinetics of carboxylic curdlan," Carbohydrate Polymers 121:64-70, May 2015.
Yu et al., "Molecular imaging and analysis of branching topology in polyacrylates by atomic force microscopy," Macromolecules 44(15):5928-5936, Aug. 2011.
Constant et al., "Induction of Th1 and Th2 CD4$^+$T cell responses: The alternative approaches," Annual Review of Immunology, 1997, 15:297-322.
Hofmann et al., "Expression of the human cytomegalovirus pentamer complex for vaccine use in a CHO system," Biotechnology and Bioengineering, Jun. 2015, 11 pages.
Katzen et al., "The past, present and future of cell-free protein synthesis," Trends in Biotechnology, Mar. 2005, 23(3):150-156.
Kremkow et al., "CHOgenome.org 2.0: Genome resources and website updates," Biotechnology Journal, Apr. 2015, 10(7):931-938.
Merrifield, "Solid Phase Peptide Synthesis. I. The Synthesis of a Tetrapeptide," Journal of the American Chemical Society, 1963, 85(14): 2149-2154.
Morihara, "Using proteases in peptide synthesis," Trends in Biotechnology, Jun. 1987, 5(6):164-170.

(56) References Cited

OTHER PUBLICATIONS

Non-Final Office Action in U.S. Appl. No. 17/071,817, dated May 5, 2021, 10 pages.

* cited by examiner

| A | day 34 | | day 208 | | day 257 | |
|---|---|---|---|---|---|---|
| Formulation | IgG1 Titre (log10 EU) | IgG2c Titre (log10 EU) | IgG1 Titre (log10 EU) | IgG2c Titre (log10 EU) | IgG1 Titre (log10 EU) | IgG2c Titre (log10 EU) |
| PBS | 1.00 | 1.00 | 1.00 | 1.39 | 1.11 | 1.27 |
| gB and pentamer | 4.48 | 1.83 | 4.24 | 1.51 | 5.49 | 2.75 |
| +MF59 | 6.10 | 4.00 | 5.45 | 3.52 | 6.18 | 4.13 |
| +PAA | 5.50 | 5.55 | 4.87 | 4.81 | 6.14 | 5.92 |
| +AF04 | 6.00 | 5.14 | 5.49 | 4.49 | 6.17 | 5.29 |
| +GLA-SQEM | 5.70 | 5.32 | 4.93 | 4.76 | 5.74 | 5.57 |

| B | day 34 | | day 208 | | day 257 | |
|---|---|---|---|---|---|---|
| Formulation | IgG1 Titre (log10 EU) | IgG2c Titre (log10 EU) | IgG1 Titre (log10 EU) | IgG2c Titre (log10 EU) | IgG1 Titre (log10 EU) | IgG2c Titre (log10 EU) |
| PBS | 1.00 | 1.00 | 1.00 | 1.14 | 1.00 | 1.08 |
| gB and pentamer | 3.89 | 1.39 | 3.39 | 1.67 | 4.76 | 2.50 |
| +MF59 | 5.48 | 4.22 | 4.75 | 3.45 | 5.62 | 4.04 |
| +PAA | 4.88 | 5.34 | 4.36 | 4.68 | 5.58 | 5.73 |
| +AF04 | 5.64 | 5.30 | 4.84 | 4.32 | 5.53 | 5.22 |
| +GLA-SQEM | 5.44 | 5.55 | 4.14 | 4.65 | 5.18 | 5.62 |

FIG. 6

| Adjuvants | Time-point | MF59 | PAA | AF04 | GLA-SQEM |
|---|---|---|---|---|---|
| IgG1/IgG2c ratio for gB | D34 | 124 | 0.9 | 7.1 | 2.4 |
| | D208 | 85 | 1.2 | 9.7 | 1.5 |
| | D257 | 110 | 1.7 | 7.7 | 1.5 |
| IgG1/IgG2c ratio for pentamer | D34 | 18 | 0.3 | 2.2 | 0.8 |
| | D208 | 20 | 0.5 | 3.2 | 0.3 |
| | D257 | 30 | 0.7 | 2.1 | 0.4 |

FIG. 7

| A | day 34 | | day 208 | | day 257 | |
|---|---|---|---|---|---|---|
| Formulation | IL-5 | IFN-g | IL-5 | IFN-g | IL-5 | IFN-g |
| PBS | 1.00 | 2.00 | 1.00 | 1.00 | 5.00 | 2.00 |
| gB and pentamer | 22.00 | 5.00 | 2.00 | 2.00 | 125.00 | 6.00 |
| +MF59 | 60.00 | 10.00 | 21.00 | 1.00 | 268.00 | 3.00 |
| +PAA | 5.00 | 15.00 | 9.00 | 1.00 | 38.00 | 11.00 |
| +AF04 | 13.00 | 9.00 | 7.00 | 1.00 | 15.00 | 7.00 |
| +GLA-SQEM | 13.00 | 12.00 | 2.00 | 1.00 | 3.00 | 63.00 |

| B | day 34 | | day 208 | | day 257 | |
|---|---|---|---|---|---|---|
| Formulation | IL-5 | IFN-g | IL-5 | IFN-g | IL-5 | IFN-g |
| PBS | 1.00 | 2.00 | 1.00 | 2.00 | 6.00 | 4.00 |
| gB and pentamer | 251.00 | 7.00 | 140.00 | 1.00 | 3077.00 | 66.00 |
| +MF59 | 444.00 | 26.00 | 277.00 | 1.00 | 2284.00 | 52.00 |
| +PAA | 82.00 | 462.00 | 108.00 | 16.00 | 330.00 | 848.00 |
| +AF04 | 170.00 | 722.00 | 38.00 | 117.00 | 546.00 | 645.00 |
| +GLA-SQEM | 40.00 | 299.00 | 23.00 | 45.00 | 38.00 | 1405.00 |

FIG. 8

| A | day 34 | | day 208 | | day 257 | |
|---|---|---|---|---|---|---|
| Adjuvants | %IgG1 | %IgG2c | %IgG1 | %IgG2c | %IgG1 | %IgG2c |
| gB+pentamer | 0.46 | 0.00 | 0.00 | 0.00 | 0.71 | 0.04 |
| +MF59 | 12.37 | 0.63 | 0.58 | 0.09 | 3.95 | 0.42 |
| +PAA | 6.63 | 14.76 | 0.40 | 2.59 | 6.88 | 9.87 |
| +AF04 | 20.12 | 12.24 | 0.57 | 0.30 | 7.42 | 2.87 |
| +GLA-SQEM | 4.03 | 3.26 | 0.35 | 1.11 | 2.44 | 4.62 |

| B | day 34 | | day 208 | | day 257 | |
|---|---|---|---|---|---|---|
| Adjuvants | %IgG1 | %IgG2c | %IgG1 | %IgG2c | %IgG1 | %IgG2c |
| gB+pentamer | 0.08 | 0.08 | 0.00 | 0.00 | 0.41 | 0.04 |
| +MF59 | 7.02 | 0.95 | 0.34 | 0.11 | 3.54 | 0.32 |
| +PAA | 3.80 | 5.00 | 0.24 | 0.81 | 4.58 | 5.25 |
| +AF04 | 12.03 | 15.00 | 0.64 | 0.55 | 9.00 | 3.81 |
| +GLA-SQEM | 7.15 | 4.00 | 0.08 | 1.67 | 3.11 | 5.59 |

FIG. 9

| A | day 34 | | day 208 | | day 257 | |
|---|---|---|---|---|---|---|
| Adjuvants | %IgG1 | %IgG2c | %IgG1 | %IgG2c | %IgG1 | %IgG2c |
| gB+pentamer | 0.03 | 0.00 | 0.10 | 0.05 | 0.43 | 0.03 |
| +MF59 | 4.29 | 0.34 | 0.99 | 0.09 | 1.33 | 0.12 |
| +PAA | 1.64 | 3.66 | 0.83 | 1.24 | 2.43 | 3.38 |
| +AF04 | 2.62 | 1.53 | 0.78 | 0.50 | 1.79 | 0.65 |
| +GLA-SQEM | 1.54 | 3.81 | 0.58 | 0.57 | 1.24 | 2.17 |

| B | day 34 | | day 208 | | day 257 | |
|---|---|---|---|---|---|---|
| Adjuvants | %IgG1 | %IgG2c | %IgG1 | %IgG2c | %IgG1 | %IgG2c |
| gB+pentamer | 0.04 | 0.00 | 0.33 | 0.03 | 0.55 | 0.06 |
| +MF59 | 4.68 | 0.75 | 1.88 | 0.08 | 1.91 | 0.18 |
| +PAA | 1.83 | 2.04 | 3.24 | 0.71 | 3.69 | 3.45 |
| +AF04 | 2.57 | 1.69 | 1.62 | 0.55 | 3.75 | 1.15 |
| +GLA-SQEM | 1.99 | 3.63 | 1.36 | 1.79 | 2.42 | 2.58 |

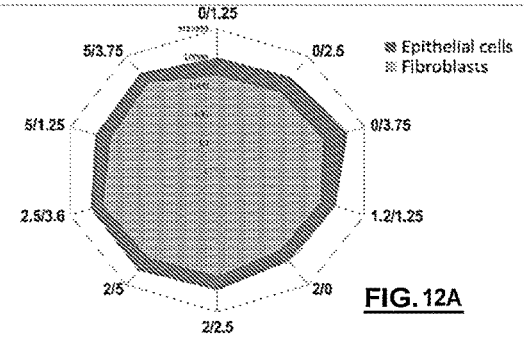
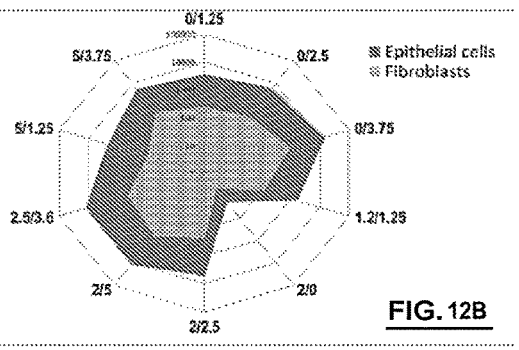
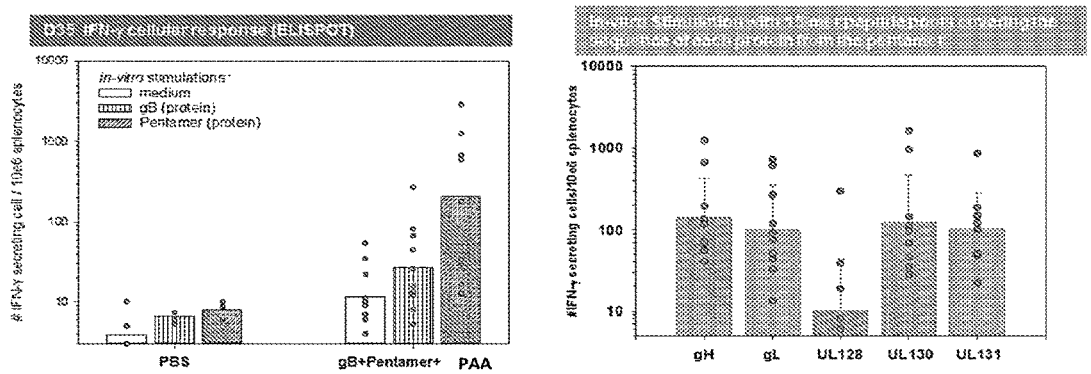
FIG. 13

HUMAN CYTOMEGALOVIRUS IMMUNOGENIC COMPOSITION

CROSS-REFERENCE TO RELATED APPLICATIONS

This application is a U.S. national stage application under 35 U.S.C. § 371 of International Application No. PCT/EP2018/074369, filed on Sep. 11, 2018, which claims priority to European Patent Application No. 17306179.7, filed on Sep. 13, 2017, the entire contents of each of which are incorporated herein by reference.

The invention relates to an immunogenic composition comprising an HCMV gB antigen, an HCMV gH/gL/UL128/UL130/UL131 pentameric complex antigen and a Th1-inducing adjuvant. It further relates to the immunogenic composition for use as an HCMV vaccine.

BACKGROUND OF THE INVENTION

The Human cytomegalovirus (HCMV) is a ubiquitous virus belonging to the Herpes virus family. The virus is composed of a linear double-stranded deoxyribonucleic acid (DNA) contained in a capsid surrounded by a tegument and enveloped in a lipid bilayer carrying glycoprotein spikes on its surface. Like other members of this family, HCMV possesses the characteristics of latency and reactivation. HCMV has the ability to infect and be latent in many cells.

In the immunocompetent host, most HCMV infections are asymptomatic or very mild with a few nonspecific symptoms such as fatigue, malaise, moderate fever, lymphadenopathy, hepatomegaly or a slight increase in liver enzymes. Heterophil-negative mononucleosis is however observed in approximately 10% of previously healthy individuals.

In contrast, clinical manifestations can be very severe in newborns infected in utero and in adults immunosuppressed by AIDS or in the context of solid organ or bone marrow transplantation.

The prevalence of HCMV infection increases with age and is affected by socioeconomic factors. Serological surveys have shown a higher prevalence in developing countries and in lower socioeconomic groups of developed countries. For women of child-bearing age, the proportion of HCMV seropositive women ranges from approximately 50% in upper and middle incomes groups of developed countries to over 80% in low-income populations. Surveys performed in different western European countries within the two last decades on the general population including different age-classes, females and males showed globally that HCMV seroprevalence in toddlers and adolescents ranges between 40 and 50% while in older subjects (40 years and over), HCMV seroprevalence is higher than 80%.

HCMV is shed for a prolonged period in the secretions of infected individuals including urine, saliva, milk, semen, genital secretions; HCMV is thus transmitted either horizontally (through intimate contact from child to child, from child to parents and between sex partners) or vertically from mother to fetus or infant through the placenta or at birth through body fluids contacts and breast feeding or by exposure to blood products or transplanted organs.

HCMV is the most common cause of congenital infection in the developed world. Congenital infection refers to infection transmitted from mother to fetus prior to birth of the newborn. Each year in the United States, an estimated 8000 infants suffer disabilities, including mental retardation, blindness and sensorineural deafness, as a result of congenital HCMV infection.

Among congenitally infected newborns, 5% to 10% have major manifestations at birth such as microcephaly, chorioretinitis, intracranial calcifications, hepatosplenomegaly, hepatitis, jaundice, direct hyperbilirubinemia, thrombocytopenia, petechiae, and anemia. Among these newborns with symptomatic congenital HCMV disease, the mortality rate is approximately 10% in early infancy and among survivors, 50-90% will have sequelae such as mental retardation, cerebral palsy, sensorineural hearing loss or visual impairment.

Many infants with congenital HCMV infection are asymptomatic at birth. Follow-up studies have shown that approximately 15% of infants who are asymptomatic at birth and identified as HCMV seropositive in the newborn period by virological screening will have sequelae such as hearing loss or central nervous system abnormalities.

As a whole, approximately 17,000 infants born each year in Europe and in the USA will have permanent sequelae.

Congenital HCMV infections are more frequent and more severe when the primary infection occurs in the first trimester of pregnancy than when primary infection occurs later in pregnancy. Overall, a primary HCMV infection during pregnancy is associated with a 40% risk of transmission to the fetus.

Effective means of preventing or treating maternal HCMV infection during pregnancy or congenital HCMV infection are currently not available.

HCMV is also an important viral pathogen in organ and bone marrow transplant recipients and in AIDS patients. The rate of HCMV-associated morbidity in HCMV seronegative solid organ transplant recipients approaches 60%. In solid organ transplant the disease is the most severe when seronegative patients receive a graft from a HCMV positive donor. In contrast, in bone marrow or stem cell transplantation the disease is most severe in HCMV seropositive subjects receiving cells from a seronegative donor showing that the origin of HCMV infection is reactivation of endogenous infection.

HCMV causes pneumonitis, hepatitis, gastrointestinal disease, bone marrow suppression, and retinitis in approximately 15% of allograft recipients. In addition to these direct end-organ diseases, HCMV has been associated with indirect effects such as graft rejection, accelerated atherosclerosis and immunosuppression that can lead to bacterial or fungal infection.

Development of an HCMV vaccine is therefore considered a major public health objective in Institute of Medicine vaccine prioritization reports (Kathleen R, Stratton, Jane S, Durch, Lawrence R S. Editors committee to study priorities for Vaccine Development Division of Health Promotion and Disease Prevention Institute of Medicine. In: Vaccines for the 21st century: A tool for decision making. Washington D.C.: National Academy Press; 2000). Many candidate vaccines have been described, but, so far, none has been licensed (Plotkin et al., Vaccines, $6^{th}$ edition, Ed. Elsevier, 2013, Schleiss et al., Cytomegalovirus vaccines, pages 1032-1041).

A cytomegalovirus glycoprotein-B vaccine with MF59 adjuvant showed promising results in a phase 2 randomised placebo-controlled trial in transplant recipients (Griffiths et al., Lancet, 2011, 377(9773):1256-63). A phase 2, placebo-controlled, randomized, double-blind trial in women of child-bearing age, evaluated the same vaccine consisting of recombinant HCMV envelope glycoprotein B with MF59 adjuvant, as compared with placebo. The results showed 50% efficacy in preventing HCMV acquisition of primary HCMV. However the immunogenicity results showed that the level of neutralizing antibodies (Ab) induced by the gB/MF59 formulation are at the peak level one month after the administration of the 3rd dose, and then rapidly decline (Pass et al., The New England Journal of Medecine, 2009, 360:1191-9).

As a consequence, there is a need to improve the HCMV vaccine efficacy, in particular to find a vaccine that increases neutralizing antibody levels and induces long-lasting protection by inducing persistent immune response. There is also a need to find a HCMV vaccine that more particularly induces a broader immune response.

DESCRIPTION OF THE INVENTION

Unexpectedly, the inventors of the present invention have now found a new immunogenic composition that complies with these requirements.

The present invention thus relates to an immunogenic composition comprising an HCMV gB antigen, an HCMV gH/gL/UL128/UL130/UL131 pentameric complex antigen and a Th1-inducing adjuvant.

In particular, said Th1-inducing adjuvant comprises:
a TLR-4 agonist; or
a polyacrylic acid polymer salt with a weight average molecular weight Mw in the range of 350 to 650 kDa.

In one embodiment, said Th1-inducing adjuvant comprises a TLR-4 agonist.

In particular, said TLR4 agonist is in combination with a delivery system such as aqueous nanosuspension, calcium phosphate, liposomes, virosomes, ISCOMs, micro- and nanoparticles, or emulsions.

More particularly, said delivery system is an oil-in-water emulsion.

In particular, said TLR-4 agonist is chosen from E6020 (CAS number: 287180-63-6) and a GLA (CAS Number 1246298-63-4) TLR-4 agonist.

In one embodiment, said Th1-inducing adjuvant comprises a linear or branched polyacrylic acid polymer salt with a weight average molecular weight Mw in the range of 350 to 650 kDa, in particular PAA225000.

In particular, said HCMV gB antigen comprises one or several mutations at the endoproteolytic cleavage site.

Still particularly, said HCMV gB antigen is a full length gB polypeptide, a full length gB polypeptide lacking at least a portion of the transmembrane domain, a full length gB polypeptide lacking substantially all the transmembrane domain, a full length gB polypeptide lacking at least a portion of the intracellular domain, a full length gB polypeptide lacking substantially all the intracellular domain, or a full length gB polypeptide lacking substantially both the transmembrane domain and the intracellular domain.

More particularly, said HCMV gB antigen is gBdTm.

In particular, in the said HCMV gH/gL/UL128/UL130/UL131 pentameric complex antigen, the gH antigen lacks at least a portion of the transmembrane domain, preferably the gH antigen lacks substantially all the transmembrane domain.

More particularly, said gH comprises the ectodomain of the full length gH encoded by UL75 gene.

Still particularly, in the immunogenic composition according to the invention, the HCMV gB and the HCMV gH/gL/UL128/UL130/UL131 pentameric complex are the sole HCMV antigens.

The present invention further relates to the immunogenic composition according to the invention for use as an HCMV vaccine.

In particular, said vaccine increases neutralizing antibody levels and/or persistence.

Immunogenic Composition

As previously mentioned, the immunogenic composition according to the invention comprises:
an HCMV gB antigen;
an HCMV gH/gL/UL128/UL130/UL131 pentameric complex antigen; and
a Th1-inducing adjuvant.

"HCMV" is used for Human cytomegalovirus and is any strain of Human cytomegalovirus.

The terms "comprising"/"comprises"/"comprise"/"comprised" encompass "including"/"includes"/"include"/"included" respectively as well as "consisting"/"consists"/"consist"/"consisted" respectively, e.g. a composition "comprising" X may consist exclusively of X or may include something additional, e.g. X+Y.

"Antigen" as used herein, has the common meaning known by a man skilled in the art. In particular, it refers to any molecule containing one or more epitopes (either linear, conformational or both), that elicits an immunological response.

In the context of the present invention, an antigen further includes a protein having modifications, such as deletions, additions and substitutions to the native sequence, as long as the protein maintains sufficient immunogenicity. These modifications may be deliberate, for example through site-directed mutagenesis, or may be accidental, such as mutations which occur during expression of the antigens in a host cell. The antigen may also be a protein or a fragment thereof encoded by a consensus sequence.

The antigen(s) which can be used in an immunogenic composition according to the invention are in particular an HCMV gB antigen and an HCMV gH/gL/UL128/UL130/UL131 pentameric complex antigen.

HCMV gB Antigen

The HCMV gB antigen according to the present invention is a full length gB polypeptide or a gB-derived polypeptide that induces neutralizing antibodies.

gB is encoded by the UL55 gene of HCMV genome. The size of the native form of gB (or gp130) depends on the size of the open reading frame (ORF), which may vary a little according to the strain. For example, the ORF of AD169 strain, which is 2717 bp long, encodes a full length gB of 906 amino acids whereas the ORF of Towne strain encodes a full length gB of 907 amino acids. The protein sequences of these two strains are described in US 2002/0102562 (FIG. 2), incorporated by reference in its entirety. The native form of gB contains an amino acid signal sequence that is normally 23 to 25 amino acid long, followed by an extracellular domain containing an endoproteolytic cleavage site between residues arginine 460 and serine 461, by a transmembrane domain and by an intracellular domain. Usually, the full length gB is depleted of the amino acid signal sequence as a consequence of posttranslational mechanisms that occur in cells. It will be well understood that suitable full length gB for the purpose of the invention encompasses both the full length gB of HCMV strains Towne and AD169, as well as other equivalent strains. Several antigenic domains inducing neutralizing antibodies have been described. Notably, it includes the domain that is located between amino acid residues 461 and 680 of gp 130, this domain being subdivided into two discontinuous domains, the domain between residues 461 and 619 and the domain between residues 620 and 680 (U.S. Pat. No. 5,547,834). It also includes the antigenic domain 1 (AD-1) located between amino acid residues 560 and 640 (Schoppel K. et al., Virology, 1996, 216:133-45) or the antigenic domain 2 (AD-2) located between amino acid residues 65 and 84 (Axelsson F et al., Vaccine, 2007, 26:41-6) or between amino acid residues 27 and 84 (Burke H G et al., PLoS pathogens, 2015, 11:e1005227). Consequently, a polypeptide that comprises in its amino acid sequence a sequence homologous to one or several of the above cited antigenic domains is also suitable for the purpose of the invention. The term "a sequence homologous to" is intended to mean an amino acid sequence in which there is at least 80% identity with the amino acid sequence of the antigenic domain being considered of the native gB originating from the Towne or AD169 strain (which are described in US 2002/0102562). Typically, the sequence homology is based on a sequence identity of at least 90% and, even more specifically, the sequence homology is complete (sequence identity of 100%).

As used herein, a first sequence having at least x % identity with a second sequence means that x % represents the number of amino acids in the first sequence which are identical to their matched amino acids of the second sequence when both sequences are optimally aligned via a global alignment, relative to the total length of the second amino acid sequence. Both sequences are optimally aligned when x is maximum. The alignment and the determination of the percentage of identity may be carried out manually or automatically using a global alignment algorithm, for instance the Needleman and Wunsch algorithm, described in Needleman and Wunsch, J. Mol Biol., 48, 443-453 (1970), with for example the following parameters for polypeptide sequence comparison: comparison matrix: BLOSUM62 from Henikoff and Henikoff, Proc. Natl. Acad. Sci. USA., 89, 10915-10919 (1992), gap penalty: 8 and gap length penalty: 2; and the following parameters for polynucleotide sequence comparison: comparison matrix: matches=+10, mismatch=0; gap penalty: 50 and gap length penalty: 3.

A program which may be used with the above parameters is publicly available as the "gap" program from Genetics Computer Group, Madison Wis. The aforementioned parameters are the default parameters respectively for peptide comparisons (along with no penalty for end gaps) and for nucleic acid comparisons.

Among the gB-derived peptides or polypeptides that are suitable for the object of the invention is gp 55 as described in U.S. Pat. No. 5,547,834. It is derived from the cleavage of gB at the endoproteolytic cleavage site; its amino acid sequence corresponds to that which is between serine residue 461 and the C-terminal end. Truncated forms of gp 55 can also be used, such as a gp 55 depleted of all or part of the transmembrane sequence and of all or part of the intracellular C-terminal domain (for example, a peptide having a sequence homologous to the amino acid sequence of the native gB between residues 461 and 646) or a gp 55 depleted of all or part of the intracellular C-terminal domain (for example, a peptide having a sequence homologous to the amino acid sequence of the native gB between residues 461 and 680). Such truncated forms of gp 55 are also described in U.S. Pat. No. 5,547,834, incorporated by reference in its entirety.

It is also possible to use a mutated form of the full length gB that carries one or several mutations at the endoproteolytic cleavage site such that the latter is made ineffectual. In particular, the mutation(s) is (are) located between residues 457 and 460 of the sequence of gp130 and, more particularly, are located at arginine 460 and/or lysine 459 and/or arginine 457. In this aspect, the mutated form of the full length gB carries the entire extracellular domain with all the domains that are targets for neutralizing antibodies. Such mutated forms can be secondarily depleted of all or part of the transmembrane sequence and/or of all or part of the intracellular C-terminal domain in order to allow their secretion in the host when produced as recombinant proteins and their easy downstream purification. Such gB-derivatives are preferred in so far as substantially all the domains that are targets for neutralizing antibodies are conserved.

Therefore, in one aspect of the invention the HCMV gB comprises one or several mutations on the endoproteolytic cleavage site, and in particular the HCMV gB is in addition selected from among the group of a full length HCMV gB, a full length HCMV gB lacking at least a portion of the transmembrane domain, a full length gB polypeptide lacking substantially all the transmembrane domain, a full length gB polypeptide lacking at least a portion of the intracellular domain, a full length HCMV gB lacking substantially all the intracellular domain, and a full length HCMV gB polypeptide lacking substantially both the transmembrane domain and the intracellular domain.

The expression "lacking substantially all the intracellular domain" or "lacking substantially all the transmembrane domain" means that at least 80% of the amino acid sequence corresponding to the said domain is deleted.

In the context of the present invention, by "lacking at least a portion of a domain", is meant lacking at least 10%, at least 20%, at least 30%, at least 40%, at least 50%, at least 60% or at least 70% but lacking less than 80% of the domain.

In one embodiment, the HCMV gB antigen is the ectodomain of gB, i.e. a full length gB depleted of all the transmembrane sequence and of all the intracellular C-terminal domain. The "ectodomain" is the portion of a transmembrane anchored protein that extends beyond the membrane into the extracellular space.

The HCMV gB antigen according to the present invention may also contain other mutations and/or deletions and/or additions. For instance, the HCMV gB antigen may contain at least one amino acid deletion or substitution in at least one of the fusion loop 1 (FL1) domain and fusion loop 2 (FL2) domain located in the extracellular domain as described in EP2627352. Alternatively or in addition, it may contain a deletion of at least a portion of the leader sequence as described in EP2627352. The HCMV gB antigen according to the present invention may also comprise a mutation that results in a glycosylation site within hydrophobic surface 1 (amino acid residues 154-160 and 236-243) as described in WO2016092460. In particular, said glycosylation site is an N-glycosylation site comprising an N—X—S/T/C motif, wherein X is any amino acid residue (but preferably not proline). The HCMV gB antigen may comprise a mutation that results in a glycosylation site, wherein said glycosylation site is (1) within hydrophobic surface 2 (amino acid residues 145-167 and 230-252); or (2) at a residue that is within 20 angstroms from fusion loop 1 (FL1) (amino acid residues 155-157) and/or fusion loop 2 (FL2) (amino acid residues 240-242), as described in WO2016092460. The HCMV gB antigen may comprise a heterologous sequence that is at least 12 residues long at the C-terminus as described in WO2016092460. In particular, the gB protein may be a fusion protein wherein the heterologous sequence is fused at the C-terminus of the ectodomain.

Native HCMV gB has been postulated to be a homotrimer based on the 3D crystallography structure of gB proteins in related viruses, Herpes Simplex Virus 1 (HSV-1) gB and Epstein Barr Virus (EBV) gB, which are homotrimers (Heldwein et al., Science, 2006, 313:217-220; Backovic et al., PNAS, 2009, 106(8):2880-2885). The HCMV gB antigen according to the present invention may be in a trimeric (native form), and/or hexameric (dimer of the trimeric native form), and/or dodecameric (dimer of hexamer) form. In particular, the HCMV gB antigen part of the immunogenic composition according to the present invention is substantially not in a monomeric form, more particularly not in a monomeric form. The expression "is substantially not in a monomeric form" means that less than 20%, in particular less than 10%, in particular less than 5%, of the HCMV gB antigen is in a monomeric form.

According to an embodiment, the gB antigen comprises an amino acid sequence which has at least 80% identity with SEQ ID NO: 1. In particular, said gB antigen comprises an amino acid sequence which has at least 85% identity, at least 90% identity, at least 95% identity, at least 97% identity, at least 98% identity, at least 99% identity or even 100% identity with SEQ ID NO: 1:

SSTRGTSATHSHHSSHTTSAAHSRSGSVSQRVTSSQTVSHGVNETIYNTT

LKYGDVVGVNTTKYPYRVCSMAQGTDLIRFERNIVCTSMKPINEDLDEGI

MVVYKRNIVAHTFKVRVYQKVLTFRRSYAYIHTTYLLGSNTEYVAPPMWE

IHHINSHSQCYSSYSRVIAGTVFVAYHRDSYENKTMQLMPDDYSNTHSTR

YVTVKDQWHSRGSTWLYRETCNLNCMVTITTARSKYPYHFFATSTGDVVD

ISPFYNGTNRNASYFGENADKFFIFPNYTIVSDFGRPNSALETHRLVAFL

ERADSVISWDIQDEKNVTCQLTFWEASERTIRSEAEDSYHFSSAKMTATF

LSKKQEVNMSDSALDCVRDEAINKLQQIFNTSYNQTYEKYGNVSVFETTG

GLVVFWQGIKQKSLVELERLANRSSLNLTHNTTQTSTDGNNATHLSNMES

VHNLVYAQLQFTYDTLRGYINRALAQIAEAWCVDQRRTLEVFKELSKINP

SAILSAIYNKPIAARFMGDVLGLASCVTINQTSVKVLRDMNVKESPGRCY

SRPVVIFNFANSSYVQYGQLGEDNEILLGNHRTEECQLPSLKIFIAGNSA

YEYVDYLFKRMIDLSSISTVDSMIALDIDPLENTDFRVLELYSQKELRSS

NVFDLEEIMREFNSYKQRVKYVEDKRLCMQPLQNLFPYLVSADGTTVTSG

NTKDTSLQAPPSYEESVYNSGRKGPGPPSSDASTAAPPYTNEQAYQMLLA

LVRLDAEQRAQQNGTDSLDGQTGTQDKGQKPNLLDRLRHRKNGYRHLKDS

DEEENV.

In a preferred embodiment the gB antigen comprises an amino acid sequence which has 100% identity with SEQ ID NO: 1.

Figures 10, 11:
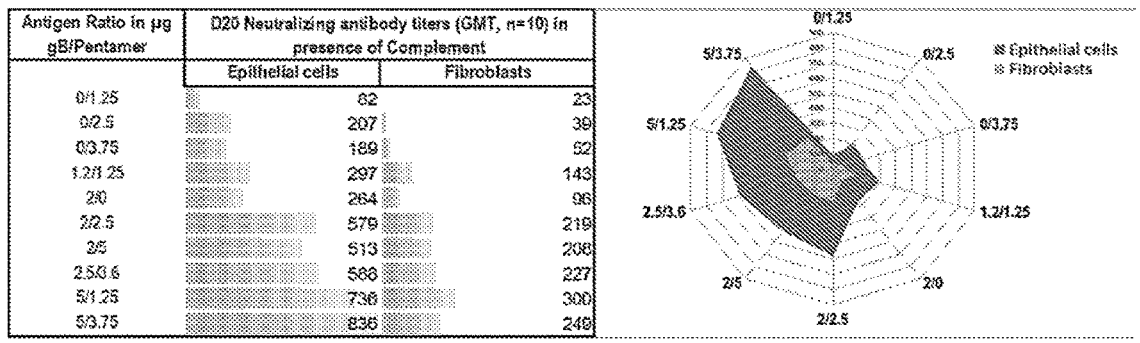

An HCMV gB antigen that is particularly suitable in the context of the present invention is a truncated form of the full length gB depleted of all or part of the C-terminal domain and/or depleted of all or part of the transmembrane sequence and in which the cleavage site is ineffectual. A truncated form of gB that is particularly preferred corresponds to that which is described in U.S. Pat. No. 6,100,064, called gBdTM, incorporated by reference in its entirety. In U.S. Pat. No. 6,100,064 the signal sequence was hypothetized as 24 amino acids long and the amino acid positions were indicated accordingly on FIG. 10. The inventors have discovered that this signal sequence is in fact 25 amino acids long. In FIG. 10 of U.S. Pat. No. 6,100,064 all the amino acid positions indicated C-terminal of the Ser-1 (i.e. C-terminal to the signal sequence) have so to be decreased from 1. Accordingly gBdTM carries three mutations at the cleavage site (Arginine 432 is substituted by Threonine, Lysine 434 is substituted by Glutamine and Arginine 435 is substituted by Threonine; taking into account the renumbered positions) and a deletion in the transmembrane region between amino acid residues valine 676 and arginine 751 (taking into account the renumbered positions), such that the extracellular domain is directly connected to the cytoplasmic domain. Such gB-derived polypeptide is easier to purify as it is produced by recombinant cells expressing this product under a secreted form. The resulting form is an 806 amino acid long polypeptide deleted of its signal sequence and of its transmembrane region when it is derived from the gB Towne strain.

The HCMV gB protein described herein or the peptides or polypeptides derived therefrom may be synthesized by any method well-known to the man skilled in the art. Such methods include conventional chemical synthesis, in solid phase (R. B. Merrifield, J. Am. Chem. Soc., 85 (14), 2149-2154 (1963)), or in liquid phase, enzymatic synthesis (K. Morihara, Trends in Biotechnology, 5(6), 164-170 (1987)) from constitutive amino acids or derivatives thereof, cell-free protein synthesis (Katzen et al., Trends in Biotechnology, 23(3), 150-156 (2005)), as well as biological production methods by recombinant technology.

For example, the HCMV gB antigen can be obtained using a biological production process with a recombinant host cell. In such a process, an expression cassette, containing a nucleic acid encoding an HCMV gB antigen as described herein, is transferred into a host cell, which is cultured in conditions enabling expression of the corresponding protein. The protein thereby produced can then be recovered and purified. Methods for the purification of proteins are well-known to the skilled person. The obtained recombinant protein can be purified from lysates and cell extracts or from the culture medium supernatant, by methods used individually or in combination, such as fractionation, chromatographic methods, immunoaffinity methods using specific mono- or polyclonal antibodies, etc. In particular, the obtained recombinant protein is purified from the culture medium supernatant.

The HCMV gB protein or the peptides or polypeptides derived therefrom are usually obtained by recombinant DNA techniques and purified according to methods well known to those skilled in the art. The methods described in U.S. Pat. No. 6,100,064 and in US 2002/0102562, incorporated by reference in their entirety, can in particular be used.

For example, the gB antigen according to the invention is a recombinant glycoprotein, which is produced in Chinese hamster ovary (CHO) cell cultures. The gB gene from the Towne strain of HCMV can be mutagenized to remove the cleavage site and the transmembrane portion of the molecule in order to facilitate secretion in cell culture as described in U.S. Pat. No. 6,100,064. The secreted molecule is a polypeptide of 806 amino acids, retaining 19 potential N-linked glycosylation sites, and is also called gBdTm. The purification process involved affinity and ion-exchange chromatography steps.

HCMV gH/gL/UL128/UL130/UL131 Pentameric Complex Antigen

Another antigen part of the immunogenic composition according to the invention is the HCMV gH/gL/UL128/UL130/UL131 pentameric complex antigen.

Said pentameric complex is assembled through disulfide bonds and non-covalent interactions among the five components to form a functional complex able to present conformational epitopes (Ciferri et al., PNAS, 2015, 112(6): 1767-1772; Wen et al., Vaccine, 2014, 32(30):3796-3804).

Said complex has already been described and is known by the man skilled in the art. It is in particular described in Ryckman et al. (Journal of Virology, January 2008, p. 60-70) and in patent application WO2014/005959. Said HCMV gH/gL/UL128/UL130/UL131 pentameric complex can in particular comprise a modified HCMV gH polypeptide, wherein said polypeptide lacks at least a portion of the transmembrane (TM) domain. In some embodiments, the gH polypeptide can retain a portion of the natural TM domain, but not enough to let the protein stay in a lipid bilayer. In a preferred embodiment the gH polypeptide lacks substantially all the transmembrane domain. In a more preferred embodiment the gH polypeptide lacks the full-length natural TM domain.

Thus, the gH polypeptide can contain up to 10 amino acids (e.g. 1, 2, 3, 4, 5, 6, 7, 8, 9 or 10 amino acids) of the natural gH TM domain.

In the context of the present invention, by "lacking at least a portion of a domain", is meant lacking at least 10%, at least 20%, at least 30%, at least 40%, at least 50%, at least 60% or at least 70% but lacking less than 80% of the domain.

The expression "lacking substantially all the intracellular domain" or "lacking substantially all the transmembrane domain" means that at least 80% of the amino acid sequence corresponding to the said domain is deleted.

Alternatively or in addition to lacking a portion or all of the TM domain, the polypeptide may lack a portion or substantially all or all the intracellular domain of HCMV gH.

In a preferred embodiment the gH polypeptide lacks substantially all the intracellular domain. In a more preferred embodiment the gH polypeptide lacks the full-length natural intracellular domain.

In a preferred embodiment, the gH polypeptide lacks all the TM domain and all the intracellular domain.

In one embodiment, said gH comprises the ectodomain of the full length gH encoded by UL75 gene.

HCMV glycoprotein H (gH), which is encoded by the UL75 gene, is a virion glycoprotein that is essential for infectivity and which is conserved among members of the alpha-, beta- and gamma-herpes viruses. It forms a stable complex with gL, and the formation of this complex facilitates the cell surface expression of gH. Based on the crystal structures of HSV-2 and EBV gH/gL complexes, the gL subunit and N-terminal residues of gH form a globular domain at one end of the structure (the 'head'), which is implicated in interactions with gB and activation of membrane fusion. The C-terminal domain of gH, proximal to the viral membrane (the 'tail'), is also implicated in membrane fusion. In one embodiment, the gH polypeptide in the pentameric complex described herein comprises an amino acid sequence which has at least 80% identity with SEQ ID NO: 2. In particular, the gH antigen comprises an amino acid sequence which has at least 85% identity, at least 90% identity, at least 95% identity, at least 97% identity, at least 98% identity, at least 99% identity or even 100% identity with SEQ ID NO: 2:

RYGAEAVSEPLDKAFHLLLNTYGRPIRFLRENTTQCTYNNSLRNSTVVRE

NAISFNFFQSYNQYYVFHMPRCLFAGPLAEQFLNQVDLTETLERYQQRLN

TYALVSKDLASYRSFSQQLKAQDSLGEQPTTVPPPIDLSIPHVWMPPQTT

PHGWTESHTTSGLHRPHFNQTCILFDGHDLLFSTVTPCLHQGFYLIDELR

YVKITLTEDFFVVTVSIDDDTPMLLIFGHLPRVLFKAPYQRDNFILRQTE

KHELLVLVKKDQLNRHSYLKDPDFLDAALDFNYLDLSALLRNSFHRYAVD

-continued

VLKSGRCQMLDRRTVEMAFAYALALFAAARQEEAGAQVSVPRALDRQAAL

LQIQEFMITCLSQTPPRTTLLLYPTAVDLAKRALWTPNQITDITSLVRLV

YILSKQNQQHLIPQWALRQIADFALKLHKTHLASFLSAFARQELYLMGSL

VHSMLVHTTERREIFIVETGLCSLAELSHFTQLLAHPHHEYLSDLYTPCS

SSGRRDHSLERLTRLFPDATVPATVPAALSILSTMQPSTLETFPDLFCLP

LGESFSALTVSEHVSYVVTNQYLIKGISYPVSTTVVGQSLIITQTDSQTK

CELTRNMHTTHSITAALNISLENCAFCQSALLEYDDTQGVINIMYMHDSD

DVLFALDPYNEVVVSSPRTHYLMLLKNGTVLEVTDVVVDATDSR.

In a preferred embodiment the gH polypeptide comprises an amino acid sequence which has 100% identity with SEQ ID NO: 2.

HCMV glycoprotein L (gL) is encoded by the UL115 gene. gL is thought to be essential for viral replication and all known functional properties of gL are directly associated with its dimerization with gH. The gL/gH complex is required for the fusion of viral and plasma membranes leading to virus entry into the host cell.

According to one embodiment, the gL polypeptide in the pentameric complex described herein comprises an amino acid sequence which has at least 80% identity with SEQ ID NO: 3. In particular, the gL antigen comprises an amino acid sequence which has at least 85% identity, at least 90% identity, at least 95% identity, at least 97% identity, at least 98% identity, at least 99% identity or even 100% identity with SEQ ID NO: 3:

AAVSVAPTAAEKVPAECPELTRRCLLGEVFQGDKYESWLRPLVNVTGRDG

PLSQLIRYRPVTPEAANSVLLDEAFLDTLALLYNNPDQLRALLTLLSSDT

APRWMTVMRGYSECGDGSPAVYTCVDDLCRGYDLTRLSYERSIFTEHVLG

FELVPPSLFNVVVAIRNEATRTNRAVRLPVSTAAAPEGITLFYGLYNAVK

EFCLRHQLDPPLLRHLDKYYAGLPPELKQTRVNLPAHSRYGPQAVDAR.

In a preferred embodiment the gL polypeptide comprises an amino acid sequence which has 100% identity with SEQ ID NO: 3.

According to an embodiment, the UL128 polypeptide in the pentameric complex described herein comprises an amino acid sequence which has at least 80% identity with SEQ ID NO: 4. In particular, the UL128 antigen comprises an amino acid sequence which has at least 85% identity, at least 90% identity, at least 95% identity, at least 97% identity, at least 98% identity, at least 99% identity or even 100% identity with SEQ ID NO: 4:

EECCEFINVNHPPERCYDFKMCNRFTVALRCPDGEVCYSPEKTAEIRGIV

TTMTHSLTRQVVHNKLTSCNYNPLYLEADGRIRCGKVNDKAQYLLGAAGS

VPYRWINLEYDKITRIVGLDQYLESVKKHKRLDVCRAKMGYMLQ.

In a preferred embodiment the UL128 polypeptide comprises an amino acid sequence which has 100% identity with SEQ ID NO: 4.

UL130 is the central and the largest (214 codons) gene of the UL131A-128 locus. Conceptual translation of the gene predicts a long (25 amino acids) N-terminal signal sequence that precedes a hydrophilic protein containing two potential N-linked glycosylation sites (Asn85 and Asn118) within a putative chemokine domain (amino acids 46 to 120) and an additional N-glycosylation site (Asn201) close to the end of a unique C-terminal region. UL130 is predicted to lack a TM domain.

It has been reported to be a luminal glycoprotein that is inefficiently secreted from infected cells but is incorporated into the virion envelope as a Golgi-matured form (Patrone, et al.: "Human Cytomegalovirus UL130 Protein Promotes Endothelial Cell Infection through a Producer Cell Modification of the Virion.", Journal of Virology 79 (2005): 8361-8373).

According to an embodiment, the UL130 polypeptide in the pentameric complex described herein comprises an amino acid sequence which has at least 80% identity with SEQ ID NO: 5. In particular, the UL130 antigen comprises an amino acid sequence which has at least 85% identity, at least 90% identity, at least 95% identity, at least 97% identity, at least 98% identity, at least 99% identity or even 100% identity with SEQ ID NO: 5:

SPWSTLTANQNPSPLWSKLTYSKPHDAATFYCPFIYPSPPRSPLQFSGFQ

RVLTGPECRNETLYLLYNREGQTLVERSSTWVKKVIWYLSGRNQTILQRM

PRTASKPSDGNVQISVEDAKIFGAHMVPKQTKLLRFVVNDGTRYQMCVMK

LESWAHVFRDYSVSFQVRLTFTEANNQTYTFCTHPNLIV.

In a preferred embodiment the UL130 polypeptide comprises an amino acid sequence which has 100% identity with SEQ ID NO: 5.

UL131, also called UL131A, function is required for HCMV replication not only in endothelial cells but also in epithelial cells. According to an embodiment, the UL131A polypeptide in the pentameric complex described herein comprises an amino acid sequence which has at least 80% identity with SEQ ID NO: 6. In particular, the UL131A antigen comprises an amino acid sequence which has at least 85% identity, at least 90% identity, at least 95% identity, at least 97% identity, at least 98% identity, at least 99% identity or even 100% identity with SEQ ID NO: 6:

QCQRETAEKNDYYRVPHYWDACSRALPDQTRYKYVEQLVDLTLNYHYDAS

HGLDNFDVLKRINVTEVSLLISDFRRQNRRGGTNKRTTFNAAGSLAPHAR

SLEFSVRLFAN.

In a preferred embodiment the UL131 polypeptide comprises an amino acid sequence which has 100% identity with SEQ ID NO: 6.

SEQ ID NO: 2 to 6 are from the strain BE/28/2011 (Genbank ID KP745669, Kremkow et al., 2015).

In the pentameric complex antigen part of the immunogenic composition of the invention, gH, gL and UL128 can be linked through disulfide bonds, but UL130 and UL131A can be incorporated into the pentameric complex by non-covalent interactions. For example, the UL130 protein and/or UL131A protein is incorporated into the pentameric complex by non-covalent interactions. Furthermore, the UL130 protein and/or UL131A protein may be inter-linked by non-covalent interactions.

A range of conformational epitopes for the pentameric complex are known. For example, Macagno (Macagno et al.: "Isolation of human monoclonal antibodies that potently neutralize human cytomegalovirus infection by targeting different epitopes on the gH/gL/UL128-131A complex.", Journal of Virology 84 (2010): 1005-13) isolated a panel of human monoclonal antibodies that neutralized HCMV infection of endothelial, epithelial, and myeloid cells. In one embodiment, the pentameric complex antigen part of the immunogenic composition of the invention possesses one or more of the conformational epitopes identified by Macagno (2010).

Each protein of the pentameric complex antigen may contain mutations, such as insertions, deletions and substitutions, so long as these mutations are not detrimental to the use of the proteins as antigens. In addition, such mutations should not prevent the capacity of the proteins to form a pentameric complex according to the invention. The ability to form a pentameric complex of the invention can be tested by performing protein purification, and analyzing the proteins by non-reducing PAGE, Western blot and/or size exclusion chromatography. If the proteins form part of a complex, they may all be present in a single band on a native PAGE gel and/or be present in a single peak in a size exclusion chromatogram.

Expression of said pentameric complex can be realized according to methods known by the man skilled in the art. Mention can be made for example of the method described in Hofmann et al. (Biotechnology and Bioengineering, 2015).

Suitable expression systems for use in the context of the present invention are well known to the man skilled in the art and many are described in detail in Doyle (Doyle, ed. High Throughput Protein Expression and Purification: Methods and Protocols (Methods in Molecular Biology). Humana Press, 2008). Generally, any system or vector that is suitable to maintain, propagate and express nucleic acid molecules to produce a polypeptide in the required host may be used. The appropriate nucleotide sequence may be inserted into an expression system by any of a variety of well-known and routine techniques, such as, for example, those described in Sambrook (Sambrook, J. Molecular Cloning: A Laboratory Manual. 3rd. Cold Spring Harbor Laboratory Press, 2000). Generally, the encoding gene can be placed under the control of a control element such as a promoter, and, optionally, an operator, so that the DNA sequence encoding the desired peptide is transcribed into RNA in the transformed host cell. Examples of suitable expression systems include, for example, chromosomal, episomal and virus-derived systems, including, for example, vectors derived from: bacterial plasmids, bacteriophage, transposons, yeast episomes, insertion elements, yeast chromosomal elements, viruses such as baculoviruses such as described in patent application WO2015170287, papova viruses such as SV40, vaccinia viruses, adenoviruses, fowl pox viruses, pseudorabies viruses and retroviruses, or combinations thereof, such as those derived from plasmid and bacteriophage genetic elements, including cosmids and phagemids. Human artificial chromosomes (HACs) may also be employed to deliver larger fragments of DNA than can be contained and expressed in a plasmid.

In order to express the five different recombinant proteins of the HCMV gH/gL/UL128/UL130/UL131 pentameric complex antigen simultaneously and in an equimolar way, there are several possibilities. A first possibility (1) for the HCMV gH/gL/UL128/UL130/UL131 pentameric complex antigen part of the immunogenic composition of the present invention is to build a single vector containing all five ORFs under the control of the same or similar regulations elements (promoter, enhancer, splice signal, termination signal . . . ) and optionally a selection system for cell line selection. The vector could contain five expression cassettes (for instance as described in Albers et al., J. Clin. Invest., 2015, 125(4):

1603-1619; or in Cheshenko et al., Gene Ther., 2001, 8(11): 846-854), or the five components (gH, gL, UL128, UL130 and UL131) could be fused in a single ORF with elements triggering the proper polyprotein maturation into the five proteins of the HCMV gH/gL/UL128/UL130/UL131 pentameric complex antigen (for instance self-cleavable sequences as described in Szymczak-Workman et al., Cold Spring Harb. Protoc., 2012, 2012 (2): 199-204). In that second case, the equimolarity is guaranteed, assuming all cleavage occur correctly. Another possibility (2) for the HCMV gH/gL/UL128/UL130/UL131 pentameric complex antigen part of the immunogenic composition of the present invention is to build five vectors each expressing one component of the HCMV gH/gL/UL128/UL130/UL131 pentameric complex antigen and optionally a selection system for cell line selection. The five vectors are co-transfected in the target cell line. Any intermediate system between possibility (1) and possibility (2) could also be designed to minimize the number of vectors required and maintain each vector to a reasonable size (less than 12 kb, for example).

Suitable expression systems include microorganisms such as bacteria transformed with recombinant bacteriophage, plasmid or cosmid DNA expression vectors; yeast transformed with yeast expression vectors; insect cell systems infected or transfected with virus expression vectors (for example, baculovirus such as described in patent application WO2015170287); plant cell systems transformed with virus expression vectors (for example, cauliflower mosaic virus, CaMV; tobacco mosaic virus, TMV) or with bacterial expression vectors (for example, Ti or pBR322 plasmids); or animal cell systems. Cell-free translation systems can also be employed to produce the proteins.

Examples of suitable plant cellular genetic expression systems include those described in U.S. Pat. Nos. 5,693,506; 5,659,122; 5,608,143 and Zenk (1991). "Chasing the enzymes of secondary metabolism: Plant cell cultures as a pot of goal. Phytochemistry, 30(12), pp 3861-3863. Zess NaukUMK Tornu, 13: 253-256. In particular, all plants from which protoplasts can be isolated and cultured to give whole regenerated plants can be used, so that whole plants are recovered which contain the transferred gene. Practically all plants can be regenerated from cultured cells or tissues, including but not limited to all major species of sugar cane, sugar beet, cotton, fruit and other trees, legumes and vegetables.

HEK293 cells are suitable for transient expression of the HCMV proteins of the pentamer complex according to the invention due to their high transfectability by various techniques, including the calcium phosphate and polyethylenimine (PEI) methods. A useful cell line of HEK293 is one that expresses the EBNA1 protein of EBV, such as 293-6E (Loignon, et al.: "Stable high volumetric production of glycosylated human recombinant IFNalpha2b in HEK293 cells.", BMC Biotechnology 8 (2008): 65). Transformed HEK293 cells have been shown to secrete high levels of the protein into the growth medium, thus allowing the purification of such protein complexes directly from the growth medium.

CHO cells are particularly suitable mammalian hosts for industrial production of the HCMV proteins and in particular for industrial production of the HCMV gH/gL/UL128/UL130/UL131 pentameric complex antigen part of the immunogenic composition according to the invention.

Transfection can be carried out by a range of methods well known in the art including using calcium phosphate, electroporation, or by mixing a cationic lipid with the material to produce liposomes which fuse with the cell membrane and deposit their cargo inside.

Methods for purifying recombinant proteins from cell supernatant or from inclusion bodies are well known in the art. In particular the HCMV gH/gL/UL128/UL130/UL131 pentameric complex antigen part of the immunogenic composition according to the invention may be purified by size-exclusion chromatography.

In particular, the immunogenic composition according to the invention does not comprise an HCMV virus.

In particular, the immunogenic composition according to the invention is an immunogenic composition as described herein, wherein the HCMV gB and the HCMV gH/gL/UL128/UL130/UL131 pentameric complex are the sole HCMV antigens.

Th1-Inducing Adjuvant

"Adjuvant" as used herein, has the meaning commonly known by a man skilled in the art. In particular, it refers to agents or substances that modulate the immunogenicity of an antigen. "Modulate the immunogenicity" includes enhancing the magnitude and/or duration of an immune response generated by an antigen. More specifically the adjuvants can also be classified according to the type of immune response they induce in the presence of the antigen. The adjuvant(s) which can be used in an immunogenic composition according to the invention are Th1-inducing adjuvants.

A "Th1-inducing" adjuvant can be defined as an adjuvant which enhances the Th1 response to an antigen or a combination of antigens.

An immune response may be broadly divided into two extreme categories, being a humoral or cell mediated immune response (traditionally characterized by antibody and cellular effector mechanisms of protection respectively). These categories of response have been termed Th1-type responses (cell-mediated response), and Th2-type immune responses (humoral response). In mice, Th1-type responses are often characterized by the generation of antibodies of the IgG2a or IgG2c subtype (depending on the mouse strain), whilst in humans these may correspond to IgG1 and IgG3 type antibodies. Th2-type immune responses are characterized by the generation of a broad range of immunoglobulin isotypes including in mice IgG1, IgA, and IgM. Th1-type and Th2-type immune responses are also characterized by different patterns of cytokine secretion (Mosmann et al., Annual Review of Immunology, 1989, 7: 145-173; Constant et al., Annual Review of Immunology, 1997, 15: 297-322). A Th1-type immune response is associated with an increased production of IFN-γ and/or IL-2 cytokines by T-lymphocytes while a Th-2 type immune response is associated with an increased production of IL-4, IL-5, IL-6, IL-13, and/or IL-10 cytokines. The distinction of Th1 and Th2-type immune responses is not absolute. In reality, a subject will support an immune response which is described as being predominantly Th1 or predominantly Th2. Traditionally the best indicators of the Th1:Th2 balance of the immune response after a vaccination or infection include direct measurement of the production of Th1 or Th2 cytokines by T lymphocytes in vitro upon stimulation with antigen, and/or the measurement (at least in mice) of the IgG1:IgG2a,c ratio of antigen specific antibody responses.

Also, in the scope of the immunogenic composition according to the invention, an adjuvant that induces predominantly a Th1-type immune response is considered as a Th1-inducing adjuvant. Preferentially the adjuvant(s) which can be used in an immunogenic composition according to the invention induce predominantly a Th1-type immune response.

As previously mentioned, this can be determined by measurement of the IgG1:IgG2a,c ratio in mice. An increase of INF-y is an additional indicator of predominant Th1 response. Preferably, a decreased production of IL-5 is also observed.

Preferably, the Th1-inducing adjuvants which can be used in the immunogenic composition according to the invention comprising an HCMV gB antigen and an HCMV gH/gL/UL128/UL130/UL131 pentameric complex antigen induce a more Th1-biased response profile than MF59 in a composition comprising the same HCMV gB antigen and the same HCMV gH/gL/UL128/UL130/UL131 pentameric complex antigen.

MF59 is a squalene-based oil-in-water emulsion described in patent application WO90/14837, U.S. Pat. Nos. 6,299,884 and 6,451,325, and in Ott et al., "MF59—Design and Evaluation of a Safe and Potent Adjuvant for Human Vaccines" in Vaccine Design: The Subunit and Adjuvant Approach (Powell, M. F. and Newman, M. J. eds.) Plenum Press, New York, 1995, pp. 277-296).

In particular, the Th1-inducing adjuvants which can be used in the immunogenic composition according to the invention comprising an HCMV gB antigen and an HCMV gH/gL/UL128/UL130/UL131 pentameric complex antigen induce a lower IgG1:IgG2a,c ratio in mice than MF59 in a composition comprising the same HCMV gB antigen and the same HCMV gH/gL/UL128/UL130/UL131 pentameric complex antigen.

More particularly, the Th1-inducing adjuvants which can be used in the immunogenic composition according to the invention comprising an HCMV gB antigen and an HCMV gH/gL/UL128/UL130/UL131 pentameric complex antigen induce a higher INF-y level in mice than MF59 in a composition comprising the same HCMV gB antigen and the same HCMV gH/gL/UL128/UL130/UL131 pentameric complex antigen.

Even more particularly, the Th1-inducing adjuvants which can be used in the immunogenic composition according to the invention comprising an HCMV gB antigen and an HCMV gH/gL/UL128/UL130/UL131 pentameric complex antigen induce a lower IL-5 level in mice than MF59 in a composition comprising the same HCMV gB antigen and the same HCMV gH/gL/UL128/UL130/UL131 pentameric complex antigen.

Still even more particularly, the Th1-inducing adjuvants which can be used in the immunogenic composition according to the invention comprising an HCMV gB antigen and an HCMV gH/gL/UL128/UL130/UL131 pentameric complex antigen induce a lower IgG1:IgG2a,c ratio and a higher INF-y level in mice than MF59 in a composition comprising the same HCMV gB antigen and the same HCMV gH/gL/UL128/UL130/UL131 pentameric complex antigen.

In particular, the Th1-inducing adjuvants which can be used in the immunogenic composition according to the invention comprising an HCMV gB antigen and an HCMV gH/gL/UL128/UL130/UL131 pentameric complex antigen induce a lower IgG1:IgG2a,c ratio and a lower IL-5 level in mice than MF59 in a composition comprising the same HCMV gB antigen and the same HCMV gH/gL/UL128/UL130/UL131 pentameric complex antigen.

More particularly, the Th1-inducing adjuvants which can be used in the immunogenic composition according to the invention comprising an HCMV gB antigen and an HCMV gH/gL/UL128/UL130/UL131 pentameric complex antigen induce a lower IgG1:IgG2a,c ratio, a higher INF-y level and a lower IL-5 level in mice than MF59 in a composition comprising the same HCMV gB antigen and the same HCMV gH/gL/UL128/UL130/UL131 pentameric complex antigen.

In particular, the immunogenic composition according to the invention is an immunogenic composition comprising:
  an HCMV gB antigen;
  an HCMV gH/gL/UL128/UL130/UL131 pentameric complex antigen; and
  a Th1-inducing adjuvant,
wherein said Th1-inducing adjuvant induces in mice a lower IgG1:IgG2a,c ratio, and/or a higher INF-y level, and/or a lower IL-5 level than MF59 in a composition comprising the same HCMV gB antigen and the same HCMV gH/gL/UL128/UL130/UL131 pentameric complex antigen.

In particular, Th1-inducing adjuvant according to the invention comprises:
  a TLR-4 agonist; or
  a linear or branched polyacrylic acid polymer salt with a weight average molecular weight Mw in the range of 350 to 650 kDa.

In particular, an immunogenic composition according to the invention is an immunogenic composition comprising:
  an HCMV gB antigen;
  an HCMV gH/gL/UL128/UL130/UL131 pentameric complex antigen; and
  a Th1-inducing adjuvant,
wherein said Th1-inducing adjuvant comprises:
  a TLR-4 agonist selected from the group consisting of a lipopolysaccharide, a monophosphoryl lipid A (MPL), a 3-de-O-acylated monophosphoryl lipid A (3D-MPL), a glucopyranosyl lipid adjuvant (GLA), a second-generation lipid adjuvant (SLA), a phospholipid dimer connected by a noncarbohydrate backbone and an aminoalkyl glucosaminide phosphate, or a derivative thereof; or
  a polyacrylic acid polymer salt with a weight average molecular weight Mw in the range of 350 to 650 kDa.

In one embodiment, said Th1-inducing adjuvant comprises a TLR-4 agonist.

A TLR (toll-like receptor) agonist is understood to mean a natural TLR ligand, a TLR ligand mimic, a synthetic or chemical TLR ligand, a cell or particle including a pathogen associated molecular pattern, a microbial pathogen, a bacterium, a virus and viral-like particle.

TLR4 (toll-like receptor type 4) is a receptor expressed by antigen-presenting cells of the immune system; it is involved in early defense mechanisms against gram-bacterial infections. The lipopolysaccharide (LPS) of gram-bacteria is the natural ligand for TLR4; it activates the receptor, which triggers a cascade of biochemical events, in particular the activation of Nf-Kappa B transcription factor, and the production of pro-inflammatory cytokines. The ability of a compound to stimulate the TLR4 pathway can be evaluated by methods known by those skilled in the art, as described for instance in the Journal of Biological Chemistry, (2001), vol 276(3), page 1873-1880.

Examples of TLR4 agonists include monophosphoryl lipid A (MPL), or a derivative thereof, particularly 3-de-O-acylated monophosphoryl lipid A (3D-MPL) as described in GB2211502 or in U.S. Pat. No. 4,912,094, or a derivative thereof, Phosphorylated hexaacyl disaccharide also called glucopyranosyl lipid adjuvant or GLA (CAS Number 1246298-63-4) or a derivative thereof, second-generation Lipid Adjuvant (SLA) such as described in Carter et al., Clin. Transl. Immunology, 2016, 5(11):e108 or in EP2437753 or U.S. Pat. No. 9,480,740, or a derivative thereof, aminoalkyl glucosaminide phosphates (AGPs) as described in WO 98/50399 or in WO 01/034617, or a derivative thereof, in particular RC529 described in U.S. Pat. No. 6,113,918, or a derivative thereof, and chemical compounds or a phospholipid dimer (homodimer or heterodimer) connected by a noncarbohydrate backbone as described in US 2003/0153532 or in US 2005/0164988, or a derivative thereof, in particular the compounds identified and exemplified in US 2003/0153532 under the following names: ER803022 (CAS number: 287180-56-7), ER803058 (CAS number: 287180-57-8), ER803732 (CAS number: 287106-29-0), ER803789 (CAS number: 287180-61-4), ER804053 (CAS number: 287180-62-5), ER804057 (CAS number: 287180-63-6), ER804058 (CAS number: 287180-65-8), ER804059 (CAS number: 287180-64-7), ER 8044442 (CAS number: 287180-78-3), ER 804764 (CAS number: 287180-87-4), ER111232 (CAS number: 287180-48-7), ER112022 (CAS number: 287180-46-5), ER112048 (CAS number: 287106-02-9), ER112065 (CAS number: 287180-49-8), ER112066 (CAS number: 287180-50-1), ER113651 (CAS number: 287180-51-2), ER118989 (CAS number: 287180-52-3), ER119327 (CAS number: 287180-54-5) and ER119328 (CAS number: 287180-55-6), or a derivative thereof. These compounds have generally one or several asymmetric carbons. When these compounds have one or several asymmetric carbons, they can be used as a mixture of optical isomers or under the form of a specific isomer.

In particular, said TLR-4 agonist is chosen from a phospholipid dimer connected by a noncarbohydrate backbone and a GLA TLR-4 agonist.

In particular, the TLR4 agonist is a phospholipid dimer connected by a noncarbohydrate backbone.

In particular, the TLR4 agonist is a chemical compound or a phospholipid dimer connected by a noncarbohydrate backbone of formula I, II, III or IV:

Compound or phospholipid dimer connected by a non-carbohydrate backbone of formula I

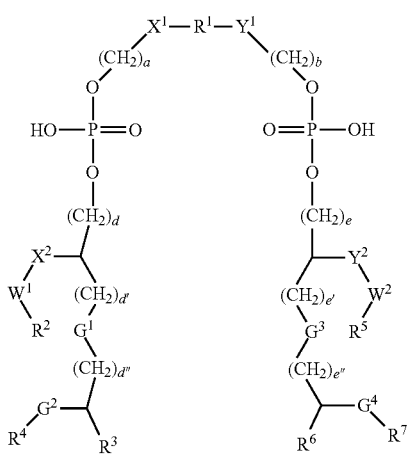

Compound or phospholipid dimer connected by a non-carbohydrate backbone of formula II

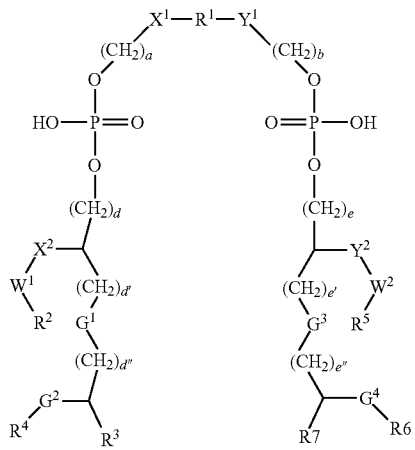

Compound or phospholipid dimer connected by a non-carbohydrate backbone of formula III

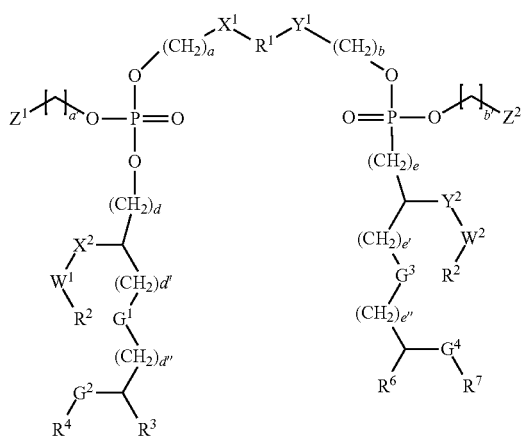

Compound or phospholipid dimer connected by a non-carbohydrate backbone of formula IV

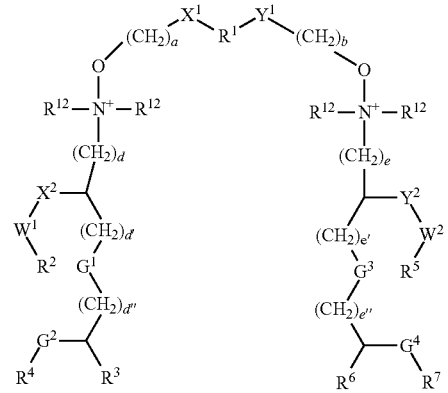

in which, for each of formula I, II, III or IV, $R^1$ is selected from the group consisting of:
a) C(O);
b) C(O)—($C_1$-$C_{14}$ alkyl)-C(O), in which said $C_1$-$C_{14}$ alkyl is optionally substituted with a hydroxyl, a $C_1$-$C_5$ alkoxy, a $C_1$-$C_5$ alkylenedioxy, a ($C_1$-$C_5$ alkyl)amino or a ($C_1$-$C_5$ alkyl)aryl, in which said aryl moiety of said ($C_1$-$C_5$ alkyl)aryl is optionally substituted with a $C_1$-$C_5$ alkoxy, a ($C_1$-$C_5$ alkyl)amino, a ($C_1$-$C_5$ alkoxy)amino, a ($C_1$-$C_5$ alkyl)-amino($C_1$-$C_5$ alkoxy), —O—($C_1$-$C_5$ alkyl)amino ($C_1$-$C_5$ alkoxy), —O—($C_1$-$C_5$ alkyl) amino-C(O)—($C_1$-$C_5$ alkyl)-C(O)OH, or —O—($C_1$-$C_5$ alkyl)amino-C(O)—($C_1$-$C_5$ alkyl)-C(O)—($C_1$-$C_5$)alkyl;
c) an alkyl comprising a $C_2$-$C_{15}$ linear or branched chain, optionally substituted with a hydroxyl or an alkoxy; and
d) —C(O)—($C_6$-$C_{12}$ arylene)-C(O)— in which said arylene is optionally substituted with a hydroxyl, a halogen, a nitro or an amino;
a and b are independently 0, 1, 2, 3 or 4;
d, d', d'', e, e' and e'' are independently 0, 1, 2, 3 or 4;
$X^1$, $X^2$, $Y^1$ and $Y^2$ are independently selected from the group consisting of null, an oxygen, NH and N (C(O) ($C_1$-$C_4$ alkyl)), and N($C_1$-$C_4$ alkyl);
$W^1$ and $W^2$ are independently selected from the group consisting of a carbonyl, a methylene, a sulfone and a sulfoxide;
$R^2$ and $R^5$ are independently selected from the group consisting of:
a) a $C_2$ to $C_{20}$ straight chain or branched chain alkyl, which is optionally substituted with an oxo, a hydroxyl or an alkoxy;
b) a $C_2$ to $C_{20}$ straight chain or branched chain alkenyl or dialkenyl, which is optionally substituted with an oxo, a hydroxyl or an alkoxy;
c) a $C_2$ to $C_{20}$ straight chain or branched chain alkoxy, which is optionally substituted with an oxo, a hydroxyl or an alkoxy;
d) NH—($C_2$ to $C_{20}$ straight chain or branched chain alkyl), in which said alkyl group is optionally substituted with an oxo, a hydroxy or an alkoxy; and
e)

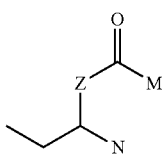

in which Z is selected from the group consisting of an O and NH, and M and N are independently selected from the group consisting of an alkyl, an alkenyl, an alkoxy, an acyloxy, an alkylamino and an acylamino comprising a $C_2$-$C_{20}$ linear or branched chain; $R^3$ and $R^6$ are independently selected from the group consisting of a $C_2$ to $C_{20}$ straight chain or branched chain alkyl or alkenyl, optionally substituted with an oxo or a fluoro; $R^4$ and $R^7$ are independently selected from the group consisting of a C(O)—($C_2$ to $C_{20}$ straight chain or branched chain alkyl or alkenyl), a $C_2$ to $C_{20}$ straight chain or branched chain alkyl, a $C_2$ to $C_{20}$ straight chain or branched chain alkoxy, and a $C_2$ to $C_{20}$ straight chain or branched chain alkenyl; in which said alkyl, alkenyl or alkoxy groups can be independently and optionally substituted with a hydroxyl, a fluoro or a $C_1$-$C_5$ alkoxy; $G_1$, $G_2$, $G_3$ and $G_4$ are independently selected from the group consisting of an oxygen, a methylene, an amino, a thiol, —C(O)NH—, —NHC(O)—, and —N(C(O)($C_1$-$C_4$ alkyl))-;
or $G^2R^4$ or $G^4R^7$ can together be a hydrogen atom or a hydroxyl;
and in which, for formula III:
a' and b' are independently 2, 3, 4, 5, 6, 7 or 8, preferably 2;
$Z^1$ is selected from the group consisting of —OP(O)(OH)$_2$, —P(O)(OH)$_2$, —OP(O)(OR$^8$)(OH) where $R^8$ is a $C_1$-$C_4$ alkyl chain, —OS(O)$_2$OH, —S(O)$_2$OH, —CO$_2$H, —OB(OH)$_2$, —OH, —CH$_3$, —NH$_2$ and —NR$^9_3$ where $R^9$ is a $C_1$-$C_4$ alkyl chain;
$Z^2$ is selected from the group consisting of —OP(O)(OH)$_2$, —P(O)(OH)$_2$, —OP(O)(OR$^{10}$)(OH) where $R^{10}$ is a $C_1$-$C_4$ alkyl chain, —OS(O)$_2$OH, —S(O)$_2$OH, —CO$_2$H, —OB(OH)$_2$, —OH, —CH$_3$, —NH$_2$ and —NR$^{11}$ where $R^{11}$ is a $C_1$-$C_4$ alkyl chain;
and in which, for formula IV:
$R^{12}$ is H or a $C_1$-$C_4$ alkyl chain;
or a pharmaceutically acceptable salt of the compound or the phospholipid dimer connected by a noncarbohydrate backbone of formula I, II, III or IV.
In particular, the TLR4 agonist according to the invention is a chemical compound or phospholipid dimer connected by a noncarbohydrate backbone of formula I,

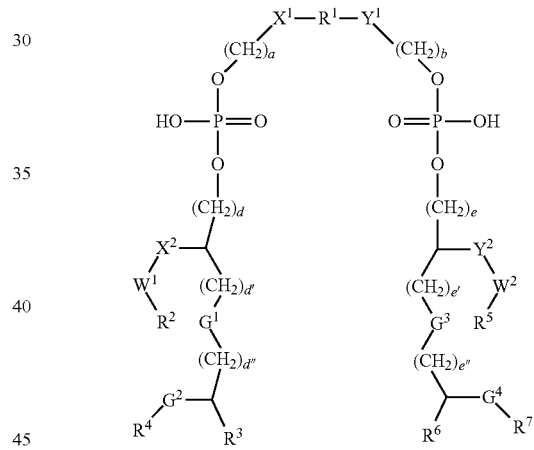

or a pharmaceutically acceptable salt of this compound or phospholipid dimer connected by a noncarbohydrate backbone.
Preferably,
$R^1$ is C(O) or C(O)—(CH$_2$)n-C(O), n being 1, 2, 3 or 4,
a, b, d, d', d'', e, e' and e'' are independently 1 or 2,
X1, X2, Y1 and Y2 are NH,
W1 and W2 are C(O),
$R^2$ and $R^5$ are independently selected from the group consisting of a $C_{10}$-$C_{15}$ straight chain alkyl optionally substituted with an oxo, an NH—($C_{10}$-$C_{15}$ straight chain alkyl), and

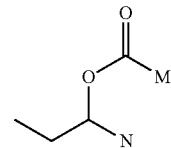

in which M and N are independently a C2 to C20 straight chain alkyl or alkenyl,

R3 and R6 are C5-C10 straight chain alkyls,

R4 and R7 are selected from the group consisting of a hydrogen, C(O)—(C8-C12 straight chain alkyl) or C(O) (C8 C12 straight chain alkenyl), G1 and G3 are an oxygen or —NH(CO)—, G2 and G4 are an oxygen.

In particular, the TLR4 agonist according to the invention is a symmetric phospholipid dimer (homodimer) connected by a noncarbohydrate backbone. More particularly, the symmetric phospholipid dimer connected by a noncarbohydrate backbone is a dimer of a triacyl phospholipid. More particularly, said TLR-4 agonist is E6020 (CAS number: 287180-63-6).

In particular, said TLR-4 agonist is GLA (CAS Number 1246298-63-4).

These TLR4 agonists can also be themselves combined with a delivery system such as calcium phosphate, liposomes, virosomes, ISCOMs, micro- and nanoparticles, or emulsions.

As such, in particular, TLR4 agonist according to the invention is in combination with a delivery system such as aqueous nanosuspension, calcium phosphate, liposomes, virosomes, ISCOMs, micro- and nanoparticles, or emulsions.

Such delivery systems have been previously described and are well known by the man skilled in the art.

In particular, said TLR-4 agonist is chosen from E6020 (CAS number: 287180-63-6) and a GLA (CAS Number 1246298-63-4) TLR-4 agonist.

As an example of suitable formulation of a TLR4 agonist combined with a delivery system, citation can be made of an oil-in-water emulsion comprising as TLR4 agonist the compound ER 804057 (now called E6020) (CAS number: 287180-63-6), which is the disodium salt of the compound having the following chemical formula:

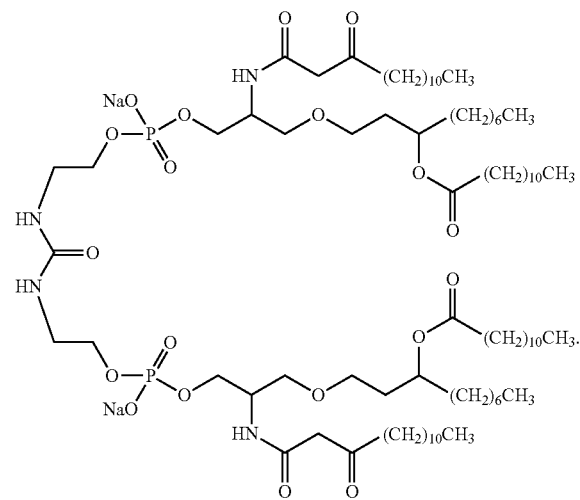

The four asymmetric carbons of E6020 are all in in the R configuration (R,R,R,R). Such an emulsion can be obtained for instance by microfluidisation techniques as described in WO 2004/060396 or by a phase inversion temperature process (PIT process) as described in WO 2007/080308.

As such, in particular, TLR4 agonist according to the invention is in combination with an oil-in-water emulsion, more particularly, a squalene-based oil-in-water emulsion.

An oil-in-water emulsion suitable for the purpose of the invention comprises a metabolizable oil (wherein the volume of oil represents 0.5 to 20% of the total volume of the emulsion (v/v), in particular 1 to 10% (v/v) and more particularly 1 to 5% (v/v)), an aqueous solution (wherein the volume of the aqueous solution represents 80 to 99.5% of the total volume (v/v), in particular 90 to 99% (v/v)) and one or several emulsifying agent(s) (wherein the total amount of the emulsifying agent represents 0.001 to 5% of the total amount of the emulsion (w/w), in particular 0.001 to 2% (w/w), and more particularly 0.01 to 2% (w/w)). The metabolizable oil is commonly one having about 6 to about 30 carbon atoms including, but not limited to, alkanes, alkenes, alkynes, and their corresponding acids and alcohols, the ethers and esters thereof, and mixtures thereof. The oil can be essentially any plant oil, fish oil, animal oil or synthetically prepared oil that can be metabolized by the body of the human subject to which the emulsion compositions will be administered and that is not substantially toxic to the subject. The metabolizable oil can be an unsaturated hydrocarbon having from 20-40 carbons, or a branched, polyunsaturated hydrocarbon having from 20-40 carbon atoms, for example, terpenoids. An unsaturated terpenoid known as squalene, 2,6,10,15,19,23-hexamethyl-2,6,10,14,18,22-tetracosahexaene and its saturated analog, squalane, are often preferred. Fish oils, including squalene and squalane, are readily available from commercial sources or may be obtained by methods known in the art. Another oil commonly used is tocopherol. Where a composition includes a tocopherol, any of the $\alpha$, $\beta$, $\gamma$, $\delta$, $\epsilon$ or $\xi$ tocopherols can be used but $\alpha$-tocopherols are preferred. A substantial number of suitable emulsifying agents (also referred as surfactants, detergents and so forth) are used in the pharmaceutical sciences, many of which are useful in the composition of the emulsion of the present invention, so long as they are sufficiently non-toxic. There are a number of emulsifying agents specifically designed for and commonly used in biological situations.

For example, a number of biological detergents (surfactants) are listed as such by Sigma Chemical. Such surfactants are divided into four basic types: anionic, cationic, zwitterionic, and nonionic.

Examples of anionic detergents include alginic acid, caprylic acid, cholic acid, 1-decanesulfonic acid, deoxycholic acid, 1-dodecanesulfonic acid, N-lauroylsarcosine, and taurocholic acid.

Cationic detergents include dodecyltrimethylammonium bromide, benzalkonium chloride, benzyldimethylhexadecyl ammonium chloride, cetylpyridinium chloride, methylbenzethonium chloride, and 4-picoline dodecyl sulfate.

Examples of zwitterionic detergents include 3-[(3-cholamidopropyl)-dimethylammonio]-1-propanesulfonate (commonly abbreviated CHAPS), 3-[(cholamidopropyl) dimethylammoniol-2-hydroxy-1-propanesulfonate (commonly abbreviated CHAPSO), N-dodecyl-N,N-dimethyl-3-ammonio-1-propanesulfonate, phosphatidylcholine and lyso-alpha-phosphatidylcholine.

Examples of nonionic detergents include decanoyl-N-methylglucamide, diethylene glycol monopentyl ether, n-dodecyl beta-D-glucopyranoside, poloxamers, ethylene oxide condensates of fatty alcohols (e.g., those sold under the trade name Lubrol), polyoxyethylene ethers of fatty acids (particularly C12-C20 fatty acids), polyoxyethylene sorbitan fatty acid esters (e.g., sold under the trade name Tween®), and sorbitan fatty acid esters (e.g., sold under the trade name Span®).

A particularly useful group of surfactants are the sorbitan-based non-ionic surfactants. These surfactants are typically prepared by dehydration of sorbitol to give 1,4-sorbitan, which is then reacted with one or more equivalents of a fatty acid. The fatty-acid-substituted moiety may be further reacted with ethylene oxide to give a second group of surfactants.

The fatty-acid-substituted sorbitan surfactants are typically made by reacting 1,4-sorbitan with a fatty acid such as lauric acid, palmitic acid, stearic acid, oleic acid, or a similar long chain fatty acid to give the 1,4-sorbitan mono-ester, 1,4-sorbitan sesquiester or 1,4-sorbitan triester. The common names for some of these surfactants include, for example, sorbitan monolaurate, sorbitan monopalmitate, sorbitan monostearate, sorbitan monooleate, sorbitan sesquioleate, and sorbitan trioleate. These surfactants are commercially available under the names SPAN® or ARLACEL®. SPAN® and ARLACEL® surfactants are lipophilic and are generally soluble or dispersible in oil. They are also soluble in most organic solvents. In water they are generally insoluble but dispersible. Generally these surfactants will have a hydrophilic-lipophilic balance (HLB) number between 1.8 and 8.6. Such surfactants can be readily made by means known in the art or are commercially available.

A related group of surfactants comprises polyoxyethylene sorbitan monoesters and polyoxyethylene sorbitan triesters. These materials are typically prepared by addition of ethylene oxide to a 1,4-sorbitan monoester or triester. The addition of polyoxyethylene converts the lipophilic sorbitan mono- or triester surfactant into a hydrophilic surfactant generally soluble or dispersible in water and soluble to varying degrees in organic liquids. The TWEEN® surfactants may be combined, for example, with a related sorbitan monoester or triester surfactant to promote emulsion stability. TWEEN® surfactants generally have a HLB value falling between 9.6 and 16.7. TWEEN® surfactants are commercially available from a number of manufacturers, for example ICI America's Inc., Wilmington, Del. under the registered mark ATLAS® surfactants.

Another group of non-ionic surfactants that could be used alone or in conjunction with SPAN®, ARLACEL® and/or TWEEN® surfactants are the polyoxyethylene fatty acids made by the reaction of ethylene oxide with a long-chain fatty acid. The most commonly available surfactant of this type is solid under the name MYRJ® and is a polyoxyethylene derivative of stearic acid. MYRJ® surfactants are hydrophilic and soluble or dispersible in water, like TWEEN® surfactants. The MYRJ® surfactants may be blended, for example, with TWEEN® surfactants or with TWEEN®/SPAN® or with ARLACEL® surfactant mixtures for use in forming emulsions. MYRJ® surfactants can be made by methods known in the art or are available commercially from ICI America's Inc.

Another group of polyoxyethylene based non-ionic surfactants are the polyoxyethylene fatty acid ethers derived from lauryl, acetyl, stearyl and oleyl alcohols. These materials are typically prepared as above by addition of ethylene oxide to a fatty alcohol. The commercial name for these surfactants is BRIJ®; BRIJ® surfactants may be hydrophilic or lipophilic depending on the size of the polyoxyethylene moiety in the surfactant. While the preparation of these compounds is available from the art, they are also readily available from such commercial sources as ICI America's Inc.

Other non-ionic surfactants that may be used in the practice of this invention are, for example: polyoxyethylenes, polyol fatty acid esters, polyoxyethylene ethers, polyoxypropylene fatty ethers, bee's wax derivatives containing polyoxyethylene, polyoxyethylene lanolin derivatives, polyoxyethylene fatty glycerides, glycerol fatty acid esters or other polyoxyethylene acid alcohols or ether derivatives of long-chain fatty acids of 12-22 carbon atoms. Preferably, the polyoxyethylene alkyl ether is chosen from the group consisting of ceteareth-12 (sold under the name Eumulgin® B1), ceteareth-20 (Eumulgin® B2), steareth-21 (Eumulgin® S21), ceteth-20 (Simulsol® 58 or Brij® 58), ceteth-10 (Brij® 56), steareth-10 (Brij® 76), steareth-20 (Brij® 78), oleth-10 (Brij® 96 or Brij® 97) and oleth-20 (Brij® 98 or Brij® 99). The number attributed to each chemical name corresponds to the number of ethylene oxide units in the chemical formula. In a particular aspect, the polyoxyethylene alkyl ether is BRIJ® 56 or polyoxyethylene (12) cetostearyl ether, provided by the company Cognis under the name Eumulgin™ B1. Among the sorbitan ester and mannide ester based surfactants with a HLB less than 9 that are particularly suitable, mention may be made of the sorbitan monooleate sold under the name Dehymuls SMO™ or Span®80. Among the mannide ester-based surfactants, mention may be made of the mannide monooleate sold by the company Sigma, or by the company Seppic under the name Montanide 80™.

Two or more surfactants can be combined in the emulsion part of the composition of the present invention.

The aqueous solution of the O/W emulsion part of the composition of the present invention is buffered saline or unadulterated water. Because the composition of the invention is intended for parenteral administration, it is preferable to make up final buffered solutions used as vaccines so that the tonicity, i.e., osmolality, is essentially the same as normal physiological fluids in order to prevent post-administration swelling or rapid absorption of the composition because of differential ion concentrations between the composition and physiological fluids. It is also preferable to buffer the saline in order to maintain a pH compatible with normal physiological conditions. Also, in certain instances, it may be necessary to maintain the pH at a particular level in order to insure the stability of the gB antigen and of the HCMV gH/gL/UL128/UL130/UL131 pentameric complex antigen if they are present in the O/W emulsion.

Any physiologically acceptable buffer may be used herein, but phosphate buffers are preferred. Other acceptable buffers such as acetate, tris, bicarbonate, carbonate, citrate or the like may be used as substitutes for phosphate buffers. The pH of the aqueous component will preferably be between 6.0 and 8.0.

The O/W emulsion part of the composition of the present invention may comprise supplemental components that can be added at the time of preparing the O/W emulsion or added once the O/W emulsion is prepared.

Example can be given of AF04, a squalene-based oil-in-water (O/W) emulsion that contains E6020, which was obtained according to the process described in WO 2007/080308.

GLA (CAS Number 1246298-63-4) TLR-4 agonist is the compound having the following chemical formula:

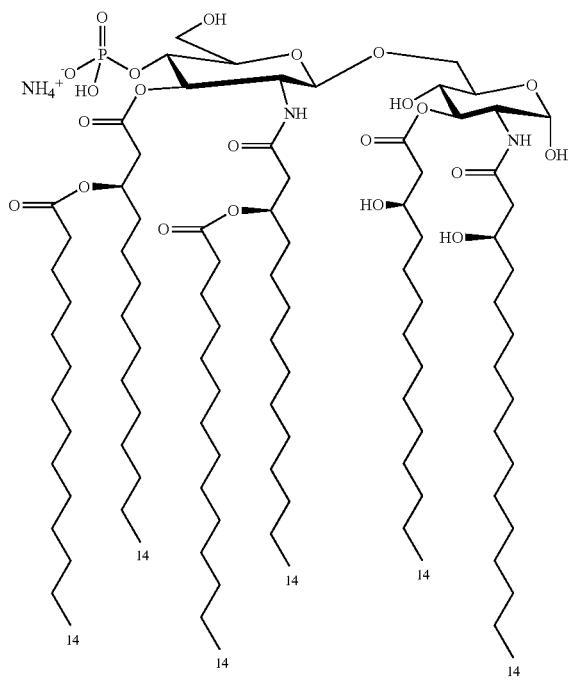

GLA can be purchased for instance on Avanti Polar's catalog with reference 699800 (Avanti Polar Lipids Inc., Alabaster, USA).

In particular, GLA is in combination with a delivery system such as calcium phosphate, liposomes, virosomes, ISCOMs, micro- and nanoparticles, or emulsions. Preferentially, GLA is in combination with an oil-in-water emulsion, more particularly, a squalene-based oil-in-water emulsion.

Example can be given of GLA-SQEM, a squalene-based oil-in-water (O/W) emulsion that contains GLA.

In the Table 1 below, the quantity of the different raw materials used to obtain 100 mL of the GLA-SQEM with a concentration of 10% squalene are mentioned. The final emulsion contains 4% (v/v) of squalene (34 mg/ml) and 100 µg/mL of GLA, in 22.5 mM of ammonium phosphate.

TABLE 1

| Preparation at 10% squalene | Mass % (w/v) | Quantity for 100 mL | Reference |
|---|---|---|---|
| Aqueous phase (90%): | | | |
| 25 mM Ammonium Phosphate pH 6.1 qsp 90 ml | | 87.7 mL | |
| Poloxamer 188 (PluronicF68) | 0.09 | 90.0 mg | P5556 from SIGMA |
| Glycerol | 2.25 | 2.25 g | 24388238 Normapur from VWR Prolabo |
| Oil phase (10%) | | | |
| Squalene 10% v/v (85.6mg/ml) | 8.56 | 10.0 mL | 1208076 from SOPHIM, redistilled to remove peroxides |
| Dimyristoyl-phosphatidyl-choline (DMPC) | 1.9 | 1.90 g | 850345P from Avanti Polar Lipids |
| GLA | 0.025 | 25.0 mg | 699800P from Avanti Polar Lipids |

The oil phase is prepared by sonication in a bath at 55-60° C. Then, the aqueous phase is added upon the oil phase (weighing). A pre-emulsion is obtained after homogenization on Ultra Turrax T25 (IKA) at 9500 r/min, during 2 cycles of 30 secondes. Then, microfluidization is done on Emulsiflex C3 during 20 passages at an air pressure of 55 psi (homogenization pressure between 1450 and 1600 bars). The emulsion is then diluted 2.5 fold in a 25 mM Ammonium Phosphate buffer, to obtain the final GLA-SQEM emulsion at 4% squalene. The emulsion is sterile filtered at about 40° C. with a 10 ml syringe and an Acrodisc 0.8-0.2 µm Supor Membrane filter (PALL n° PN4187).

Other suitable adjuvants comprising a TLR4 agonist are AS01, which comprises 3D-MPL and QS21 in a liposomal formulation or AS02, which comprises 3D-MPL and QS21 formulated in an oil-in-water emulsion (Garçon et al., Exp. Rev. of Vaccines, 2007, 6(5):723-739, EP0671948).

In one embodiment, said Th1-inducing adjuvant comprises a linear or branched polyacrylic acid polymer salt with a weight average molecular weight Mw in the range of 350 to 650 kDa.

Said polymer is a linear or a branched polyacrylic acid polymer, but it is not a cross-linked polymer.

By "polyacrylic acid polymer", is meant a polymer which is exclusively composed of acrylic acid units. So, in the form of a salt, said polyacrylic acid polymer salt is exclusively composed of units corresponding to a salt of acrylic acid or is exclusively composed of units corresponding to the free acid form of acrylic acid and of units corresponding to a salt of acrylic acid.

A linear or a branched polyacrylic acid polymer is obtained by polymerization of only acrylic acid as monomer. The polymerization is, most of the time, carried out by radical polymerization, using an oxidizing agent as initiator or catalyst. The most used oxidizing agents are persulfate (peroxydisulfate), for instance sodium or potassium persulfate. Branched polyacrylic acid polymers are, for instance, described in Macromolecules 2011, 44, 5928-5936. When the polymer according to the invention is linear, its Mark Houwink slope is higher or equal to 0.7 (Yan J. K., Pei J. J., Ma H. L., Wang Z. B. 2015. Effects of ultrasound on molecular properties, structure, chain conformation and degradation kinetics of carboxylic curdlan. Carb. Polymers. 121, 64-70).

The polyacrylic acid polymer salt can be in a solid form (precipitate or powder) or preferably in a liquid formulation. A liquid formulation will include the polyacrylic acid polymer salt and an aqueous solution. Preferably, such a formulation has a pH in the range of 5.5 to 8.0. This pH can be obtained by incorporation of a base, like NaOH, in the aqueous solution. The aqueous solution can be a buffered aqueous solution, obtained with a buffer such as a phosphate buffer, a TRIS (2-amino-2-hydroxymethyl-1,3-propanediol), Hepes (acide 4-(2-hydroxyethyl)-1-piperazine ethane sulfonique), histidine or citrate buffer. The liquid formulation may also comprise one or several additional salts, such as NaCl.

In particular, said linear or branched polyacrylic acid polymer salt is exclusively composed of units corresponding to a salt of acrylic acid or is exclusively composed of units corresponding to the free acid form of acrylic acid and of units corresponding to a salt of acrylic acid.

Advantageously, said polyacrylic acid polymer salt comprises less than 0.005%, preferably less than 0.001%, w/w of oxidizing agents, based on the total dry weight of said polyacrylic acid polymer salt and/or comprises less than 0.005%, preferably less than 0.001%, w/w of persulfates, based on the total dry weight of said polyacrylic acid polymer salt.

In a more particular embodiment, said polyacrylic acid polymer is a salt with Na+.

In particular embodiments, said polyacrylic acid polymer salt has a polydispersity index below or equal to about 4, preferably below or equal to about 2.5.

In particular embodiments, said polyacrylic acid polymer salt has a weight average molecular weight Mw in the range of 380 to 620 kDa and a polydispersity index below or equal to 4; or has a weight average molecular weight Mw in the range of 400 to 600 kDa and a polydispersity index below or equal to 4; or has a weight average molecular weight Mw in the range of 380 to 620 kDa and a polydispersity index below or equal to 2.5; or has a weight average molecular weight Mw in the range of 400 to 600 kDa and a polydispersity index below or equal to 2.

Advantageously, said polyacrylic acid polymer salt comprises less than 0.005% w/w of acrylic acid monomer in free acid form or salt form, based on the total dry weight of said polyacrylic acid polymer salt.

According to advantageous embodiments, said polyacrylic acid polymer salt is in a liquid formulation which has a pH in the range of 5.5 to 8.0.

According to advantageous embodiments, said polyacrylic acid polymer salt is in a buffered aqueous solution, in particular with a phosphate buffer, or a TRIS, Hepes, histidine or citrate buffer.

According to advantageous embodiments, said polyacrylic acid polymer salt is diafiltered and sterilized.

When, the polyacrylic acid polymer salt or the liquid formulation of the polyacrylic acid polymer salt is diafiltered, the sterilization occurs after the diafiltration.

According to the invention, the weight average molecular weight Mw is obtained by size exclusion chromatography. Advantageously, three detectors will be used after the size exclusion chromatography column: a right angle light scattering detector, a refractive index detector and a four-capillary differential viscometer. The do/dc used for the determination of Mw is preferably determined using the refractive index detector with a panel of polyacrylic acid polymers of known concentration. The content of persulfate and the content of acrylic acid monomer in free acid form or salt form can be determined by High Performance Anion Exchange Chromatography with conductimetric detection.

A process for the preparation of such polymer comprises for example the following successive steps:
a) having a solution of a polyacrylic acid polymer,
b) purifying the solution of the polyacrylic acid polymer, in order to eliminate impurities, and
c) sterilizing the purified solution of the polyacrylic acid polymer.

A process for the storage of a solution of such polymer salt comprises for examples the above mentioned preparation process, followed by a storage step of the obtained polymer, in solution.

In particular, said linear or branched polyacrylic acid polymer salt with a weight average molecular weight Mw in the range of 350 to 650 kDa is PAA225000.

Product named PAA225000 (Ref. 18613, sodium salt) can be obtained from Polysciences Europe (Eppelheim, Germany) in the form of a concentrated solution. It can be diluted with water to obtain a concentration of 20 mg/ml, and maintained under agitation at room temperature during 12 hours. The pH can be adjusted to 7.55 with HCl and the solution can be dialyzed at room temperature against 150 mM NaCl aqueous solution (3 consecutive baths) by using 2 kDa cutoff dialysis cassettes (Thermo Fischer Scientific, Courtaboeuf, France). The solution can then be filtered through a 0.22 μm PVDF membrane, for sterilization. The Molecular Weight of the polymer salt can then be measured and be 488 550 Da. Its Mn can be 129 070 Da and its IP 3.8.

The polymer can then be stored at +4° C., as a solution comprising 20 mg/ml of polymer in 150 mM NaCl aqueous solution. This solution can then be mixed with PBS 1C concentrated 10 times with sterile water, in order to get a saline solution comprising 2 mg/ml of polymer salt.

Any other Th1-inducing adjuvant may be used in the composition of the invention. As examples of adjuvants known to induce predominantly a Th1-type immune response, the following one can be cited: adjuvants or combinations of adjuvants comprising a saponin such as the ones described in WO8809336 or in U.S. Pat. No. 5,057,540, in particular QS21 and its synthetic or semi-synthetic analogues, a TLR3 agonist such as PolyI:C and derivatives thereof, a TLR5 agonist such as flagellin and derivatives thereof, a TLR7 agonist or a TLR7/8 agonist such as imidazoquinoline and derivatives thereof such as the ones described in EP1318835, a TLR8 agonist such as motolimod also known as VTX-2337 (as described in Lu et al., Clin Cancer Res, 2012, 18(2):499-509) and derivatives thereof or TLR8 agonists developed by Dynavax, a TLR9 agonist such as CpG oligodeoxynucleotides and derivatives thereof such as described in Vollmer et al., Expert Opin. Biol. Ther., 2005, 5(5):673-682, in particular ISS1018 or CpG 7909, a RIG-I-Like receptor (RLR) agonist such as RIG-I agonist, in particular 5' triphosphate RNA or small molecular weight agonists from Kineta, or a stimulator of interferon genes (STING) agonist, in particular cyclic dinucleotides (e.g. c-di-AMP, c-di-GMP, c-di-GAMP), a poly[di(carboxylatophenoxy)phosphazene] (PCPP) as described in Payne et al., Dev Biol Stand. 1998, 92:79-87, a poly[di(sodium carboxylatoethylphenoxy)]phosphazene (PECP) as described in Dar A et al., Vet Immunol Immunopathol., 2012, 146(3-4):289-95, or a Carbopol.

These Th1-inducing adjuvants can be combined with a delivery system such as aqueous nanosuspension, calcium phosphate, liposomes, virosomes, ISCOMs, micro- and nanoparticles, emulsions.

The adjuvant and the antigens of the immunogenic composition according to the invention can be formulated with any pharmaceutically acceptable vehicle. In the context of the invention, the expression "pharmaceutically acceptable vehicle" refers to a vehicle that is physiologically acceptable for administration to a human being, while retaining the physiological activity of the immunogenic composition according to the invention, i.e. its ability to induce an immune response. One exemplary pharmaceutically acceptable vehicle is a physiological saline buffer. Other physiologically acceptable vehicles are known to those skilled in the art and are described, for instance, in Remington's Pharmaceutical Sciences (18th edition), ed. A. Gennaro, 1990, Mack Publishing Company, Easton, Pa. An immunogenic composition as described herein may optionally contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, human serum albumin, essential amino acids, nonessential amino acids, L-arginine hydrochlorate, saccharose, D-trehalose dehydrate, sorbitol, tris (hydroxymethyl) aminomethane and/or urea. In addition, the vaccine composition may optionally comprise pharmaceutically acceptable additives including, for example, diluents, binders, stabilizers, and preservatives.

The pH of the immunogenic composition is usually between 5.5 and 8, and more preferably between 6.5 and 7.5 (e.g. about 7). Stable pH may be maintained by the use of a buffer e.g. a Tris buffer, a citrate buffer, phosphate buffer, a Hepes buffer, or a histidine buffer. Thus, the immunogenic composition generally includes a buffer. Immunogenic compositions may be isotonic with respect to humans. The immunogenic composition may also comprise one or several additional salts, such as NaCl.

The immunogenic compositions may be sterilized by conventional sterilization techniques, or may be sterile filtered. The resulting aqueous solutions may be packaged and stored in liquid form or lyophilized, the lyophilized preparation being reconstituted with a sterile aqueous carrier prior to administration. In a preferred embodiment, the immunogenic compositions are packaged and stored as micropellets via a prilling process as described in WO2009109550. Each micropellet may comprise the gB antigen, the gH/gL/UL128/UL130/UL131 pentameric complex antigen and the Th1-inducing adjuvant optionally with the oil-in-water emulsion. Alternatively, the gB antigen, the gH/gL/UL128/UL130/UL131 pentameric complex antigen and the Th1-inducing adjuvant optionally with the oil-in-water emulsion may be comprised alone or in any combination in different micropellets that can be mixed before or after aqueous reconstitution to obtain the composition of the invention.

The adjuvant and the antigens part of the immunogenic composition according to the invention are usually mixed together if there is no incompatibility between the products or alternatively the adjuvant can be extemporaneously added just prior to administration to a subject.

In one embodiment, the immunogenic composition of the invention is prepared as a ready-to-use mix of the HCMV gB antigen, the HCMV gH/gL/UL128/UL130/UL131 pentameric complex antigen and the Th1-inducing adjuvant.

In another embodiment, the immunogenic composition of the invention is prepared extemporaneously, just before administration to the human subjects. Thus, the invention provides kits including the various components ready for mixing. The kit allows the HCMV gB antigen, the HCMV gH/gL/UL128/UL130/UL131 pentameric complex antigen, the Th1-inducing adjuvant and optionally the oil-in-water emulsion to be kept separately until the time of use.

These components are physically separated from each other within the kit, and this separation can be achieved in various ways. For instance, they may be in separate containers, such as vials. In some arrangements, all the components are kept separately until the time of use. Preferably, the gB antigen and the HCMV gH/gL/UL128/UL130/UL131 pentameric complex antigen are in the same container and the Th1-inducing adjuvant and optionally the oil-in-water emulsion is (are) in another container. The contents of the vials can then be mixed, e.g., by removing the content of one vial and adding it to the other vial, or by separately removing the contents of all the vials and mixing them in a new container. In one example, one or more of the kit components is (are) in syringe(s) and the other in container(s) such as a vial. The syringe can be used (e.g., with a needle) to insert its contents into another container for mixing, and the mixture can then be withdrawn into the syringe. The mixed contents of the syringe can then be administered to a patient, typically through a new sterile needle. In another arrangement, the kit components are held together but separately in the same syringe. When the syringe is actuated (e.g., during administration to a patient) the contents of the chambers are mixed. This arrangement avoids the need for a separate mixing step at the time of use. The kit components will generally be in aqueous form. In some arrangements, one or more component(s) is (are) in dry form (e.g., in a lyophilized form or as micropellets), with the other component(s) being in aqueous form. The components can be mixed in order to reactivate the dry component and give an aqueous composition for administration to a patient. One or more lyophilized component(s) can be located within a vial or in a syringe. Dried components may include stabilizers such as mannitol, sucrose, or dodecyl maltoside, as well as mixtures thereof e.g. lactose/sucrose mixtures, sucrose/mannitol mixtures, etc. In some arrangements, all the components are in dry form (e.g., in a lyophilized form or as micropellets), held in the same recipient or separately in several recipients and the kit contains another recipient containing an aqueous solution for the reconstitution of the vaccine.

Accordingly, the invention provides a kit comprising: (i) a first kit component comprising an HCMV gB antigen and an HCMV gH/gL/UL128/UL130/UL131 pentameric complex antigen and (ii) a second kit component comprising a Th1-inducing adjuvant and optionally comprising oil-in-water emulsion; and the use of such kit for preventing HCMV infection.

In a preferred embodiment, the immunogenic composition of the invention is available in one vial/syringe as a ready-to-use mix of the HCMV gB antigen, the HCMV gH/gL/UL128/UL130/UL131 pentameric complex antigen and the Th1-inducing adjuvant.

The immunogenic composition, according to the invention can be administered via any suitable route, such as by mucosal administration (e.g. intranasal or sublingual), parenteral administration (e.g. intramuscular, subcutaneous, transcutaneous, or intradermal route), or oral administration. As appreciated by the man skilled in the art, a vaccine of the present invention is suitably formulated to be compatible with the intended route of administration.

The immunogenic composition according to the invention can be administered alone or with suitable pharmaceutical carriers, and can be in solid or liquid form such as, tablets, capsules, powders, solutions, suspensions, or emulsions.

For use as aerosols, the immunogenic composition according to the invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Uses

As previously mentioned, the invention also relates to an immunogenic composition as described herein for use as an HCMV vaccine.

In particular, the HCMV vaccine according to the invention is a subunit vaccine.

It further relates to a method of prevention of HCMV infection in a patient in need thereof, comprising the administration of an immunologically effective amount of the immunogenic composition according to the invention.

"HCMV" is used as described previously and an HCMV infection can in particular relate to a maternal HCMV infection during pregnancy or a congenital infection.

In particular, said vaccine/immunogenic composition increases neutralizing antibody levels and/or persistence. More particularly, said vaccine/immunogenic composition comprising an HCMV gB antigen, an HCMV gH/gL/UL128/UL130/UL131 pentameric complex antigen and a Th1-inducing adjuvant induces higher neutralizing antibody levels and/or persistence than a vaccine/immunogenic composition comprising the same HCMV gB antigen, the same HCMV gH/gL/UL128/UL130/UL131 pentameric complex antigen and MF59 adjuvant.

By "vaccine" as used herein is meant an immunogenic composition which is administered to induce an immune response that will protect or treat a subject from illness, in particular due to that agent. The vaccine of the present invention is intended for use as a preventive (prophylactic) vaccine, for administration to the subject prior to infection, with the intent to prevent initial (and/or recurrent) infection. In the particular case of congenital HCMV infection, the present invention is intended for use as a preventive vaccine for adolescent girls and women of child bearing age before pregnancy in order to prevent the vertical HCMV transmission from mother to fetus or infant.

An immunogenic composition according to the invention comprises an immunologically effective amount of the antigens and adjuvants described herein. An "immunologically effective amount" is an amount which, when administered to a subject, is effective for eliciting an immune response against the antigen used. This amount can vary depending on the health and physical condition of the subject to be treated, their age, the capacity of the subject's immune system to produce antibodies, the degree of protection desired, the formulation of the vaccine, the treating doctor's assessment of the medical situation. This amount can be determined by routine methods by the man skilled in the art.

Subject" has mentioned herein is used in a similar way as for "patient" and refers to a human, in particular women of childbearing age (16-45y) and adolescent girls (11-15 years) whatever their CMV serostatus, as well as a men, a child, or a patient candidate for solid organ or stem cell transplantation. In particular, said patient or subject is susceptible to contract HCMV.

A "neutralizing antibody" as described herein has the meaning known by a man skilled in the art and is intended to cover an antibody that neutralizes its target directly, for example by blocking the virus entry into a host cell as well as by blocking the virus dissemination from cell to cell. Neutralizing antibodies are functional antibodies that are able to protect from their target. Some illustration of the methods available to determine increase of neutralizing antibody levels and/or persistence is provided in the experimental part of the present application.

The vaccine according to the invention may be administered by any route commonly used for administering a vaccine. A regimen leading to the induction of the expected immune response will be used. Usually, the immunization schedule includes several administrations. The amount of the immunogenic composition administered is enough to produce the desired immune response and is determined by the person skilled in the art.

A vaccine according to the present invention may be administered in multiple doses. For example, a vaccine according to the present invention may be administered in one, two or three doses. When a vaccine according to the present invention is administered in three doses, the first dose and the third dose are preferably administered approximately twelve months apart. For instance, a vaccine of the present invention may be administered in a first dose, a second dose and a third dose, wherein said second dose is to be administered about one to three months after said first dose and wherein said third dose is to be administered about six to twelve months after said first dose. Alternatively, the three doses may be administered at zero months, at about one to two months (e.g. at about one-and-a-half months) and at about six months.

A vaccine according to the present invention may be administered in two doses. Preferably, the first dose and the second dose are administered approximately about one, three, six, eight or nine months apart.

A vaccine according to the present invention may be administered in a single dose.

Optionally, booster administrations of a vaccine according to the present invention may be used, for example between six months and ten years, for example six months, one year, three years, five years or ten years after initial immunization (i.e. after administration of the last dose scheduled in the initial immunization regimen).

All references cited herein, including journal articles or abstracts, published patent applications, issued patents or any other references, are entirely incorporated by reference herein, including all data, tables, figures and text presented in the cited references.

In the scope of the present invention, it has to be understood that "an immunogenic composition for use" is equivalent to "the use of a immunogenic composition" and in particular that "a immunogenic composition for use as a vaccine" is equivalent to "the use of a immunogenic composition as a vaccine" and to "the use of a immunogenic composition for the manufacture of a medicament intended to be used as vaccine".

The invention will be further illustrated by the following figures and examples.

FIGURES

FIG. 1: Study schedule

Figure 2:
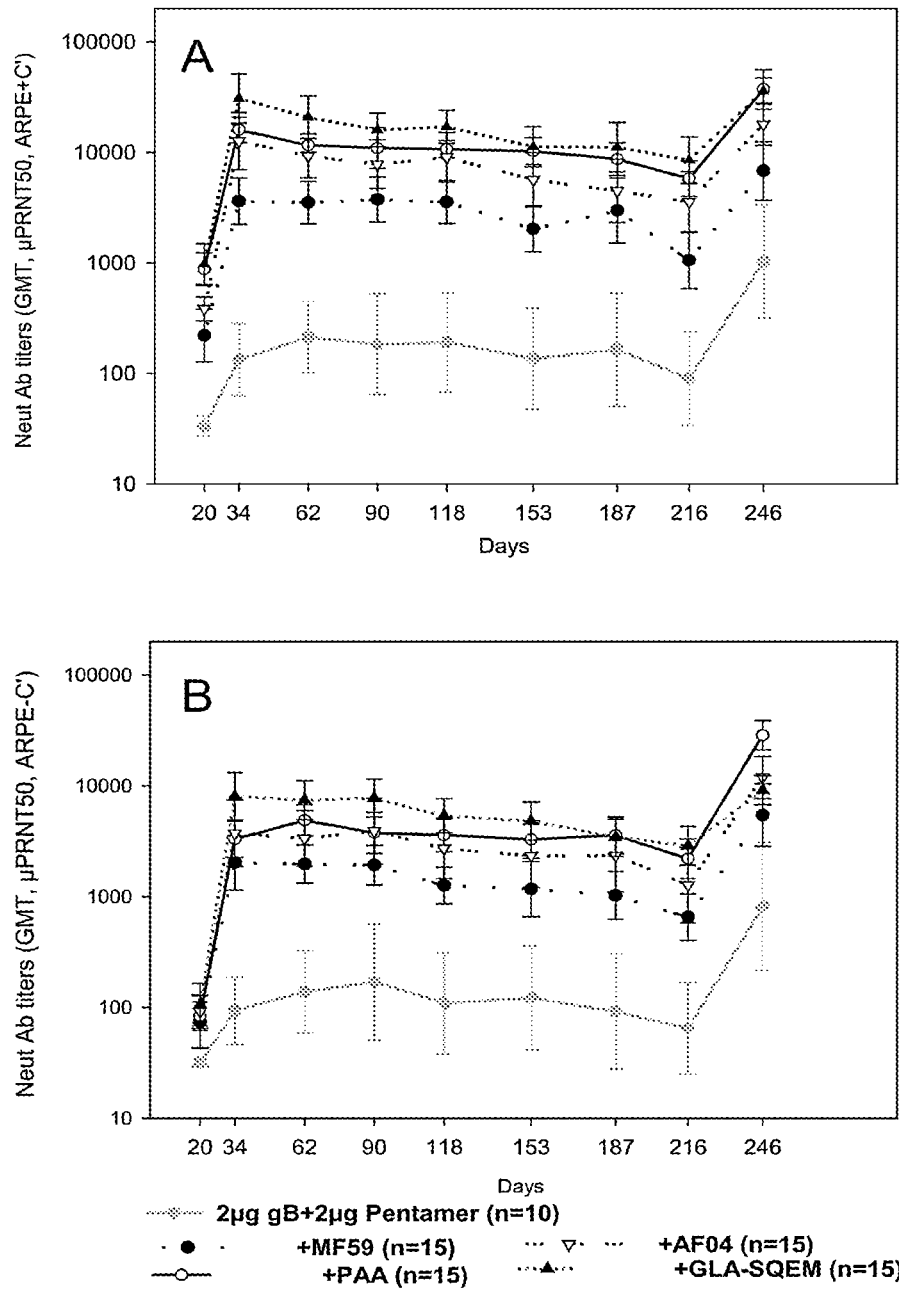

FIG. 2: Kinetic of the neutralizing antibody titers specific to HCMV BAD-rUL131-Y4 GFP strain measured by seroneutralization assay on epithelial cells with (panel A) or without complement (panel B) in sera collected from day 20 to day 257 from mice immunized at days 0, 20 and 227 with 2 µg of CMV-gB and pentamer without or with different adjuvants.

Figure 3:
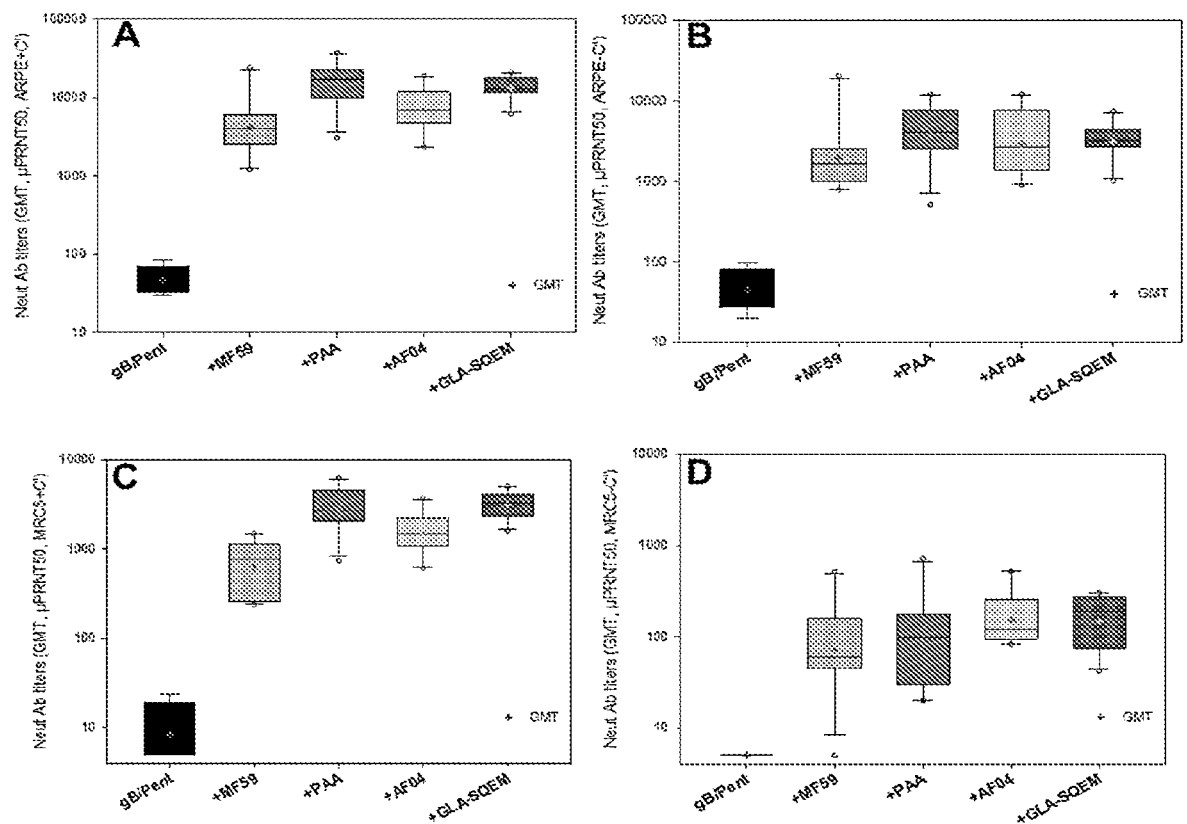

FIG. 3: Neutralizing antibody titers specific to HCMV BAD-rUL131-Y4 GFP strain measured by seroneutralization assay on epithelial cells with (panel A) or without complement (panel B) and on fibroblasts with (panel C) or without complement (panel D) in sera collected at day 34 from mice immunized at days 0 and 20 with 2 µg of CMV-gB and pentamer without or with different adjuvants.

Figure 4:
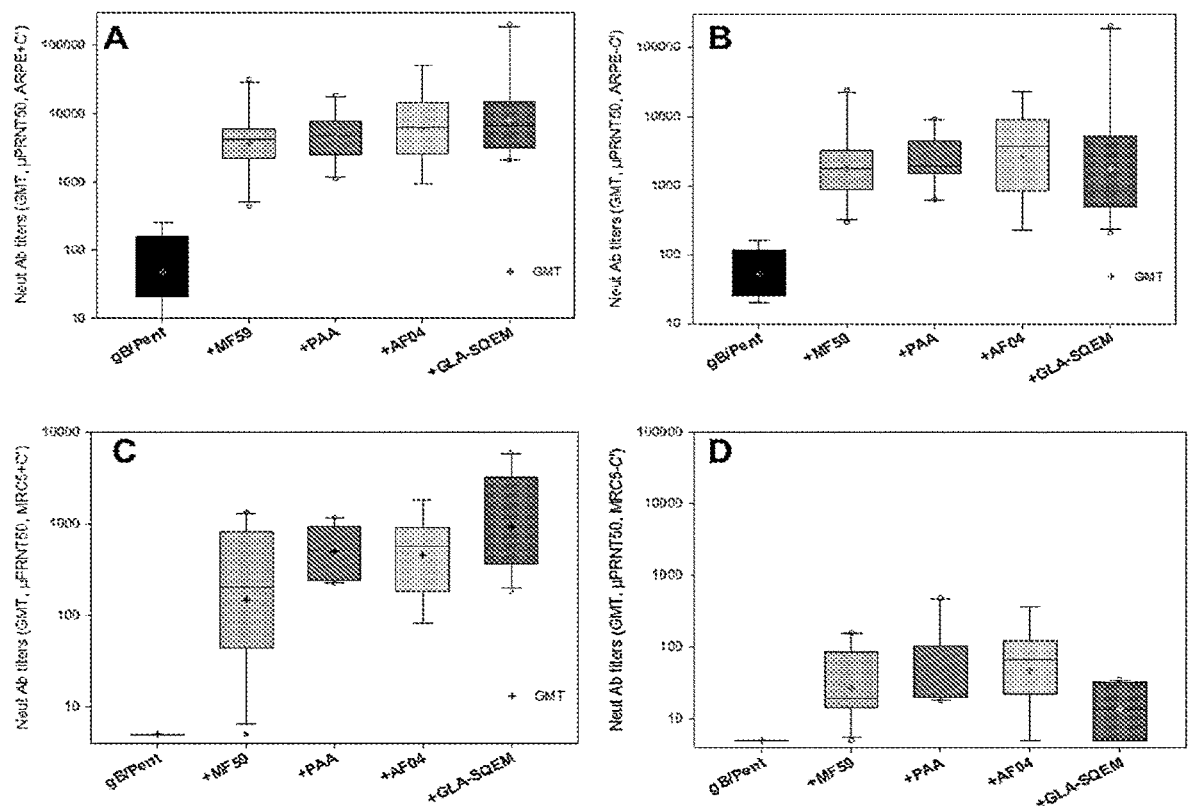

FIG. 4: Neutralizing antibody titers specific to HCMV BAD-rUL131-Y4 GFP strain measured by seroneutralization assay on epithelial cells with (panel A) or without complement (panel B) and on fibroblasts with (panel C) or without complement (panel D) in sera collected at day 208 from mice immunized at days 0 and 20 with 2 µg of CMV-gB and pentamer without or with different adjuvants.

Figure 5:
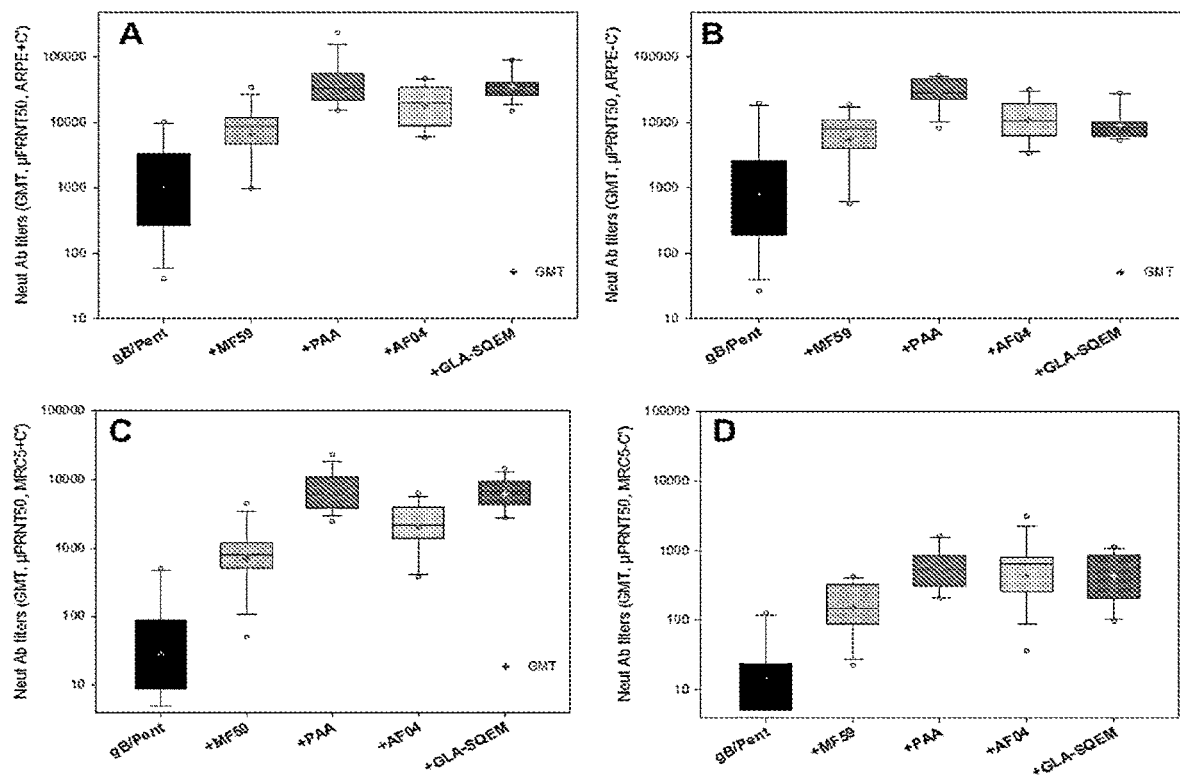

FIG. 5: Neutralizing antibody titers specific to HCMV BAD-rUL131-Y4 GFP strain measured by seroneutralization assay on epithelial cells with (panel A) or without complement (panel B) and on fibroblasts with (panel C) or without complement (panel D) in sera collected at day 257 from mice immunized at days 0, 20 and 227 with 2 µg of CMV-gB and pentamer without or with different adjuvants.

FIG. 6: Anti-gB IgG1 and IgG2c antibody titers specific to CMV-gB (panel A) or to CMV-pentamer (panel B) measured by ELISA in sera collected at days 34, 208 and 257 from mice immunized at days 0, 21 and 227 with 2 µg of CMV-gB and pentamer without or with different adjuvants.

FIG. 7: Mean IgG1/IgG2c antibody ratios calculated at day 34, 208 and 257 for each group from mice immunized at 0, 21 and 227 with 2 µg of CMV-gB and pentamer with MF59 or with different adjuvants.

FIG. 8: IL-5 and IFN-γ cytokine secreting cells frequencies (cytokine secreting cells/$10^6$ splenocytes) upon ex-vivo stimulation with recombinant CMV-gB (panel A) or CMV-pentamer (panel B) monitored at days 34, 208 and 257 in splenocytes from mice immunized at days 0, 20 and 227 with 2 µg of CMV-gB and pentamer without or with different adjuvants.

FIG. 9: IgG1 and IgG2c percentages of antibody secreting plasmablasts specific to either CMV-gB (panel A) or CMV-pentamer (panel B) at days 34, 208 and 257 from mice immunized at days 0, 20 and 227 with 2 µg of CMV-gB and pentamer without or with different adjuvants.

FIG. 10: IgG1 and IgG2c percentages of antibody secreting B memory cells specific to either CMV-gB (panel A) or CMV-pentamer (panel B) at days 34, 208 and 257 from mice immunized at days 0, 20 and 227 with 2 µg of CMV-gB and pentamer without or with different adjuvants.

FIG. 11: Neutralizing antibody titers specific to HCMV BAD-rUL131-Y4 GFP strain measured by seroneutralization assay on epithelial cells ARPE-19 or on fibroblasts MRC-5 in presence of complement in sera collected at D20 from mice immunized at D0 with different doses of CMV-gB and CMV-gH/gL/UL128/UL130/UL131 pentamer formulated with PAA adjuvant.

FIG. 12: Neutralizing antibody titers specific to HCMV BAD-rUL131-Y4 GFP strain measured by seroneutralization assay on epithelial cells ARPE-19 in either presence (12A) or absence (12B) of complement in sera collected at D35 from mice immunized at D0 and D21 with different doses of CMV-gB and CMV-gH/gL/UL128/UL130/UL131 pentamer formulated with PAA adjuvant.

FIG. 13: IFN-γ cytokine-producing cells quantification in mice splenocytes upon ex-vivo stimulation with either CMV-gB, CMV-gH/gL/UL128/UL130/UL131 pentamer (panel A) or CMV-pentamer peptide pools (panel B) measured by ELISPOT assay in splenocytes collected at D35 from mice immunized at D0 and D21 with 3 µg of CMV-gB and 3 µg of CMV-gH/gL/UL128/UL130/UL131 pentamer formulated with PAA adjuvant.

EXAMPLES

TABLE 2

| List of abbreviations | |
|---|---|
| Acronym/Abbreviation | Designation/Description |
| CMV | Cytomegalovirus |
| D | Day |
| ELISA | Enzyme Linked Immuno Sorbent Assay |
| EU | ELISA Unit |
| IFNg | Gamma interferon |
| Ig | Immunoglobulin |
| IL | Interleukin |
| IM | Intra-muscular |
| IP | Intra-peritoneal |
| M | Month |
| N/A | Not Applicable |
| SN | Seroneutralization |
| W | Week |

Example 1

Material and Methods

Material

Product(s) Tested in the Examples

Products are described in Table 3. Female 7-weeks-old C57BL/6J mice were immunized by the intra-muscular (IM) route (hind leg, quadriceps) under a volume of 50 µl on D0 and D20 and D227.

TABLE 3

| Product Name | Concentration | Source or composition |
|---|---|---|
| Pentamer CMV | 1 mg/ml | The Native Antigen company, Oxford UK |
| gB (CMV) | 685.5 µg/ml | gBdTM obtained as described in U.S. Pat. No. 6,100,064, which is a 806 AA long polypeptide |
| PAA225000 (PAA) | 8 mg/ml PAA 225000 | Polysciences Europe GmbH, Hirschberg an der Bergstrasse, Germany |
| MF59 | 4% squalene | Quantity per mL: Squalene 39.0 mg Polysorbate 80 4.7 mg Sorban trioleate 4.7 mg Sodium citrate, dehydrate 2.65 mg Citric acid, monohydrate 0.17 mg Water for injections q.s.p. 1 mL |
| AF04 | 5% squalene, 0.04 mg/ml E6020 | Obtained according to the process described in WO 2007/080308. |
| GLA-SQEM | 4% squalene, 0.1 mg/ml GLA | GLA from Avanti Polar Lipids Inc., Alabaster, USA GLA-SQEM is obtained according to the process described above in the description of the invention |

Methods

Group Definition

Study groups are described in the following Table 4. Mice were randomly allocated to one of the following 7 groups. Each group is differentiated in 3 subgroups, i.e. A=>A1, A2 and A3 depending on the time-point analysis requiring mouse euthanasia to collect the spleens (days 34, 208 and 257), as summarized in the study schedule on FIG. 1. Thirty five mice/groups were included as follow: 10 mice/sub-groups for sub-groups 1 and 2, and 15 mice in subgroups 3 in order to compensate for possible inter-current deaths that might happen over an eight month period. For control groups, only 5 mice/subgroup were included in subgroups A1, A2 and A3 and for group B, only 5 mice/subgroup B1 and B2 were included and 10 mice for subgroup B3.

TABLE 4

| Groups | Sub-Groups (number of mouse) | Products under test | | | | |
|---|---|---|---|---|---|---|
| | | Active substance | | Adjuvant | | Adm. |
| | | Name | dose | Name | Dose | route |
| A (15) | A1 (5) | PBS | — | — | — | IM |
| | A2 (5) | | | | | 50 µl at D0, D21 |
| | A3 (5) | | | | | IM 50 µl at D0, D21, M7 |
| B (20) | B1 (5) | gB + Pentamer | 2 µg | — | — | IM |
| | B2 (5) | | | | | 50 µl at D0, D21 |
| | B3 (10) | | 2 µg | | | IM 50 µl at D0, D21, M7 |
| C (35) | C1 (10) | gB + Pentamer | 2 µg | MF59 | 2% squalene | IM 50 µl at D0, D21 |
| | C2 (10) | | | | | |
| | C3 (15) | | 2 µg | | | IM 50 µl at D0, D21, M7 |
| D (35) | D1 (10) | gB + Pentamer | 2 µg | PAA | 200 µg | IM 50 µl at D0, D21 |
| | D2 (10) | | | | | |
| | D3 (15) | | 2 µg | | | IM 50 µl at D0, D21, M7 |
| E (35) | E1 (10) | gB + Pentamer | 2 µg | AF04 | 1 µg E6020, 2.5% squalene | IM 50 µl at D0, D21 |
| | E2 (10) | | 2 µg | | | |
| | E3 (15) | | | | | IM 50 µl at D0, D21, M7 |
| F (35) | F1 (10) | gB + Pentamer | 2 µg | GLA-SQEM | 2.5 µg GLA, 2% squalene | IM 50 µl at D0, D21 |
| | F2 (10) | | | | | |
| | F3 (15) | | 2 µg | | | IM 50 µl at D0, D21, M7 |

Biological Sampling and Analytical Tests
Biological Sampling

Blood samples were collected from all the animals under anesthesia. The anesthesia was performed by Imalgene® (1.6 mg of Ketamine) and Rompun (0.32 mg of Xylazine) administered in a volume of 200 µl via the intraperitoneal route. Around 1 mL of blood was collected in vials containing clot activator and serum separator (BD Vacutainer SST ref 367783). After a night at +4° C., blood was centrifuged at 3000 rpm during 20 minutes and serum was collected and stored at −20° C. until analysis.

For cellular response assays, spleens were collected in sterile conditions and splenocytes were isolated as soon as possible after spleen sampling.

Analytical Tests
Seroneutralization Assays

This technique is used to titrate the functional neutralizing antibodies present in the sera of CMV-gB+pentamer+adjuvant immunized animals. Based on the ability of the Cytomegalovirus to infect MRC5 fibroblasts and ARPE-19 cells (human epithelial cells), a serum containing specific functional antibodies against CMV-gB and/or CMV-pentamer can inhibit the viral infection of the cells.

Briefly, 2.5×10$^4$ MRC5 fibroblasts or ARPE-19 cells were dispensed in 96-well dark plates the day before the microneutralization (MN) assay. On D0, sera were heat-inactivated at 56° C. for 30 min. Serum samples were serially two-fold diluted in DMEM/F12 1% FBS, starting from 1/10 to 1/10240 in a 96-deep-well plate and incubated with 4.2 log FFU/ml of the BADrUL131-Y4 CMV virus strain (provided by Thomas Shenk, as described in Wang et al., J. Virol., 2005, 79(16):10330-10338), titrating 4.89 or 4.71 log FFU/ml on ARPE-19 or MRC5 cells, respectively) for 60 min at 37° C. in a 5% CO2 cell culture incubator. The serum/virus mixtures were then transferred onto the MRC5 or the ARPE-19 cells and incubated at 37° C. in a 5% CO$_2$ cell culture incubator. The incubation was performed on 3 days for the MRC5 cells and on 4 days for the ARPE cells.

On D3 or D4, after removal of culture supernatant, cells were fixed with 100 µl of 1% formol in PBS for 1 hour at room temperature. The plates were then washed three times with PBS and air-dried at room temperature before analysis on the Microvision fluorescent plate reader to count infected cells in each well.

As control, two wells of cell control (without virus) and six wells with cells infected with half of the viral dilution containing the 4.2 log FFU/mL were present on each plate. The mean of these six wells defined the threshold of seroneutralization, determined as 50% of the specific-signal value. Neutralizing end-point titers were defined as the reciprocal of the last dilution that fell below the calculated 50% specific-signal value. Neutralizing titers (pPRNT50) were defined for each individual serum as the last dilution that induced 50% reduction of infected cells, i.e. the last dilution that induced lower infected cells than the calculated 50% specific-signal value. Geometric mean neutralizing antibody titers were calculated for each group.

ELISA Assay

Serum IgG1 and IgG2c antibodies directed against CMV-gB antigen or against CMV-pentamer antigen were titrated by a robot ELISA assay according to the following procedure.

Dynex 96-well microplates were coated overnight at 4° C. with 1 µg/well of CMV-gB or CMV-pentamer, in 0.05 M carbonate/bicarbonate buffer, pH 9.6 (Sigma). Plates were then blocked at least 1 hour at 37° C. with 150 µL/well of PBS Tween-milk (PBS pH7.1, 0.05% Tween 20, 1% (w/v) powdered skim milk (DIFCO)). All next incubations were carried out in a final volume of 100 µL, followed by 3 washings with PBS pH 7.1, 0.05% Tween 20. Serial two-fold dilution of serum samples were performed in PBS-Tween-milk (starting from 1/1000 or 1/10000) and were added to the wells. Plates were incubated for 90 min at 37° C. After washings, goat anti-mouse IgG1 or IgG2c peroxydase conjugate antibodies (Southern Biotech) diluted in PBS-Tween-milk at 1/2000 were added to the wells and plates were incubated for 90 min at 37° C. Plates were further washed and incubated in the dark for 30 min at 20° C. with 100 μL/well of a ready-to-use Tetra Methyl Benzidine (TMB) substrate solution (TEBU). The reaction was stopped with 100 μL/well of HCl 1M (Prolabo).

Optical density (OD) was measured at 450 nm-650 nm with a plate reader (VersaMax—Molecular Devices). The IgG1 or IgG2c antibodies titers were calculated using the CodUnit software, for the OD value range of 0.2 to 3.0 from the titration curve (reference mouse hyper immune serum put on each plate). The IgG1 or IgG2c titer of this reference, expressed in arbitrary ELISA Units (EU) corresponds to the log 10 of the reciprocal dilution giving an OD of 1.0. The threshold of antibody detection was 10 ELISA units (1.0 log 10).

All final titers were expressed in log 10 (Log).

IgG1/IgG2c ratios were calculated using the individual arithmetic values and the geometric mean of individual IgG1/IgG2c ratios was calculated for each group.

Fluorospot

The fluorescent-linked immunospot (FLUOROSPOT) is used for detecting and enumerating individual cells secreting the IFN-γ and IL-5 cytokines.

On D0, the membrane of the 96-well IPFL-bottomed microplates (Multiscreen) was pre-wetted for 1 minute with 25 μL of 35% ethanol. Ethanol was then removed and each well was washed twice with 200 μL of PBS 1×. Microplates were then coated with a rat anti-mouse IFN-γ or rat anti-mouse IL-5 antibodies (10 μg/ml, Pharmingen) diluted at 1/100 and 1/50 respectively and were incubated overnight at 4° C.

On D1, plates were washed with PBS and then blocked at least 2 h at 37° C. with RPMI 10% FBS. After plates washing, 5×10$^5$ freshly isolated splenocytes/well were incubated overnight with the CMV-gB antigen (0.1 μg/ml), CMV-pentamer (0.1 μg/ml) or concanavalin A (Con A, 2.5 μg/mL) as a positive control, in presence of murine IL-2 (10 U/ml).

On D2, the plates were washed 6 times with PBS 1×-BSA 0.1% (200 μL/well). After the washing step, 100 μL/well of the biotinylated anti-mouse IFN-γ or anti-mouse IL5 antibodies were added at 1 μg/mL in PBS1×-BSA 0.1% for 2 hours at room temperature, in the dark. The plates were washed again 3 times with PBS 1×-BSA 0.1% (200 μL/well). Then, 100 μL/well of streptavidin-PE at 1 μg/mL in PBS 1×-BSA 0.1% was incubated for 1 hour at room temperature, in the dark.

The plates were further washed 6 times with PBS 1×-BSA 0.1% (200 μL/well). The plates were stored at 5° C.±3° C. in the dark until reading.

Each spot, corresponding to an IFN-γ or IL5 secreting cell (IFN-γ SC or IL5 SC), was enumerated with an automatic FLUOROSPOT plate reader (Microvision). Results were expressed as number of IFN-γ or IL-5 secreting cell per 10$^6$ splenocytes.

IgG, IgG1 and IgG2c FLUOROSPOT Assay

The fluorescent-linked immunospot (FLUOROSPOT) is used for detecting and enumerating individual B cells secreting antibodies irrespective of antigen specificity (IgG1, IgG2c or total IgG).

On D0, the membrane of the 96-well IPFL-bottomed microplates (Multiscreen) was pre-wetted for 1 minute with 25 μL of 35% ethanol. Ethanol was then removed and each well was washed twice with 200 μL of PBS 1×. Microplates were then coated with CMV-gB antigen (10 μg/ml, Sanofi), CMV-pentamer (10 μg/ml, NAC) or total IgG antibody (10 μg/ml, KPL) diluted at 1/68, 1/100 and 1/100 respectively and were incubated overnight at 4° C.

On D1, plates were washed with PBS and then blocked at least 2 h at 37° C. with RPMI 10% FBS.

After plates washing, 5×10$^5$ freshly isolated splenocytes/well for CMV-gB antigen or CMV-pentamer and 2.5.10$^5$ freshly isolated splenocytes/well for total IgG antibody were incubated 5 hours.

After 5 hours, the plates were washed 3 times with PBS 1× and stored à 4° C. for the night.

On D2, the plates were washed 6 times with PBS 1×-BSA 0.1% (200 μL/well). After the washing step, 100 μL/well of the anti-mouse IgG1 PE or anti-mouse IgG2c FITC or anti-mouse total IgG antibodies were added respectively at 4, 2 or 0.5 μg/mL in PBS1×-BSA 0.1% for 2 hours at room temperature, in the dark. The plates were washed again 6 times with PBS 1×-BSA 0.1% (200 μL/well). The plates were stored at 5° C.±3° C. in the dark until reading.

Each spot, corresponding to an antibody secreting cell (ASC) (IgG1 ASC, IgG2c ASC or total IgG ACS), was enumerated with an automatic FLUOROSPOT plate reader (Microvision). Results were expressed as number of antibody secreting cell per 10$^6$ splenocytes.

Results

Humoral Response

Longitudinal Analysis of the Neutralizing Antibody Response on ARPE-19 Epithelial Cells Between Day 20 and 257

The neutralizing activity against the BADrUL131-Y4 CMV virus strain on epithelial cells (ARPE-19) was monitored by seroneutralization assays in individual intermediate serum samples collected monthly from all animals from subgroups 3 from day 20 to day 257 (i.e. at days 20, 34, 62, 90, 118, 153, 187, 226 and 257). The seroneutralization technique is detailed in the material and methods section and raw data are shown in Tables 5 a-b.

Tables 5 a-b

| | Group | Serum | ARPE D20 + C | ARPE M1 + C | ARPE M2 + C | ARPE M3 + C | ARPE M4 + C | ARPE M5 + C | ARPE M6 + C | ARPE M7 + C | ARPE M8 + C |
|---|---|---|---|---|---|---|---|---|---|---|---|
| A | PBS | GMT | 24 | 16 | 25 | 29 | 23 | 21 | 17 | 22 | 16 |
| B | Pentamer: 2 μg gB: 2 μg | GMT | 33 | 133 | 212 | 183 | 191 | 136 | 164 | 90 | 1026 |
| C | Pentamer: 2 μg gB: 2 μg MF59: 2.3% squalene | GMT | 220 | 3625 | 3516 | 3748 | 3562 | 2034 | 2973 | 1058 | 6792 |

| Group | Serum | ARPE D20 + C | ARPE M1 + C | ARPE M2 + C | ARPE M3 + C | ARPE M4 + C | ARPE M5 + C | ARPE M6 + C | ARPE M7 + C | ARPE M8 + C |
|---|---|---|---|---|---|---|---|---|---|---|
| D | Pentamer: 2 µg gB: 2 µg PAA: 200 µg | GMT | 879 | 15990 | 11598 | 10962 | 10724 | 10266 | 8681 | 5792 | 37166 |
| E | Pentamer: 2 µg gB: 2 µg AF04: 1 µg E6020, 2.5% squalene | GMT | 383 | 12648 | 9288 | 7833 | 9048 | 5653 | 4494 | 3559 | 17936 |
| F | Pentamer: 2 µg gB: 2 µg GLA-SQEM: 2.5 µg GLA, 2% squalene | GMT | 976 | 30755 | 20844 | 15957 | 17068 | 11231 | 11156 | 8505 | 35897 | a-Sub Group 3-intermediary-Seroneutralization ARPE with complement

| Group | Serum | ARPE D20 − C | ARPE M1 − C | ARPE M2 − C | ARPE M3 − C | ARPE M4 − C | ARPE M5 − C | ARPE M6 − C | ARPE M7 + C | ARPE M8 + C |
|---|---|---|---|---|---|---|---|---|---|---|
| A | PBS | GMT | 30 | 16 | 18 | 13 | 71 | 22 | 12 | 12 | 13 |
| B | Pentamer: 2 µg gB: 2 µg | GMT | 32 | 94 | 138 | 170 | 109 | 122 | 92 | 65 | 815 |
| C | Pentamer: 2 µg gB: 2 µg MF59: 2.3% squalene | GMT | 74 | 2020 | 1973 | 1928 | 1264 | 1174 | 1028 | 655 | 5449 |
| D | Pentamer: 2 µg gB: 2 µg PAA: 200 µg | GMT | 83 | 3297 | 4890 | 3768 | 3589 | 3289 | 3580 | 2201 | 28657 |
| E | Pentamer: 2 µg gB: 2 µg AF04: 1 µg E6020, 2.5% squalene | GMT | 91 | 3734 | 3354 | 3918 | 2728 | 2344 | 2359 | 1274 | 11910 |
| F | Pentamer: 2 µg gB: 2 µg GLA-SQEM: 2.5 µg GLA, 2% squalene | GMT | 106 | 8048 | 7446 | 7774 | 5392 | 4812 | 3459 | 2883 | 9150 | b-Sub Group 3-intermediary-Seroneutralization ARPE without complement

Geometric mean titers (GMT) as well as individual neutralizing titers are depicted in FIG. 2.

M1=D34, M2=D62, M3=D90, M4=D118, M5=D153, M6=D187, M7=D226, M8=D257.

Similar kinetics neutralizing antibody titer profiles were detected in presence and absence of complement in the epithelial-based neutralizing assay as depicted in FIG. 2 panels A and B, respectively.

For the group administered with unadjuvanted CMV-gB and pentamer, a low neutralizing antibody response was detected at day 20 (GMT=33 and 32, with or without complement, respectively) and then increased up to day 62 to reach a plateau with GMT ranging from 90 to 212 or from 65 to 170, in presence or absence of complement, between day 62 and day 226. The 3rd injection at day 226, boosted the neutralizing antibody titers as detected at days 257 with GMT=1026 or 815, in presence or absence of complement, respectively.

For all the adjuvanted groups (MF59, PAA, AF04 and GLA-SQEM), neutralizing antibody titers were detected in presence or absence of complement on day 20 (i.e. 20 days after the first injection) with GMTs at 220 or 74, respectively, for group C3 administered with CMV-gB and pentamer adjuvanted with MF59 and with GMTs≥383 and ≥83 for groups D3 to F3 administered with the other adjuvant formulations. At day 34 (i.e. 14 days after the 2nd injection), all the adjuvanted groups presented the peak of the response after 2 injections with GMTs ranging from 3 625 to 30 755 or from 2 020 to 8 048, in presence or absence of complement, respectively.

Over the 6 month period (between day 34 and 226), the epithelial-based neutralizing antibody titers slightly decreased down to titers ranging from 1 058 to 8 505 or from 655 to 2883, in presence or absence of complement, respectively. Similarly the 3rd injection at day 226, boosted the neutralizing antibody titers as detected at days 257 with GMTs ranging 6 792 (i.e. for MF59-) to 37 166 (i.e. for PAA-) or from 5 449 (i.e. for MF59-) to 28 657 (i.e. for -PAA adjuvanted group), in presence or absence of complement, respectively.

To compare the different adjuvanted groups i.e. SPA09, AF04 and GLA-SQEM to the MF59 reference, a statistical mixed model with 2 fixed factors (group and time) was performed on repeated neutralizing antibody titers between days 34 to 226.

With respect to the group comparison as presented in Table 6, in presence of complement, the neutralizing antibody titers obtained in mice administered with CMV-gB and pentamer adjuvanted with MF59 were not significantly superior to the neutralizing antibody titers obtained in mice administered with unadjuvanted CMV-gB and pentamer whereas all the other adjuvanted groups (i.e. PAA, AF04 and GLA-SQEM) were significantly superior to the neutralizing antibody titers obtained in mice administered with CMV-gB and pentamer adjuvanted with MF59 (all p-values <0.001).

In absence of complement, the neutralizing antibody titers obtained in mice administered with CMV-gB and pentamer adjuvanted with MF59 were not significantly superior to the neutralizing antibody titers obtained in mice administered with unadjuvanted CMV-gB and pentamer. The neutralizing antibody titers obtained in mice administered with CMV-gB and pentamer adjuvanted with AF04 were not significantly superior to the neutralizing antibody titers obtained in mice administered with CMV-gB and pentamer adjuvanted with MF59, whereas all the other adjuvanted groups (i.e. PAA and GLA-SQEM) were significantly superior to the neutralizing antibody titers obtained in mice administered with CMV-gB and pentamer adjuvanted with MF59 (all p_values 0.009). The neutralizing antibody titers obtained in mice administered with CMV-gB and pentamer adjuvanted with AF04 were significantly superior to the neutralizing antibody titers obtained in mice administered with unadjuvanted CMV-gB and pentamer (all p-values <0.001).

TABLE 6

| ARPE-19 neutralizing assay | In presence of Complement | In absence of Complement |
|---|---|---|
| Comparison | P-value* | P-value* |
| (B3) unadjuvant vs (C3) MF59 | 1.000 (NS) | 1.000 (NS) |
| (D3) PAA vs (C3) MF59 | <0.001 (S) *x4.2* | 0.009 (S) *x2.4* |
| (E3) AF04 vs (C3) MF59 | <0.001 (S) *x2.8* | 0.077 (NS) |
| (F3) GLA-SQEM vs (C3) MF59 | <0.001 (S) *x6.6* | <0.001 (S) *x4.0* |

Statistical comparison of the different groups within estimated repeated neutralizing antibody titers between days 34 to 226 (Superiority test, *p-values with Dunnett adjustment, NS: not significant or S: significant superiority, when significant the fold increase is indicated in italic).

Detailed Neutralizing Antibody Response on Epithelial Cells (ARPE-19) and Fibroblasts (MRC-5) at Days 34 (M1), 208 (M7) and 257 (M8)

The neutralizing activity against the BADrUL131-Y4 CMV virus strain on epithelial cells (ARPE-19) and fibroblasts (MRC-5) was monitored by seroneutralization assays in individual serum samples collected from all animals from subgroups 1, 2 and 3 at, respectively, days 34 (2 weeks after the second immunization), 208 (7 months after the primary vaccination series) and 257 (1 month after the booster injection at M7). The seroneutralization technique is detailed in the material and methods section and raw data are shown in Tables 7 a-f.

Tables 7 a-f

| | Group | Serum | ARPE J34 +C | ARPE J34 −C |
|---|---|---|---|---|
| A | PBS | GMT | 12 | 12 |
| B | Pentamer: 2 µg gB: 2 µg | GMT | 46 | 43 |
| C | Pentamer: 2 µg gB: 2 µg MF59: 2.3% squalene | GMT | 4168 | 1934 |
| D | Pentamer: 2 µg gB: 2 µg PAA: 200 µg | GMT | 14698 | 3862 |
| E | Pentamer: 2 µg gB: 2 µg AF04: 1 µg E6020, 2.5% squalene | GMT | 7179 | 2919 |
| F | Pentamer: 2 µg gB: 2 µg GLA-SQEM: 2.5 µg GLA, 2% squalene | GMT | 13302 | 3146 | a.- Sub Group 2- Seroneutralization ARPE D234 (D208)

| | Group | Serum | ARPE M7 +C | ARPE M7 −C |
|---|---|---|---|---|
| A | PBS | GMT | 14 | 17 |
| B | Pentamer: 2 µg gB: 2 µg | GMT | 46 | 51 |
| C | Pentamer: 2 µg gB: 2 µg MF59: 2.3% squalene | GMT | 3739 | 1834 |
| D | Pentamer: 2 µg gB: 2 µg PAA: 200 µg | GMT | 4484 | 2230 |
| E | Pentamer: 2 µg gB: 2 µg AF04: 1 µg E6020, 2.5% squalene | GMT | 6101 | 2718 |
| F | Pentamer: 2 µg gB: 2 µg GLA-SQEM: 2.5 µg GLA, 2% squalene | GMT | 7719 | 1758 | b- Sub Group 2- Seroneutralization ARPE M7 (D208)

| | Group | Serum | ARPE M8 +C | ARPE M8 −C |
|---|---|---|---|---|
| A | PBS | GMT | 16 | 13 |
| B | Pentamer: 2 µg gB: 2 µg | GMT | 1026 | 815 |
| C | Pentamer: 2 µg gB: 2 µg MF59: 2.3% squalene | GMT | 6792 | 5449 |
| D | Pentamer: 2 µg gB: 2 µg PAA: 200 µg | GMT | 37166 | 28657 |
| E | Pentamer: 2 µg gB: 2 µg AF04: 1 µg E6020, 2.5% squalene | GMT | 17936 | 11910 |
| F | Pentamer: 2 µg gB: 2 µg GLA-SQEM: 2.5 µg GLA, 2% squalene | GMT | 8505 | 9150 | c- Sub Group 3- Seroneutralization ARPE M8 (D257)

d- Sub Group 1- Seroneutralization MRC5 - D34

| Group | | Serum | MRC5 D34 +C | MRC5 D34 −C |
|---|---|---|---|---|
| A | PBS | GMT | 5 | 5 |
| B | Pentamer: 2 µg gB: 2 µg | GMT | 8 | 5 |
| C | Pentamer: 2 µg gB: 2 µg MF59: 2.3% squalene | GMT | 636 | 71 |
| D | Pentamer: 2 µg gB: 2 µg PAA: 200 µg | GMT | 2699 | 84 |
| E | Pentamer: 2 µg gB: 2 µg AF04: 1 µg E6020, 2.5% squalene | GMT | 1477 | 153 |
| F | Pentamer: 2 µg gB: 2 µg GLA-SQEM: 2.5 µg GLA, 2% squalene | GMT | 3131 | 146 | e- Sub Group 2- Seroneutralization MRC5 M7 (D208)

| Group | | Serum | MRC5 M7 +C | MRC5 M7 −C |
|---|---|---|---|---|
| A | PBS | GMT | 5 | 5 |
| B | Pentamer: 2 µg gB: 2 µg | GMT | 5 | 5 |
| C | Pentamer: 2 µg gB: 2 µg MF59: 2.3% squalene | GMT | 147 | 27 |
| D | Pentamer: 2 µg gB: 2 µg PAA: 200 µg | GMT | 500 | 39 |
| E | Pentamer: 2 µg gB: 2 µg AF04: 1 µg E6020, 2.5% squalene | GMT | 451 | 48 |
| F | Pentamer: 2 µg gB: 2 µg GLA-SQEM: 2.5µg GLA, 2% squalene | GMT | 913 | 14 | f- Sub Group 3- Seroneutralization MRC5 M8 (D257)

| Group | | Serum | MRC5 M8 +C | MRC5 M8 −C |
|---|---|---|---|---|
| A | PBS | GMT | 5 | 5 |
| B | Pentamer: 2 µg gB: 2 µg | GMT | 29 | 15 |
| C | Pentamer: 2 µg gB: 2 µg MF59: 2.3% squalene | GMT | 695 | 151 |
| D | Pentamer: 2 µg gB: 2 µg PAA: 200 µg | GMT | 6645 | 536 |
| E | Pentamer: 2 µg gB: 2 µg AF04: 1 µg E6020, 2.5% squalene | GMT | 1977 | 438 |
| F | Pentamer: 2 µg gB: 2 µg GLA-SQEM: 2.5 µg GLA, 2% squalene | GMT | 6152 | 427 |

Geometric mean titers (GMT) as well as individual neutralizing titers are depicted in FIG. 3, FIG. 4 and FIG. 5.

Similar neutralizing antibody profiles were observed on both epithelial- and fibroblast-based neutralizing assays, with higher neutralizing titers monitored in the epithelial-based neutralizing assay with at least 5-fold or 11-fold higher GMTs in presence or absence of complement, respectively.

At day 34, i.e. 14 days after the 2nd injection, no or low neutralizing antibody titers were detected in mice immunized with unadjuvanted CMV-gB and pentamer (GMT 8 on MRC-5 and 46 on ARPE-19 cells, respectively). For all the CMV-gB and pentamer adjuvanted groups, a marked adjuvant effect was observed with a 14- up to 337-fold increase of the SN titers on MRC-5 and 44- to 319-fold increase on ARPE-19 cells, irrespective of the presence or absence of complement, compared to the unadjuvanted group.

With respect to the neutralizing antibody titers on ARPE-19 epithelial cells in presence of complement (FIG. 3, panel A), an adjuvant effect with significantly higher neutralizing antibody titers than MF59 was observed with PAA and GLA-SQEM (at least 3- to 4.2-fold higher, test of superiority, unilateral Dunnet adjustment, all p_values <0.001) but not with AF04 (only 1.7-fold higher, p_value=0.08).

At the opposite, with respect to the neutralizing antibody titers on ARPE-19 cells in absence of complement (FIG. 3, panel B), PAA, AF04 and GLA-SQEM adjuvants slightly increased the neutralizing antibody titers as compared to MF59 (1.5- to 2-fold increase in neutralizing antibody titers as compared to those induced by MF59) but the observed differences were not statistically significant (all p_values>0.091).

With respect to the neutralizing antibody titers on MRC-5 fibroblasts in presence of complement (FIG. 3, panel C), an adjuvant effect with significantly higher neutralizing antibody titers than MF59 was observed with all the tested adjuvants PAA, AF04 and GLA-SQEM (at least 2.3- to 6-fold higher, test of superiority, unilateral Dunnet adjustment, all p_values ≤0.002).

Lastly, with respect to the neutralizing antibody titers on MRC-5 fibroblasts in absence of complement (FIG. 3, panel D), the neutralizing antibody titers induced by PAA, AF04 and GLA-SQEM were not shown to be significantly higher than those obtained with MF59 (p_values >0.093). At day 208 (FIG. 4), i.e. 7 months after the 2nd injection, no or low neutralizing antibody titers were detected in mice immunized with unadjuvanted CMV-gB and pentamer (GMT≤5 on MRC-5 and ≤50 on ARPE-19 cells, respectively). In adjuvanted sub-groups 2, no significant decrease of neutralizing titers on ARPE-19 epithelial cells was exhibited as compared to the titers detected at day 34 (in mice from subgroups 1), whatever the presence or absence of complement, whereas significant decrease was evidenced in neutralizing antibody titers on MRC-5 fibroblasts (2.3- to 5.4-fold decrease in presence of complement, all p_values ≤0.016; 3- to 10-fold decrease in absence of complement, all p_values <0.001).

With respect to the neutralizing antibody titers on ARPE-19 epithelial cells in presence or absence of complement (FIG. 4, panel A and B), no significant difference was detected between the tested adjuvants and the MF59 benchmark. With respect to the neutralizing antibody titers on MRC-5 fibroblasts in presence of complement (FIG. 4, panel C), the neutralizing antibody titers induced by PAA and GLA-SQEM were significantly higher than those induced by MF59 (at least 3.4- to 11.9-fold higher, test of superiority, unilateral Dunnet adjustment, all p_values ≤0.015).

Lastly, with respect to the neutralizing antibody titers on MRC-5 fibroblasts in absence of complement (FIG. 4, panel D), the neutralizing antibody titers induced by PAA and AF04 were significantly higher than those induced by MF59

(2- to 4.4-fold increase, test of superiority, unilateral Dunnet adjustment, all p_values ≤0.019).

At day 257 (FIG. 5), i.e. 30 days after the 3rd injection, neutralizing antibody titers in mice immunized with unadjuvanted CMV-gB and pentamer increased significantly compared to the titers detected at day 34 on ARPE-19 cells (GMT=1062 or 815 on ARPE-19 cells with and without complement, respectively). At the opposite, the neutralizing antibody titers in mice immunized with unadjuvanted CMV-gB and pentamer remained low on MRC-5 fibroblasts (GMT=29 or 15 on MRC-5 fibroblasts with and without complement, respectively).

In all adjuvanted sub-groups 3 except MF59, the neutralizing antibody titers detected at day 257 after the 3rd injection were significantly higher than those detected at day 34 after the 2nd injection, whatever the cell type and whatever the presence or absence of complement (all p_values ≤0.002).

At day 257, with respect to the adjuvant comparison to the MF59 reference, all the adjuvants (i.e. PAA and AF04) except GLA-SQEM induced higher neutralizing antibody titers than MF59, whatever the cell type and whatever the presence or absence of complement (test of superiority, unilateral Dunnet adjustment, all p-values ≤0.05). Regarding GLA-SQEM the induced complement dependent neutralizing antibody titers were significantly higher to those induce by MF59 (5.3- or 8.9-fold higher in ARPE-19 or MRC-5 cells respectively, test of superiority, unilateral Dunnet adjustment, all p_values <0.001), whereas in absence of complement the induced neutralizing were not significantly different, whatever the cell type.

At D208, i.e. up to 7 months after the $2^{nd}$ injection the composition comprising gB+Pentamer+AF04 or PAA or GLA-SQEM give higher neutralization antibody levels than a composition comprising gB+Pentamer+MF59, showing a better persistence of the functionality of the antibodies. At D257, 1 month after the boost, the measured neutralizing antibody increase reflects the memory response and shows higher titers for composition comprising gB+Pentamer+ AF04 or PAA or GLA-SQEM than a composition comprising gB+Pentamer+MF59.

All these results show that the immunogenic composition comprising gB+Pentamer+AF04 or PAA or GLA-SQEM give higher neutralization antibody levels and persistence than a composition comprising gB+Pentamer+MF59.

IgG1 and IgG2c Antibody Responses

CMV gB-specific and pentamer-specific IgG1 and IgG2c antibody responses elicited by the CMV gB and pentamer antigens administered without or with different adjuvants were measured by ELISA in individual serum samples collected from all animals from subgroups 1, 2 and 3 at, respectively, days 34 (2 weeks after the second immunization), 208 (7 months after the primary vaccination series) and 257 (1 month after the booster injection at M7). Mean ELISA antibody titers (log 10 EU) are depicted in FIG. 6. ELISA technique is detailed in the material and method section.

With respect to the IgG1 and IgG2c antibody responses similar profiles were obtained irrespective of the CMV-antigen specificity either gB or pentamer, whatever the analyzed time-point.

Regarding IgG1 antibody titers, all the tested adjuvants significantly increased the IgG1 antibody titers compared to the unadjuvanted group. No significant difference was shown for AF04 when compared to MF59, whatever the antigen and the time-point. An adjuvant effect with significantly lower IgG1 titers than MF59 was observed for PAA at day 34 and 208 (at least 2.4-fold decrease, all p-values ≤0.045, test of difference, unilateral Dunnet adjustment) but not at day 257 after the 3rd booster injection. Compared to the MF59 reference, GLA-SQEM induced significantly lower anti-gB IgG1 titers (at least 2.5-fold decrease, all p-values ≤0.033, test of difference, unilateral Dunnet adjustment) at all the tested time-point and lower anti-pentamer IgG1 titers (at least 2.7-fold decrease, all p-values ≤0.005, test of difference, unilateral Dunnet adjustment) at day 208 and 257. Regarding IgG2c antibody titers, all the tested adjuvants significantly increased the IgG2c antibody titers compared to the unadjuvanted group. An adjuvant effect with significantly higher IgG2c titers than MF59 was observed for all the tested adjuvants i.e. PAA, AF04 and GLA-SQEM (at-least 11-fold higher; all p-values <0.001, test of difference, unilateral Dunnet adjustment) either for IgG2c specific to gB or pentamer whatever the time-point.

ELISA IgG1/IgG2c Ratio

In order to evaluate the Th2/Th1 orientation, IgG1/IgG2c ratios were calculated for all the adjuvanted groups and are detailed in FIG. 7.

As shown in FIG. 7, the IgG1/IgG2c ratios calculated for CMV-pentamer were lower than those calculated for CMV-gB and tented to be constant whatever the time-point. The squalene emulsion MF59 showed a Th2-biased response profile with IgG1/IgG2 ratio for CMV-gB or ≥18 for CMV-pentamer, whatever the time-point. For all the other tested adjuvants, lower IgG1/IgG2c ratios than MF59 were obtained, with IgG1/IgG2c ratio specific to gB ≥7.1 and specific to pentamer 2.1 for AF04 and inferior or equal to 2.4 or 0.8 (specific to gB and pentamer, respectively) for PAA and GLA-SQEM, indicating a more Th1-biased response profile than the MF59 and that AF04, PAA and GLA-SQEM are Th1-inducing adjuvants.

Cellular Response

IL5 and IFN-γ Cytokine Secreting Cells Monitored by FLUOROSPOT

The IL5 and IFN-γ secreting cell frequencies were measured by FLUOROSPOT on splenocytes collected from all animals from subgroups 1, 2 and 3 at, respectively, days 34 (2 weeks after the second immunization), 208 (7 months after the primary vaccination series) and 257 (1 month after the booster injection at M7). During the FLUOROSPOT assay, each splenocyte suspension was ex-vivo stimulated overnight with either 0.1 µg/ml of recombinant CMV-gB or CMV-pentamer.

The FLUOROSPOT technique is detailed in the material and methods section.

As shown in FIG. 8, at day 34, upon CMV-gB stimulation (panel A), no or very low IL-5 secreting cell (SC) frequencies were detected in all the groups (geometric mean <22 IL-5 secreting cells/$10^6$ splenocytes) except for the MF59 adjuvanted CMV-gB and pentamer group (geometric mean of 60 IL-5 secreting cells/$10^6$ splenocytes). Similarly, no or few IFN-γ secreting cell frequencies were detected in all the groups (geometric mean <20 IFN-γ secreting cells/$10^6$ splenocytes).

At the opposite, high cytokine secreting cell frequencies were detected upon CMV-pentamer stimulation (FIG. 8, panel B). With respect to the IL-5 secreting cells, high IL-5 SC frequencies were detected in mice administered with MF59 (444 IL-5 SC/$10^6$ splenocytes). IL-5 secretions detected in groups administered with PAA and GLA-SQEM were significantly lower than those obtained with MF59 (p-values ≤0.002, test of difference, unilateral Dunnet adjustment) whereas no significant differences were recorded with AF04.

With respect to the IFN-γ secreting cells frequencies, all the tested adjuvants i.e. PAA, AF04 and GLA-SQEM a significant 8- up to 29-fold increase of IFN-γ production was recorded compared to MF59 (all p-values ≤0.001, test of difference, unilateral Dunnet adjustment).

At days 208, as shown in FIG. 8, both IL-5 and IFN-γ secreting cell frequencies were low, whatever the stimulation antigen.

At day 257, both IL-5 and IFN-γ responses upon CMV-gB and CMV-pentamer stimulation increased as compared to day 34, however the Th1/Th2 profiles were conserved. With respect to the IL-5 secreting cells, high IL-5 SC frequencies were detected in mice administered with MF59 (268 and 2284 IL-5 SC/$10^6$ splenocytes upon CMV-gB or pentamer stimulation, respectively).

IL-5 secretions detected in groups administered with PAA, AF04 and GLA-SQEM were significantly lower than those obtained with MF59 (p-values ≤0.003, test of difference, unilateral Dunnet adjustment).

With respect to the IFN-γ secreting cells frequencies, all the tested adjuvants i.e. PAA, AF04 and GLA-SQEM a significant increase of IFN-γ SC frequencies was recorded compared to MF59 (all p-values ≤0.001, test of difference, unilateral Dunnet adjustment). Taking together, all the tested adjuvants induced a more Th-1 biased overall response profile than MF59 consistent with the trend indicated by IgG1/IgG2c ratio.

Consistent with the trend indicated by IgG1/IgG2c ratio, taking together, all the tested adjuvants induced a Th-1 biased overall cellular response profile while MF59 induced a Th2-biased overall cellular response profile.

IgG1 and IgG2c Antibody Secreting Plasmablasts Monitored by ELISPOT

The IgG1 and IgG2c antibody secreting plasmablast frequencies were measured by ex-vivo FLUOROSPOT on splenocytes collected from all animals from subgroups 1, 2 and 3 at, respectively, days 34 (2 weeks after the second immunization), 208 (7 months after the primary vaccination series) and 257 (1 month after the booster injection at M7). During the ELISPOT assay, each splenocyte suspension was deposited in wells coated either with recombinant CMV-gB or CMV-pentamer to capture either IgG1 or IgG2c specific antibodies presented at the plasmablast cell surface. IgG1 and IgG2c CMV-gB and pentamer-specific Antibody Secreting cells are enumerated and reported according the total IgG secreting cells; percentage of either IgG1 or IgG2c on total IgG are calculated. The FLUOROSPOT technique is detailed in the material and methods section.

As presented in FIG. 9, the means of IgG1 antibody secreting cells (ASC) frequencies at day 34 were ranging between 3.8% and 20.12% without significant differences between all the tested adjuvants. Regarding the IgG2c ASC frequencies, low % were detected when mice were administered with CMV-gB and pentamer adjuvanted with MF59. At the opposite, CMV-gB and pentamer adjuvanted with PAA, AF04 and GLA-SQEM induced significantly higher % of IgG2c ASC than MF59 (all p_values <0.001, test of difference, unilateral Dunnet adjustment), whatever the antigen specificity either CMV-gB or CMV-pentamer.

As expected, with respect to the detected ASC at day 208, responses were low, indicating that 6 months after the primary vaccination series, low rates of circulating plasmablasts were detected in mouse spleens.

Thirty days after the 3rd injection (at day 257), the ASC frequencies, either IgG1 or IgG2c specific to CMV-gB or CMV-pentamer, increased as compared to day 208. Again, the means of IgG1 ASC frequencies at day 257 were ranging between 3.1% and 9% without significant differences between all the tested adjuvants. Regarding the IgG2c ASC frequencies, low % were detected when mice were administered with CMV-gB and pentamer adjuvanted with MF59. At the opposite, CMV-gB and pentamer adjuvanted with PAA, AF04 and GLA-SQEM induced significantly higher % of IgG2c ASC than MF59 (all p_values <0.001, test of difference, unilateral Dunnet adjustment), whatever the antigen specificity either CMV-gB or CMV-pentamer.

IgG1 and IgG2c Antibody Secreting B Memory Cells Monitored by FLUOROSPOT

The IgG1 and IgG2c antibody secreting cells frequencies were measured by FLUOSPOT at day 34, 208 and 257 on activated and enriched B cell splenocyte cultured for 4 days upon in vitro stimulation with IL-2 and R848. The FLUOROSPOT technique is detailed in the material and methods section.

As presented in FIG. 10, the means of IgG1 antibody secreting cells (ASC) frequencies at day 34 were ranging between 1.24% and 4.68% without significant differences between all the tested adjuvants and with similar profiles regarding the antigen specificity either CMV-gB or CMV-pentamer. Regarding the IgG2c ASC frequencies, low % were detected when mice were administered with CMV-gB and pentamer adjuvanted with MF59. At the opposite, CMV-gB and pentamer adjuvanted with PAA, AF04 and GLA-SQEM induced significantly higher % of IgG2c ASC than MF59 (all p_values <0.001, test of difference, unilateral Dunnet adjustment), whatever the antigen specificity either CMV-gB or CMV-pentamer.

With respect to the detected ASC at day 208, B memory cells were detected mainly for IgG1 ASC specific to CMV-pentamer with % ranging from 1.6% to 3.24% independently of the tested adjuvant. Regarding the IgG2c ASC frequencies, low % were detected when mice were administered with CMV-gB and pentamer adjuvanted with MF59. At the opposite, CMV-gB and pentamer adjuvanted with PAA, AF04 and GLA-SQEM induced significantly higher % of IgG2c ASC than MF59 (all p_values <0.001, test of difference, unilateral Dunnet adjustment).

Thirty days after the 3rd injection (at day 257), the means of IgG1 ASC frequencies were ranging between 1.1% and 3.75% without significant differences between all the tested adjuvants.

Regarding the IgG2c ASC frequencies, low % were detected when mice were administered with CMV-gB and pentamer adjuvanted with MF59. At the opposite, CMV-gB and pentamer adjuvanted with PAA and GLA-SQEM induced significantly higher % of IgG2c ASC than MF59 (all p_values <0.001, test of difference, unilateral Dunnet adjustment), whatever the antigen specificity either CMV-gB or CMV-pentamer.

These results show a higher memory response level with a composition comprising gB+pentamer+PAA or AF04 or GLA-SQEM than a composition comprising gB+pentamer+MF59. It is clear also that this higher memory cell frequency, which is known to be the mediator of the protection persistence, keeps a predominant Th1-type response profile.

Example 2

Complementary Effect of the Two Antigens

In a design of experiment study the inventors studied the combined dose-ranging effect of the two antigens in presence of PAA adjuvant. For that purpose 11 groups of 10 female C57/Bl6J mice received by intra-muscular route on days 0 and 22 doses ranging from 0 to 5 μg of CMV-gH/ gL/UL128/UL130/UL131 pentamer with or without doses ranging from 1.2 to 5 µg of CMV-gB in presence of PAA adjuvant. The antibody response was assessed by ELISA specific to gB and gH/gL/UL128/UL130/UL131 pentamer (IgG1/IgG2c subclasses) and neutralization assays on D22 (with complement, on ARPE-19 epithelial cells) and D35 (with and without complement, on MRC5 fibroblasts and ARPE-19 epithelial cells). The cellular response was assessed on D35 by IFN-y ELISPOT upon in-vitro stimulation with gB and pentamer recombinant proteins and pentamer peptide pools.

The neutralizing activities monitored either on epithelial cells ARPE-19 or fibroblasts MRC-5 presented similar profiles, with higher neutralizing titers recorded on epithelial cells than fibroblasts (2- to 5-fold higher titers in ARPE-19 than MRC-5 cells). On day 20, (FIG. 11), i.e. 20 days after the 1$^{st}$ administration, the neutralizing antibody titers inhibiting both epithelial cells and fibroblasts infection in presence of baby rabbit complement increased depending on the administered dose of gB and gH/gL/UL128/UL130/UL131 pentamer. A higher neutralizing titers increase was evidenced when the gB concentration increased. As depicted in FIG. 11, the radar plot is oriented according to the gB dosage rather than the pentamer dosage. Therefore, a significant linear effect of the addition of gB on the top of gH/gL/UL128/UL130/UL131 pentamer was observed for neutralizing activities monitored on epithelial cells and on fibroblasts (p=0.014 on epithelial cells and p=0.006 on fibroblasts).

In conclusion, in presence of complement, the addition of the gB on the top of pentamer allows to increase the SN titers on both epithelial and fibroblast cells.

On day 35, i.e. 14 days after the 2nd administration, high neutralizing antibody titers inhibiting both epithelial cells and fibroblasts infection in presence of baby rabbit complement were detected whatever the administered doses of either gB or gH/gL/UL128/UL130/UL131 pentamer. The detected neutralizing activities were at a plateau with no significant dose effect for neither the pentamer nor the gB (all p-values ≥0.240) (FIG. 12A).

On day 35, the complement independent neutralizing activities inhibiting both epithelial cells and fibroblasts infection in absence of baby rabbit complement was also monitored.

As depicted in FIG. 12B, in absence of complement the radar plot is oriented according to the pentamer dosages rather than the gB dosages, therefore the complement independent neutralizing antibody titers highly increased when the gH/gL/UL128/UL130/UL131 pentamer dose increased. No significant dose effect of the gB was evidenced whereas a significant linear and square effect was evidenced for the gH/gL/UL128/UL130/UL131 pentamer increasing doses (p≤009 for both the neutralizing titers on ARPE-19 and MRC-5 cells).

In conclusion, in absence of complement, the addition of the pentamer on the top of gB allows to increase the SN titers on both epithelial and fibroblast cells Thus, complementary effect of the two antigens was evidenced by their respective effect on the neutralizing antibody response quality. With respect to the analysis of the functional humoral responses, i.e. the complement dependent and independent neutralizing antibodies, it was demonstrated that the combination of the two antigens provided an extended mode of action for virus neutralization. CMV-gB allows increasing neutralizing antibody titers on epithelial cells and fibroblasts in presence of complement and CMV-gH/gL/UL128/UL130/UL131 pentamer allows achieving complement independent neutralizing antibody on epithelial cells and fibroblasts.

Moreover, this broadening property of the CMV-gB and CMV-gH/gL/UL128/UL130/UL131 pentamer combination was also noticed on the induced cellular responses. As depicted in FIG. 13 panel A, specific IFN-γ cellular response was detected in splenocytes from mice administered with CMV-gB and CMV-gH/gL/UL128/UL130/UL131 pentamer formulated with PAA adjuvant. Higher specific IFN-y cellular response was detected upon ex-vivo stimulation with CMV-gH/gL/UL128/UL130/UL131 recombinant pentamer than CMV-gB recombinant protein. In order to define the cellular epitopes within the CMV-gH/gL/UL128/UL130/UL131 pentamer, splenocytes from mice administered with CMV-gB and CMV-gH/gL/UL128/UL130/UL131 pentamer formulated with PAA adjuvant were also ex-vivo stimulated with 15-mer peptides pools covering the sequence of each individual protein constituting the pentamer, i.e. gH, gL, UL128, UL130 and UL131. As depicted in FIG. 13 panel B, sustained specific IFN-γ cellular response was detected for all the peptides pools covering the sequence of each individual protein constituting the pentamer except UL128 for which the detected IFN-γ cellular response was low for most of the tested mice.

In conclusion, the addition of the pentamer on the top of gB allows to increase the IFN-γ cellular response by broadening the number of cellular epitopes.

The invention claimed is:

1. A subunit vaccine comprising an immunogenic composition consisting of:
    a purified protein HCMV gB antigen;
    a purified protein HCMV gH/gL/UL128/UL130/UL131 pentameric complex antigen; and
    a Th1-inducing adjuvant, wherein said Th1-inducing adjuvant comprises a TLR4 agonist or a linear or branched polyacrylic acid polymer salt with a weight average molecular weight Mw in the range of 350 to 650 kDa.

2. The subunit vaccine according to claim 1, wherein said Th1-inducing adjuvant induces in mice a lower IgG1:IgG2a,c ratio, and/or a higher INF-γ level, and/or a lower IL-5 level than MF59 in a composition comprising the same purified protein HCMV gB antigen and the same purified protein HCMV gH/gL/UL128/UL130/UL131 pentameric complex antigen.

3. The subunit vaccine according to claim 1, wherein said purified protein HCMV gB antigen comprises one or several mutations at the endoproteolytic cleavage site.

4. The subunit vaccine according to claim 1, wherein said purified protein HCMV gB antigen is a full length gB polypeptide, a full length gB polypeptide lacking at least a portion of a transmembrane domain of the gB polypeptide, a full length gB polypeptide lacking at least 80% of the amino acid sequence of the transmembrane domain, a full length gB polypeptide lacking at least a portion of an intracellular domain of the gB polypeptide, a full length gB polypeptide lacking at least 80% of the amino acid sequence of the intracellular domain, or a full length gB polypeptide lacking at least 80% of the amino acid sequences of both the transmembrane domain and the intracellular domain.

5. The subunit vaccine according to claim 1, wherein said purified protein HCMV gB antigen is gBdTm.

6. The subunit vaccine according to claim 1, wherein in the said purified protein HCMV gH/gL/UL128/UL130/UL131 pentameric complex antigen, the gH antigen lacks at least a portion of a transmembrane domain of the full length gH.

7. The subunit vaccine according to claim 6, wherein said gH antigen comprises an ectodomain of the full length gH encoded by UL75 gene.

8. The subunit vaccine according to claim 1, wherein the purified protein HCMV gB and the purified protein HCMV gH/gL/UL128/UL130/UL131 pentameric complex are the sole HCMV protein antigens.

9. The subunit vaccine according to claim 1, wherein said vaccine increases neutralizing antibody levels and/or persistence.

10. The subunit vaccine according to claim 6, wherein in the purified protein HCMV gH/gL/UL128/UL130/UL131 pentameric complex antigen, the gH antigen lacks at least 80% of the amino acid sequence corresponding to the transmembrane domain.

11. A subunit vaccine comprising an immunogenic composition consisting of:
   a purified protein HCMV gB antigen;
   a purified protein HCMV gH/gL/UL128/UL130/UL131 pentameric complex antigen; and
   a TLR4 agonist.

12. The subunit vaccine according to claim 11, wherein said TLR4 agonist is in combination with a delivery system.

13. The subunit vaccine according to claim 12, wherein the delivery system is selected from the group consisting of aqueous nanosuspension, calcium phosphate, liposomes, virosomes, ISCOMs, micro- and nanoparticles, and emulsions.

14. The subunit vaccine according to claim 11, wherein said TLR-4 agonist is selected from the group consisting of: a lipopolysaccharide, a monophosphoryl lipid A (MPL), a 3-de-O-acylated monophosphoryl lipid A (3D-MPL), a glucopyranosyl lipid adjuvant (GLA), a second-generation Lipid Adjuvant (SLA), a phospholipid dimer connected by a noncarbohydrate backbone and an aminoalkyl glucosaminide phosphate, or a derivative thereof.

15. The subunit vaccine according to claim 12, wherein TLR-4 agonist in combination with a delivery system is AS01 or AS02.

16. The subunit vaccine according to claim 11, wherein said TLR-4 agonist is GLA (CAS Number 1246298-63-4) TLR-4 agonist.

17. A subunit vaccine comprising an immunogenic composition consisting of:
   a purified protein HCMV gB antigen;
   a purified protein HCMV gH/gL/UL128/UL130/UL131 pentameric complex antigen; and
   a linear or branched polyacrylic acid polymer salt with a weight average molecular weight Mw in the range of 350 to 650 kDa.

18. The subunit vaccine according to claim 17, wherein said linear or branched polyacrylic acid polymer salt is PAA225000.

19. A method of preventing a disease associated with HCMV infection in a patient in need thereof, comprising the administration of an immunologically effective amount of a subunit vaccine comprising an immunogenic composition consisting of:
   a purified protein HCMV gB antigen;
   a purified protein HCMV gH/gL/UL128/UL130/UL131 pentameric complex antigen; and
   a TLR4 agonist or a linear or branched polyacrylic acid polymer salt with a weight average molecular weight Mw in the range of 350 to 650 kDa, thereby preventing the disease associated with HMCV infection in the patient.

20. A method of producing a subunit vaccine comprising an immunogenic composition, the method comprising:
   providing purified protein antigens consisting of a purified protein HCMV gB antigen and a purified protein HCMV gH/gL/UL128/UL130/UL131 pentameric complex antigen; and
   combining the purified protein antigens with a TLR4 agonist, to thereby produce an immunogenic composition.

* * * * *

SEQUENCE LISTING

```
<160> NUMBER OF SEQ ID NOS: 6

<210> SEQ ID NO 1
<211> LENGTH: 806
<212> TYPE: PRT
<213> ORGANISM: Artificial Sequence
<220> FEATURE:
<223> OTHER INFORMATION: gB antigen

<400> SEQUENCE: 1

Ser Ser Thr Arg Gly Thr Ser Ala Thr His Ser His His Ser Ser His
1               5                   10                  15

Thr Thr Ser Ala Ala His Ser Arg Ser Gly Ser Val Ser Gln Arg Val
            20                  25                  30

Thr Ser Ser Gln Thr Val Ser His Gly Val Asn Glu Thr Ile Tyr Asn
        35                  40                  45
```

```
Thr Thr Leu Lys Tyr Gly Asp Val Gly Val Asn Thr Thr Lys Tyr
     50                  55                  60

Pro Tyr Arg Val Cys Ser Met Ala Gln Gly Thr Asp Leu Ile Arg Phe
65                   70                  75                  80

Glu Arg Asn Ile Val Cys Thr Ser Met Lys Pro Ile Asn Glu Asp Leu
                     85                  90                  95

Asp Glu Gly Ile Met Val Val Tyr Lys Arg Asn Ile Val Ala His Thr
                100                 105                 110

Phe Lys Val Arg Val Tyr Gln Lys Val Leu Thr Phe Arg Arg Ser Tyr
             115                 120                 125

Ala Tyr Ile His Thr Thr Tyr Leu Leu Gly Ser Asn Thr Glu Tyr Val
     130                 135                 140

Ala Pro Pro Met Trp Glu Ile His Ile Asn Ser His Ser Gln Cys
145                 150                 155                 160

Tyr Ser Ser Tyr Ser Arg Val Ile Ala Gly Thr Val Phe Val Ala Tyr
                 165                 170                 175

His Arg Asp Ser Tyr Glu Asn Lys Thr Met Gln Leu Met Pro Asp Asp
             180                 185                 190

Tyr Ser Asn Thr His Ser Thr Arg Tyr Val Thr Val Lys Asp Gln Trp
         195                 200                 205

His Ser Arg Gly Ser Thr Trp Leu Tyr Arg Glu Thr Cys Asn Leu Asn
     210                 215                 220

Cys Met Val Thr Ile Thr Thr Ala Arg Ser Lys Tyr Pro Tyr His Phe
225                 230                 235                 240

Phe Ala Thr Ser Thr Gly Asp Val Val Asp Ile Ser Pro Phe Tyr Asn
                 245                 250                 255

Gly Thr Asn Arg Asn Ala Ser Tyr Phe Gly Glu Asn Ala Asp Lys Phe
             260                 265                 270

Phe Ile Phe Pro Asn Tyr Thr Ile Val Ser Asp Phe Gly Arg Pro Asn
         275                 280                 285

Ser Ala Leu Glu Thr His Arg Leu Val Ala Phe Leu Glu Arg Ala Asp
     290                 295                 300

Ser Val Ile Ser Trp Asp Ile Gln Asp Glu Lys Asn Val Thr Cys Gln
305                 310                 315                 320

Leu Thr Phe Trp Glu Ala Ser Glu Arg Thr Ile Arg Ser Glu Ala Glu
                 325                 330                 335

Asp Ser Tyr His Phe Ser Ser Ala Lys Met Thr Ala Thr Phe Leu Ser
             340                 345                 350

Lys Lys Gln Glu Val Asn Met Ser Asp Ser Ala Leu Asp Cys Val Arg
         355                 360                 365

Asp Glu Ala Ile Asn Lys Leu Gln Gln Ile Phe Asn Thr Ser Tyr Asn
     370                 375                 380

Gln Thr Tyr Glu Lys Tyr Gly Asn Val Ser Val Phe Glu Thr Thr Gly
385                 390                 395                 400

Gly Leu Val Val Phe Trp Gln Gly Ile Lys Gln Lys Ser Leu Val Glu
                 405                 410                 415

Leu Glu Arg Leu Ala Asn Arg Ser Ser Leu Asn Leu Thr His Asn Thr
             420                 425                 430

Thr Gln Thr Ser Thr Asp Gly Asn Asn Ala Thr His Leu Ser Asn Met
         435                 440                 445

Glu Ser Val His Asn Leu Val Tyr Ala Gln Leu Gln Phe Thr Tyr Asp
     450                 455                 460
```

```
Thr Leu Arg Gly Tyr Ile Asn Arg Ala Leu Ala Gln Ile Ala Glu Ala
465                 470                 475                 480

Trp Cys Val Asp Gln Arg Arg Thr Leu Glu Val Phe Lys Glu Leu Ser
            485                 490                 495

Lys Ile Asn Pro Ser Ala Ile Leu Ser Ala Ile Tyr Asn Lys Pro Ile
        500                 505                 510

Ala Ala Arg Phe Met Gly Asp Val Leu Gly Leu Ala Ser Cys Val Thr
    515                 520                 525

Ile Asn Gln Thr Ser Val Lys Val Leu Arg Asp Met Asn Val Lys Glu
530                 535                 540

Ser Pro Gly Arg Cys Tyr Ser Arg Pro Val Val Ile Phe Asn Phe Ala
545                 550                 555                 560

Asn Ser Ser Tyr Val Gln Tyr Gly Gln Leu Gly Glu Asp Asn Glu Ile
                565                 570                 575

Leu Leu Gly Asn His Arg Thr Glu Glu Cys Gln Leu Pro Ser Leu Lys
            580                 585                 590

Ile Phe Ile Ala Gly Asn Ser Ala Tyr Glu Tyr Val Asp Tyr Leu Phe
        595                 600                 605

Lys Arg Met Ile Asp Leu Ser Ser Ile Ser Thr Val Asp Ser Met Ile
    610                 615                 620

Ala Leu Asp Ile Asp Pro Leu Glu Asn Thr Asp Phe Arg Val Leu Glu
625                 630                 635                 640

Leu Tyr Ser Gln Lys Glu Leu Arg Ser Ser Asn Val Phe Asp Leu Glu
                645                 650                 655

Glu Ile Met Arg Glu Phe Asn Ser Tyr Lys Gln Arg Val Lys Tyr Val
            660                 665                 670

Glu Asp Lys Arg Leu Cys Met Gln Pro Leu Gln Asn Leu Phe Pro Tyr
        675                 680                 685

Leu Val Ser Ala Asp Gly Thr Thr Val Thr Ser Gly Asn Thr Lys Asp
    690                 695                 700

Thr Ser Leu Gln Ala Pro Pro Ser Tyr Glu Glu Ser Val Tyr Asn Ser
705                 710                 715                 720

Gly Arg Lys Gly Pro Gly Pro Pro Ser Ser Asp Ala Ser Thr Ala Ala
                725                 730                 735

Pro Pro Tyr Thr Asn Glu Gln Ala Tyr Gln Met Leu Leu Ala Leu Val
            740                 745                 750

Arg Leu Asp Ala Glu Gln Arg Ala Gln Gln Asn Gly Thr Asp Ser Leu
        755                 760                 765

Asp Gly Gln Thr Gly Thr Gln Asp Lys Gly Gln Lys Pro Asn Leu Leu
    770                 775                 780

Asp Arg Leu Arg His Arg Lys Asn Gly Tyr Arg His Leu Lys Asp Ser
785                 790                 795                 800

Asp Glu Glu Glu Asn Val
                805

<210> SEQ ID NO 2
<211> LENGTH: 694
<212> TYPE: PRT
<213> ORGANISM: Artificial Sequence
<220> FEATURE:
<223> OTHER INFORMATION: gH polypeptide

<400> SEQUENCE: 2

Arg Tyr Gly Ala Glu Ala Val Ser Glu Pro Leu Asp Lys Ala Phe His
1               5                   10                  15
```

Leu Leu Leu Asn Thr Tyr Gly Arg Pro Ile Arg Phe Leu Arg Glu Asn
            20                  25                  30

Thr Thr Gln Cys Thr Tyr Asn Asn Ser Leu Arg Asn Ser Thr Val Val
        35                  40                  45

Arg Glu Asn Ala Ile Ser Phe Asn Phe Phe Gln Ser Tyr Asn Gln Tyr
    50                  55                  60

Tyr Val Phe His Met Pro Arg Cys Leu Phe Ala Gly Pro Leu Ala Glu
65                  70                  75                  80

Gln Phe Leu Asn Gln Val Asp Leu Thr Glu Thr Leu Glu Arg Tyr Gln
                85                  90                  95

Gln Arg Leu Asn Thr Tyr Ala Leu Val Ser Lys Asp Leu Ala Ser Tyr
            100                 105                 110

Arg Ser Phe Ser Gln Gln Leu Lys Ala Gln Asp Ser Leu Gly Glu Gln
        115                 120                 125

Pro Thr Thr Val Pro Pro Ile Asp Leu Ser Ile Pro His Val Trp
    130                 135                 140

Met Pro Pro Gln Thr Thr Pro His Gly Trp Thr Glu Ser His Thr Thr
145                 150                 155                 160

Ser Gly Leu His Arg Pro His Phe Asn Gln Thr Cys Ile Leu Phe Asp
                165                 170                 175

Gly His Asp Leu Leu Phe Ser Thr Val Thr Pro Cys Leu His Gln Gly
            180                 185                 190

Phe Tyr Leu Ile Asp Glu Leu Arg Tyr Val Lys Ile Thr Leu Thr Glu
        195                 200                 205

Asp Phe Phe Val Val Thr Val Ser Ile Asp Asp Thr Pro Met Leu
210                 215                 220

Leu Ile Phe Gly His Leu Pro Arg Val Leu Phe Lys Ala Pro Tyr Gln
225                 230                 235                 240

Arg Asp Asn Phe Ile Leu Arg Gln Thr Glu Lys His Glu Leu Leu Val
                245                 250                 255

Leu Val Lys Lys Asp Gln Leu Asn Arg His Ser Tyr Leu Lys Asp Pro
            260                 265                 270

Asp Phe Leu Asp Ala Ala Leu Asp Phe Asn Tyr Leu Asp Leu Ser Ala
        275                 280                 285

Leu Leu Arg Asn Ser Phe His Arg Tyr Ala Val Asp Val Leu Lys Ser
290                 295                 300

Gly Arg Cys Gln Met Leu Asp Arg Arg Thr Val Glu Met Ala Phe Ala
305                 310                 315                 320

Tyr Ala Leu Ala Leu Phe Ala Ala Arg Gln Glu Glu Ala Gly Ala
                325                 330                 335

Gln Val Ser Val Pro Arg Ala Leu Asp Arg Gln Ala Ala Leu Leu Gln
            340                 345                 350

Ile Gln Glu Phe Met Ile Thr Cys Leu Ser Gln Thr Pro Pro Arg Thr
        355                 360                 365

Thr Leu Leu Leu Tyr Pro Thr Ala Val Asp Leu Ala Lys Arg Ala Leu
370                 375                 380

Trp Thr Pro Asn Gln Ile Thr Asp Ile Thr Ser Leu Val Arg Leu Val
385                 390                 395                 400

Tyr Ile Leu Ser Lys Gln Asn Gln Gln His Leu Ile Pro Gln Trp Ala
                405                 410                 415

Leu Arg Gln Ile Ala Asp Phe Ala Leu Lys Leu His Lys Thr His Leu
            420                 425                 430

Ala Ser Phe Leu Ser Ala Phe Ala Arg Gln Glu Leu Tyr Leu Met Gly

```
                435                 440                 445
Ser Leu Val His Ser Met Leu Val His Thr Thr Glu Arg Arg Glu Ile
    450                 455                 460

Phe Ile Val Glu Thr Gly Leu Cys Ser Leu Ala Glu Leu Ser His Phe
465                 470                 475                 480

Thr Gln Leu Leu Ala His Pro His His Glu Tyr Leu Ser Asp Leu Tyr
                485                 490                 495

Thr Pro Cys Ser Ser Ser Gly Arg Arg Asp His Ser Leu Glu Arg Leu
            500                 505                 510

Thr Arg Leu Phe Pro Asp Ala Thr Val Pro Ala Thr Val Pro Ala Ala
        515                 520                 525

Leu Ser Ile Leu Ser Thr Met Gln Pro Ser Thr Leu Glu Thr Phe Pro
    530                 535                 540

Asp Leu Phe Cys Leu Pro Leu Gly Glu Ser Phe Ser Ala Leu Thr Val
545                 550                 555                 560

Ser Glu His Val Ser Tyr Val Val Thr Asn Gln Tyr Leu Ile Lys Gly
                565                 570                 575

Ile Ser Tyr Pro Val Ser Thr Val Val Gly Gln Ser Leu Ile Ile
            580                 585                 590

Thr Gln Thr Asp Ser Gln Thr Lys Cys Glu Leu Thr Arg Asn Met His
        595                 600                 605

Thr Thr His Ser Ile Thr Ala Ala Leu Asn Ile Ser Leu Glu Asn Cys
    610                 615                 620

Ala Phe Cys Gln Ser Ala Leu Leu Glu Tyr Asp Asp Thr Gln Gly Val
625                 630                 635                 640

Ile Asn Ile Met Tyr Met His Asp Ser Asp Val Leu Phe Ala Leu
                645                 650                 655

Asp Pro Tyr Asn Glu Val Val Ser Ser Pro Arg Thr His Tyr Leu
            660                 665                 670

Met Leu Leu Lys Asn Gly Thr Val Leu Glu Val Thr Asp Val Val Val
        675                 680                 685

Asp Ala Thr Asp Ser Arg
    690

<210> SEQ ID NO 3
<211> LENGTH: 248
<212> TYPE: PRT
<213> ORGANISM: Artificial Sequence
<220> FEATURE:
<223> OTHER INFORMATION: gL polypeptide

<400> SEQUENCE: 3

Ala Ala Val Ser Val Ala Pro Thr Ala Ala Glu Lys Val Pro Ala Glu
1               5                   10                  15

Cys Pro Glu Leu Thr Arg Arg Cys Leu Leu Gly Glu Val Phe Gln Gly
                20                  25                  30

Asp Lys Tyr Glu Ser Trp Leu Arg Pro Leu Val Asn Val Thr Gly Arg
            35                  40                  45

Asp Gly Pro Leu Ser Gln Leu Ile Arg Tyr Arg Pro Val Thr Pro Glu
        50                  55                  60

Ala Ala Asn Ser Val Leu Leu Asp Glu Ala Phe Leu Asp Thr Leu Ala
65                  70                  75                  80

Leu Leu Tyr Asn Asn Pro Asp Gln Leu Arg Ala Leu Leu Thr Leu Leu
                85                  90                  95

Ser Ser Asp Thr Ala Pro Arg Trp Met Thr Val Met Arg Gly Tyr Ser
```

```
            100                 105                 110
Glu Cys Gly Asp Gly Ser Pro Ala Val Tyr Thr Cys Val Asp Asp Leu
        115                 120                 125

Cys Arg Gly Tyr Asp Leu Thr Arg Leu Ser Tyr Glu Arg Ser Ile Phe
    130                 135                 140

Thr Glu His Val Leu Gly Phe Glu Leu Val Pro Ser Leu Phe Asn
145                 150                 155                 160

Val Val Val Ala Ile Arg Asn Glu Ala Thr Arg Thr Asn Arg Ala Val
                165                 170                 175

Arg Leu Pro Val Ser Thr Ala Ala Pro Glu Gly Ile Thr Leu Phe
            180                 185                 190

Tyr Gly Leu Tyr Asn Ala Val Lys Glu Phe Cys Leu Arg His Gln Leu
        195                 200                 205

Asp Pro Pro Leu Leu Arg His Leu Asp Lys Tyr Ala Gly Leu Pro
    210                 215                 220

Pro Glu Leu Lys Gln Thr Arg Val Asn Leu Pro Ala His Ser Arg Tyr
225                 230                 235                 240

Gly Pro Gln Ala Val Asp Ala Arg
                245

<210> SEQ ID NO 4
<211> LENGTH: 144
<212> TYPE: PRT
<213> ORGANISM: Artificial Sequence
<220> FEATURE:
<223> OTHER INFORMATION: UL128 polypeptide

<400> SEQUENCE: 4

Glu Glu Cys Cys Glu Phe Ile Asn Val Asn His Pro Pro Glu Arg Cys
1               5                   10                  15

Tyr Asp Phe Lys Met Cys Asn Arg Phe Thr Val Ala Leu Arg Cys Pro
            20                  25                  30

Asp Gly Glu Val Cys Tyr Ser Pro Glu Lys Thr Ala Glu Ile Arg Gly
        35                  40                  45

Ile Val Thr Thr Met Thr His Ser Leu Thr Arg Gln Val Val His Asn
    50                  55                  60

Lys Leu Thr Ser Cys Asn Tyr Asn Pro Leu Tyr Leu Glu Ala Asp Gly
65              70                  75                  80

Arg Ile Arg Cys Gly Lys Val Asn Asp Lys Ala Gln Tyr Leu Leu Gly
                85                  90                  95

Ala Ala Gly Ser Val Pro Tyr Arg Trp Ile Asn Leu Glu Tyr Asp Lys
            100                 105                 110

Ile Thr Arg Ile Val Gly Leu Asp Gln Tyr Leu Glu Ser Val Lys Lys
        115                 120                 125

His Lys Arg Leu Asp Val Cys Arg Ala Lys Met Gly Tyr Met Leu Gln
    130                 135                 140

<210> SEQ ID NO 5
<211> LENGTH: 189
<212> TYPE: PRT
<213> ORGANISM: Artificial Sequence
<220> FEATURE:
<223> OTHER INFORMATION: UL130 polypeptide

<400> SEQUENCE: 5

Ser Pro Trp Ser Thr Leu Thr Ala Asn Gln Asn Pro Ser Pro Leu Trp
1               5                   10                  15
```

-continued

```
Ser Lys Leu Thr Tyr Ser Lys Pro His Asp Ala Ala Thr Phe Tyr Cys
             20                  25                  30

Pro Phe Ile Tyr Pro Ser Pro Pro Arg Ser Pro Leu Gln Phe Ser Gly
         35                  40                  45

Phe Gln Arg Val Leu Thr Gly Pro Glu Cys Arg Asn Glu Thr Leu Tyr
     50                  55                  60

Leu Leu Tyr Asn Arg Glu Gly Gln Thr Leu Val Glu Arg Ser Ser Thr
 65                  70                  75                  80

Trp Val Lys Lys Val Ile Trp Tyr Leu Ser Gly Arg Asn Gln Thr Ile
                 85                  90                  95

Leu Gln Arg Met Pro Arg Thr Ala Ser Lys Pro Ser Asp Gly Asn Val
                100                 105                 110

Gln Ile Ser Val Glu Asp Ala Lys Ile Phe Gly Ala His Met Val Pro
             115                 120                 125

Lys Gln Thr Lys Leu Leu Arg Phe Val Val Asn Asp Gly Thr Arg Tyr
         130                 135                 140

Gln Met Cys Val Met Lys Leu Glu Ser Trp Ala His Val Phe Arg Asp
145                 150                 155                 160

Tyr Ser Val Ser Phe Gln Val Arg Leu Thr Phe Thr Glu Ala Asn Asn
                 165                 170                 175

Gln Thr Tyr Thr Phe Cys Thr His Pro Asn Leu Ile Val
             180                 185

<210> SEQ ID NO 6
<211> LENGTH: 111
<212> TYPE: PRT
<213> ORGANISM: Artificial Sequence
<220> FEATURE:
<223> OTHER INFORMATION: UL131A polypeptide

<400> SEQUENCE: 6

Gln Cys Gln Arg Glu Thr Ala Glu Lys Asn Asp Tyr Tyr Arg Val Pro
1               5                  10                  15

His Tyr Trp Asp Ala Cys Ser Arg Ala Leu Pro Asp Gln Thr Arg Tyr
             20                  25                  30

Lys Tyr Val Glu Gln Leu Val Asp Leu Thr Leu Asn Tyr His Tyr Asp
         35                  40                  45

Ala Ser His Gly Leu Asp Asn Phe Asp Val Leu Lys Arg Ile Asn Val
     50                  55                  60

Thr Glu Val Ser Leu Leu Ile Ser Asp Phe Arg Arg Gln Asn Arg Arg
 65                  70                  75                  80

Gly Gly Thr Asn Lys Arg Thr Thr Phe Asn Ala Ala Gly Ser Leu Ala
                 85                  90                  95

Pro His Ala Arg Ser Leu Glu Phe Ser Val Arg Leu Phe Ala Asn
                100                 105                 110
```